US012559554B1

(12) United States Patent
Wang et al.

(10) Patent No.: US 12,559,554 B1
(45) Date of Patent: Feb. 24, 2026

(54) TSLP-BINDING MOLECULES, IL-33-BINDING MOLECULES, AND BISPECIFIC ANTIGEN-BINDING MOLECULES, AND USES THEREOF

(71) Applicant: Newsoara Biopharmaceutical Technology (Suzhou) Co., Ltd., JiangSu Province (CN)

(72) Inventors: Wenyi Wang, JiangSu Province (CN); Qingqing Yin, JiangSu Province (CN); Yuannian Li, JiangSu Province (CN)

(73) Assignee: Newsoara Biopharmaceutical Technology (Suzhou) Co., Ltd., JiangSu (CN)

( * ) Notice: Subject to any disclaimer, the term of this patent is extended or adjusted under 35 U.S.C. 154(b) by 0 days.

(21) Appl. No.: 19/085,020

(22) Filed: Mar. 20, 2025

(30) Foreign Application Priority Data

Jan. 13, 2025 (CN) .......................... 202510021382.4

(51) Int. Cl.
*C07K 16/24* (2006.01)
*A61K 39/00* (2006.01)

(52) U.S. Cl.
CPC ............ *C07K 16/244* (2013.01); *A61K 39/00* (2013.01); *C07K 2317/24* (2013.01); *C07K 2317/31* (2013.01); *C07K 2317/569* (2013.01); *C07K 2317/76* (2013.01); *C07K 2317/92* (2013.01)

(58) Field of Classification Search
None
See application file for complete search history.

*Primary Examiner* — Daniel C Gamett
(74) *Attorney, Agent, or Firm* — Dority & Manning, PA

(57) ABSTRACT

The present disclosure relates to TSLP-binding molecules, IL-33-binding molecules, and bispecific antigen-binding molecules that simultaneously target TSLP and IL-33. The disclosure also relates to nucleic acid molecules encoding said antigen-binding molecules, expression vectors, host cells, compositions thereof, and their use for treating diseases.

31 Claims, 5 Drawing Sheets

Specification includes a Sequence Listing.

| | HYB0111 | HYB0111-hz2 | HYB0111-hz3 | HYB0111-hz4 |
|---|---|---|---|---|
| EC$_{50}$[μg/mL] | 0.003084 | 0.001948 | 0.001905 | 0.001918 |

| | HYB0111 | HYB0111-hz2 | HYB0111-hz9 | Tezepelumab |
|---|---|---|---|---|
| $EC_{50}$(μg/mL) | 0.004282 | 0.002064 | 0.003053 | 0.01559 |

| | HYB0512 | HYB0512-hz1 | HYB0512-hz2 | HYB0512-hz3 | HYB0512-hz4 | HYB0512-hz5 | HYB0512-hz6 | HYB0512-hz7 | HYB0512-hz8 |
|---|---|---|---|---|---|---|---|---|---|
| $EC_{50}$ (μg/mL) | 1.117 | 0.8268 | 0.4928 | 0.9745 | 0.3996 | 1.355 | 3.078 | 3.575 | 0.5048 |

| | HYB0512-hz4 | Itepekimab | Etokimab |
|---|---|---|---|
| $EC_{50}$(μg/mL) | 0.008808 | 0.006037 | ~ 0.01233 |

| | HYB017 | Tezepelumab |
|---|---|---|
| $EC_{50}$(µg/mL) | 0.034 | 1.393 |

| | HYB017 | Tezepelumab |
|---|---|---|
| $EC_{50}$(µg/mL) | 0.004 | 0.072 |

| | HYB017 | HYB0512-hz4 | Etokimab | Itepekimab |
|---|---|---|---|---|
| EC$_{50}$(ng/mL) | 1.93 | 0.65 | 0.45 | 0.93 |

```
                           SEQUENCE LISTING

Sequence total quantity: 218
SEQ ID NO: 1              moltype = AA  length = 10
FEATURE                   Location/Qualifiers
source                    1..10
                          mol_type = protein
                          organism = synthetic construct
SEQUENCE: 1
GSNFSLYAMS                                                        10

SEQ ID NO: 2              moltype = AA  length = 9
FEATURE                   Location/Qualifiers
source                    1..9
                          mol_type = protein
                          organism = synthetic construct
SEQUENCE: 2
RIRDNGRTN                                                         9

SEQ ID NO: 3              moltype = AA  length = 7
FEATURE                   Location/Qualifiers
source                    1..7
                          mol_type = protein
                          organism = synthetic construct
SEQUENCE: 3
DNRVTTF                                                           7

SEQ ID NO: 4              moltype = AA  length = 115
FEATURE                   Location/Qualifiers
source                    1..115
                          mol_type = protein
                          organism = synthetic construct
SEQUENCE: 4
QVQLVESGGG LVQPGGSLTL SCVAAGSNFS LYAMSYYRQV PGKQRELVAR IRDNGRTNYA  60
DSVKDRFTIS RDSAKNTVYL QMHSLKPEDT AVYYCNADNR VTTFWGRGTQ VTVSS       115

SEQ ID NO: 5              moltype = AA  length = 10
FEATURE                   Location/Qualifiers
source                    1..10
                          mol_type = protein
                          organism = synthetic construct
SEQUENCE: 5
GSIFSIDAMG                                                        10

SEQ ID NO: 6              moltype = AA  length = 7
FEATURE                   Location/Qualifiers
source                    1..7
                          mol_type = protein
                          organism = synthetic construct
SEQUENCE: 6
AIGSGTY                                                           7

SEQ ID NO: 7              moltype = AA  length = 8
FEATURE                   Location/Qualifiers
source                    1..8
```

-continued

```
                          mol_type = protein
                          organism = synthetic construct
SEQUENCE: 7
GDSYPDEY                                                       8

SEQ ID NO: 8             moltype = AA   length = 115
FEATURE                  Location/Qualifiers
source                   1..115
                          mol_type = protein
                          organism = synthetic construct
SEQUENCE: 8
QLQLVESGGG LVQPGGSLRL SCAASGSIFS IDAMGWYRQA PGKERELVAA IGSGTYYADS  60
VKGRFTISRD NAKKNTLYLQ MDSLKPEDTA IYYCASGDSY PDEYWGQGTQ VTVSA      115

SEQ ID NO: 9             moltype = AA   length = 10
FEATURE                  Location/Qualifiers
source                   1..10
                          mol_type = protein
                          organism = synthetic construct
SEQUENCE: 9
ESDFSIYIMG                                                     10

SEQ ID NO: 10            moltype = AA   length = 9
FEATURE                  Location/Qualifiers
source                   1..9
                          mol_type = protein
                          organism = synthetic construct
SEQUENCE: 10
TITPGGNTN                                                       9

SEQ ID NO: 11            moltype = AA   length = 9
FEATURE                  Location/Qualifiers
source                   1..9
                          mol_type = protein
                          organism = synthetic construct
SEQUENCE: 11
RNIFRNVDY                                                       9

SEQ ID NO: 12            moltype = AA   length = 117
FEATURE                  Location/Qualifiers
source                   1..117
                          mol_type = protein
                          organism = synthetic construct
SEQUENCE: 12
QLQLVESGGG LVQPGGSLRL SCAASESDFS IYIMGWYRQA PGKQRELVVT ITPGGNTNYV  60
DSVKGRFTIS RDNTMNTAYL QMNSLKPDDT AVYYCNARNI FRNVDYSGKG TLVTVSS    117

SEQ ID NO: 13            moltype = AA   length = 10
FEATURE                  Location/Qualifiers
source                   1..10
                          mol_type = protein
                          organism = synthetic construct
SEQUENCE: 13
GIEFSIYIMG                                                     10

SEQ ID NO: 14            moltype = AA   length = 9
FEATURE                  Location/Qualifiers
source                   1..9
                          mol_type = protein
                          organism = synthetic construct
SEQUENCE: 14
TVTPGGNTN                                                       9

SEQ ID NO: 15            moltype = AA   length = 9
FEATURE                  Location/Qualifiers
source                   1..9
                          mol_type = protein
                          organism = synthetic construct
SEQUENCE: 15
RNIFRNMDY                                                       9

SEQ ID NO: 16            moltype = AA   length = 117
FEATURE                  Location/Qualifiers
source                   1..117
                          mol_type = protein
                          organism = synthetic construct
SEQUENCE: 16
QVQLVESGGG LVQPGGSLRL SCVASGIEFS IYIMGWYRQA PGKQRELVAT VTPGGNTNYA  60
DSVKGRFTIS RDNTKNTAYL QMNSLKPDDT AVYYCNARNI FRNMDYQGKG TLVTVSS    117
```

-continued

```
SEQ ID NO: 17          moltype = AA   length = 10
FEATURE                Location/Qualifiers
source                 1..10
                       mol_type = protein
                       organism = synthetic construct
SEQUENCE: 17
GSDFNIYIMG                                                      10

SEQ ID NO: 18          moltype = AA   length = 9
FEATURE                Location/Qualifiers
source                 1..9
                       mol_type = protein
                       organism = synthetic construct
SEQUENCE: 18
TITPGGNTN                                                       9

SEQ ID NO: 19          moltype = AA   length = 9
FEATURE                Location/Qualifiers
source                 1..9
                       mol_type = protein
                       organism = synthetic construct
SEQUENCE: 19
RNIFRYMDY                                                       9

SEQ ID NO: 20          moltype = AA   length = 117
FEATURE                Location/Qualifiers
source                 1..117
                       mol_type = protein
                       organism = synthetic construct
SEQUENCE: 20
QVQLVESGGG SVQPGGSLRL SCAASGSDFN IYIMGWYQQA PGKQRELVAT ITPGGNTNYV  60
DSVKGRFTIS RDNTKNTAYL QMNSLKPDDT AVYYCNARNI FRYMDYWGKG TLVTVSS     117

SEQ ID NO: 21          moltype = AA   length = 10
FEATURE                Location/Qualifiers
source                 1..10
                       mol_type = protein
                       organism = synthetic construct
SEQUENCE: 21
GFIFDDYAIA                                                      10

SEQ ID NO: 22          moltype = AA   length = 10
FEATURE                Location/Qualifiers
source                 1..10
                       mol_type = protein
                       organism = synthetic construct
SEQUENCE: 22
FISNSDGTAY                                                      10

SEQ ID NO: 23          moltype = AA   length = 23
FEATURE                Location/Qualifiers
source                 1..23
                       mol_type = protein
                       organism = synthetic construct
SEQUENCE: 23
EGRMGTHSRD SVYFWAFSAL YDY                                       23

SEQ ID NO: 24          moltype = AA   length = 132
FEATURE                Location/Qualifiers
source                 1..132
                       mol_type = protein
                       organism = synthetic construct
SEQUENCE: 24
QVQLVESGGG LVQAGGSLRL SCAASGFIFD DYAIAWFRQA PGKEREGVSF ISNSDGTAYY  60
ADSVKGRFTI SSDNAKNTVY LQMDSLKPDD TADYYCAAEG RMGTHSRDSV YFWAFSALYD  120
YWGQGTQVTV SS                                                   132

SEQ ID NO: 25          moltype = AA   length = 10
FEATURE                Location/Qualifiers
source                 1..10
                       mol_type = protein
                       organism = synthetic construct
SEQUENCE: 25
GFTFDDYAIT                                                      10

SEQ ID NO: 26          moltype = AA   length = 10
FEATURE                Location/Qualifiers
source                 1..10
```

-continued

```
                         mol_type = protein
                         organism = synthetic construct
SEQUENCE: 26
YISNSDGMTY                                                       10

SEQ ID NO: 27           moltype = AA   length = 23
FEATURE                 Location/Qualifiers
source                  1..23
                        mol_type = protein
                        organism = synthetic construct
SEQUENCE: 27
EGIMGTHNRD NVYFWAFSAL YDY                                        23

SEQ ID NO: 28           moltype = AA   length = 132
FEATURE                 Location/Qualifiers
source                  1..132
                        mol_type = protein
                        organism = synthetic construct
SEQUENCE: 28
QLQLVESGGG LVQAGGSLRL SCAASGFTFD DYAITWFRQA PGKEREGVAY ISNSDGMTYY   60
VDSVKGRFTI SSDNAKNTVY LQMDSLKPED TAVYYCAAEG IMGTHNRDNV YFWAFSALYD   120
YWGQGTQVTV SS                                                     132

SEQ ID NO: 29           moltype = AA   length = 10
FEATURE                 Location/Qualifiers
source                  1..10
                        mol_type = protein
                        organism = synthetic construct
SEQUENCE: 29
GFTFDDYAIT                                                       10

SEQ ID NO: 30           moltype = AA   length = 10
FEATURE                 Location/Qualifiers
source                  1..10
                        mol_type = protein
                        organism = synthetic construct
SEQUENCE: 30
YISNFDGMTY                                                       10

SEQ ID NO: 31           moltype = AA   length = 23
FEATURE                 Location/Qualifiers
source                  1..23
                        mol_type = protein
                        organism = synthetic construct
SEQUENCE: 31
EGRMGTHSRD SVYFWAFSAL YDH                                        23

SEQ ID NO: 32           moltype = AA   length = 132
FEATURE                 Location/Qualifiers
source                  1..132
                        mol_type = protein
                        organism = synthetic construct
SEQUENCE: 32
QVQLVESGGG LVQAGGSLRL SCAASGFTFD DYAITWFRQA PGKEREGVAY ISNFDGMTYY   60
ADSVKGRFTI SSDNAKNTVY LQMDSLKPED TAVYYCAAEG RMGTHSRDSV YFWAFSALYD   120
HWGQGTQVTV SS                                                     132

SEQ ID NO: 33           moltype = AA   length = 10
FEATURE                 Location/Qualifiers
source                  1..10
                        mol_type = protein
                        organism = synthetic construct
SEQUENCE: 33
GFTFDDYAIT                                                       10

SEQ ID NO: 34           moltype = AA   length = 10
FEATURE                 Location/Qualifiers
source                  1..10
                        mol_type = protein
                        organism = synthetic construct
SEQUENCE: 34
YISNSDGMTY                                                       10

SEQ ID NO: 35           moltype = AA   length = 23
FEATURE                 Location/Qualifiers
source                  1..23
                        mol_type = protein
                        organism = synthetic construct
SEQUENCE: 35
```

```
EGRMGTHSRD SVYFWAFSAL YDY                                              23

SEQ ID NO: 36          moltype = AA  length = 132
FEATURE                Location/Qualifiers
source                 1..132
                       mol_type = protein
                       organism = synthetic construct
SEQUENCE: 36
QVQLVESGGG LVQAGGSLRL SCAASGFTFD DYAITWFRQA PGKEREGVAY ISNSDGMTYY      60
ADSVKGRFTI SSDNAKNTVY LQMDSLKPED TAVYYCAAEG RMGTHSRDSV YFWAFSALYD     120
YWGQGTQVTV SS                                                         132

SEQ ID NO: 37          moltype = AA  length = 10
FEATURE                Location/Qualifiers
source                 1..10
                       mol_type = protein
                       organism = synthetic construct
SEQUENCE: 37
GFTFDDYAIT                                                             10

SEQ ID NO: 38          moltype = AA  length = 10
FEATURE                Location/Qualifiers
source                 1..10
                       mol_type = protein
                       organism = synthetic construct
SEQUENCE: 38
YISNNDGMTY                                                             10

SEQ ID NO: 39          moltype = AA  length = 23
FEATURE                Location/Qualifiers
source                 1..23
                       mol_type = protein
                       organism = synthetic construct
SEQUENCE: 39
EGRMGTHSRD SVYFWAFSAL YDY                                              23

SEQ ID NO: 40          moltype = AA  length = 132
FEATURE                Location/Qualifiers
source                 1..132
                       mol_type = protein
                       organism = synthetic construct
SEQUENCE: 40
QVQLVESGGG LVQAGGSLRL SCAASGFTFD DYAITWFRQA PGKEREGVAY ISNNDGMTYY      60
ADSVKGRFTI SSDNAKNPVY LQMDSLKPED TAVYYCAAEG RMGTHSRDSV YFWAFSALYD     120
YWGQGTQVTV SS                                                         132

SEQ ID NO: 41          moltype = AA  length = 10
FEATURE                Location/Qualifiers
source                 1..10
                       mol_type = protein
                       organism = synthetic construct
SEQUENCE: 41
GFTFGDYAIT                                                             10

SEQ ID NO: 42          moltype = AA  length = 10
FEATURE                Location/Qualifiers
source                 1..10
                       mol_type = protein
                       organism = synthetic construct
SEQUENCE: 42
YISNFDGMTY                                                             10

SEQ ID NO: 43          moltype = AA  length = 23
FEATURE                Location/Qualifiers
source                 1..23
                       mol_type = protein
                       organism = synthetic construct
SEQUENCE: 43
EGRMGTHSRD SVYFWAFSAL YDY                                              23

SEQ ID NO: 44          moltype = AA  length = 132
FEATURE                Location/Qualifiers
source                 1..132
                       mol_type = protein
                       organism = synthetic construct
SEQUENCE: 44
QVQLVESGGG LVQAGGSLRL SCAASGFTFG DYAITWFRQA PGKEREGVAY ISNFDGMTYY      60
ADSVKGRFTI SSDNAKNTVY LQMDSLKPED TAVYYCAAEG RMGTHSRDSV YFWAFSALYD     120
YWGQGTQVTV SS                                                         132
```

-continued

```
SEQ ID NO: 45              moltype = AA   length = 10
FEATURE                    Location/Qualifiers
source                     1..10
                           mol_type = protein
                           organism = synthetic construct
SEQUENCE: 45
GFIFDDYAIA                                                          10

SEQ ID NO: 46              moltype = AA   length = 10
FEATURE                    Location/Qualifiers
source                     1..10
                           mol_type = protein
                           organism = synthetic construct
SEQUENCE: 46
FISNSDGTAY                                                          10

SEQ ID NO: 47              moltype = AA   length = 23
FEATURE                    Location/Qualifiers
source                     1..23
                           mol_type = protein
                           organism = synthetic construct
SEQUENCE: 47
EGRMGTHSGD SVYFWSFSAL YDY                                           23

SEQ ID NO: 48              moltype = AA   length = 132
FEATURE                    Location/Qualifiers
source                     1..132
                           mol_type = protein
                           organism = synthetic construct
SEQUENCE: 48
QVQLVESGGG LVQAGGSLRL SCAASGFIFD DYAIAWFRQA PGKEREGVSF ISNSDGTAYY   60
ADSVKGRFTI SSDNAKNTVY LQMDSLKPDD TADYYCAAEG RMGTHSGDSV YFWSFSALYD  120
YWGQGTQVTV SS                                                      132

SEQ ID NO: 49              moltype = AA   length = 10
FEATURE                    Location/Qualifiers
source                     1..10
                           mol_type = protein
                           organism = synthetic construct
SEQUENCE: 49
GFNFDDYAIA                                                          10

SEQ ID NO: 50              moltype = AA   length = 10
FEATURE                    Location/Qualifiers
source                     1..10
                           mol_type = protein
                           organism = synthetic construct
SEQUENCE: 50
FISNSDGTAY                                                          10

SEQ ID NO: 51              moltype = AA   length = 23
FEATURE                    Location/Qualifiers
source                     1..23
                           mol_type = protein
                           organism = synthetic construct
SEQUENCE: 51
EGRMGTHSRD SVYFWSFSAL YDY                                           23

SEQ ID NO: 52              moltype = AA   length = 132
FEATURE                    Location/Qualifiers
source                     1..132
                           mol_type = protein
                           organism = synthetic construct
SEQUENCE: 52
QLQLVESGGG LVQAGGSLRL SCAASGFNFD DYAIAWFRQA PGKEREGVSF ISNSDGTAYY   60
ADSVKGRFTI SSDNAKNTVY LQMDSLKPDD TADYYCAAEG RMGTHSRDSV YFWSFSALYD  120
YWGQGTQVTV SS                                                      132

SEQ ID NO: 53              moltype = AA   length = 10
FEATURE                    Location/Qualifiers
source                     1..10
                           mol_type = protein
                           organism = synthetic construct
SEQUENCE: 53
GFSFDDYAIA                                                          10

SEQ ID NO: 54              moltype = AA   length = 10
FEATURE                    Location/Qualifiers
```

-continued

```
source                  1..10
                        mol_type = protein
                        organism = synthetic construct
SEQUENCE: 54
FISNSDGTAY                                                          10

SEQ ID NO: 55           moltype = AA  length = 23
FEATURE                 Location/Qualifiers
source                  1..23
                        mol_type = protein
                        organism = synthetic construct
SEQUENCE: 55
EGRMGTHSRD SVYFWSFSAL YDY                                           23

SEQ ID NO: 56           moltype = AA  length = 132
FEATURE                 Location/Qualifiers
source                  1..132
                        mol_type = protein
                        organism = synthetic construct
SEQUENCE: 56
QVQLVESGGG LVQAGGSLRL SCAASGFSFD DYAIAWFRQA PGKEREGVSF ISNSDGTAYY   60
ADSVKGRFTI SSDNAKNTVY LQMDSLKPDD TADYYCAAEG RMGTHSRDSV YFWSFSALYD   120
YWGQGTQVTV SS                                                       132

SEQ ID NO: 57           moltype = AA  length = 10
FEATURE                 Location/Qualifiers
source                  1..10
                        mol_type = protein
                        organism = synthetic construct
SEQUENCE: 57
GGTFERLAMG                                                          10

SEQ ID NO: 58           moltype = AA  length = 10
FEATURE                 Location/Qualifiers
source                  1..10
                        mol_type = protein
                        organism = synthetic construct
SEQUENCE: 58
FISNSDGTAY                                                          10

SEQ ID NO: 59           moltype = AA  length = 23
FEATURE                 Location/Qualifiers
source                  1..23
                        mol_type = protein
                        organism = synthetic construct
SEQUENCE: 59
EGRMGTHSRD SVYFWSFSAL YDY                                           23

SEQ ID NO: 60           moltype = AA  length = 132
FEATURE                 Location/Qualifiers
source                  1..132
                        mol_type = protein
                        organism = synthetic construct
SEQUENCE: 60
QLQLVESGGG LVQPGGSLRL SCVLSGGTFE RLAMGWFRQA PGKEREGVSF ISNSDGTAYY   60
ADSVKGRFTI SSDNAKNTVY LQMDSLKPDD TADYYCAAEG RMGTHSRDSV YFWSFSALYD   120
YWGQGTQVTV SA                                                       132

SEQ ID NO: 61           moltype = AA  length = 10
FEATURE                 Location/Qualifiers
source                  1..10
                        mol_type = protein
                        organism = synthetic construct
SEQUENCE: 61
GFTFDDYAIT                                                          10

SEQ ID NO: 62           moltype = AA  length = 10
FEATURE                 Location/Qualifiers
source                  1..10
                        mol_type = protein
                        organism = synthetic construct
SEQUENCE: 62
YISNNDHNTY                                                          10

SEQ ID NO: 63           moltype = AA  length = 23
FEATURE                 Location/Qualifiers
source                  1..23
                        mol_type = protein
                        organism = synthetic construct
```

-continued

```
SEQUENCE: 63
EGRMGTHSRE SSYFWTFPAL YDY                                              23

SEQ ID NO: 64             moltype = AA  length = 132
FEATURE                   Location/Qualifiers
source                    1..132
                          mol_type = protein
                          organism = synthetic construct
SEQUENCE: 64
QVQLVESGGG LVQAGGSLRL SCAASGFTFD DYAITWFRQA PGKEREGVSY ISNNDHNTYY      60
ADSVKGRFTI SSDNAKNTVY LQMDSLKPED TAVYYCAAEG RMGTHSRESS YFWTFPALYD      120
YWGQGTQVTV SS                                                         132

SEQ ID NO: 65             moltype = AA  length = 132
FEATURE                   Location/Qualifiers
source                    1..132
                          mol_type = protein
                          organism = synthetic construct
SEQUENCE: 65
QVQLLESGGG LVQPGGSLRL SCAASGFTFG DYAITWFRQA PGKGLEGVAY ISNFDGMTYY      60
ADSVKGRFTI SSDNSKNTVY LQMNSLRAED TAVYYCAAEG RMGTHSRDSV YFWAFSALYD      120
YWGQGTLVTV SS                                                         132

SEQ ID NO: 66             moltype = AA  length = 132
FEATURE                   Location/Qualifiers
source                    1..132
                          mol_type = protein
                          organism = synthetic construct
SEQUENCE: 66
EVQLLESGGG LVQPGGSLRL SCAASGFTFG DYAITWFRQA PGKGLEGVAY ISNFDGMTYY      60
ADSVKGRFTI SSDNSKNTVY LQMNSLRAED TAVYYCAAEG RMGTHSRDSV YFWAFSALYD      120
YWGQGTLVTV SS                                                         132

SEQ ID NO: 67             moltype = AA  length = 132
FEATURE                   Location/Qualifiers
source                    1..132
                          mol_type = protein
                          organism = synthetic construct
SEQUENCE: 67
QVQLLESGGG LVQPGGSLRL SCAASGFTFG DYAITWFRQA PGKGLEGVAY ISNFDGMTYY      60
ADSVKGRFTI SRDNSKNTVY LQMNSLRAED TAVYYCAAEG RMGTHSRDSV YFWAFSALYD      120
YWGQGTLVTV SS                                                         132

SEQ ID NO: 68             moltype = AA  length = 132
FEATURE                   Location/Qualifiers
source                    1..132
                          mol_type = protein
                          organism = synthetic construct
SEQUENCE: 68
EVQLLESGGG LVQPGGSLRL SCAASGFTFG DYAITWFRQA PGKGLEGVAY ISNFDGMTYY      60
ADSVKGRFTI SRDNSKNTVY LQMNSLRAED TAVYYCAAEG RMGTHSRDSV YFWAFSALYD      120
YWGQGTLVTV SS                                                         132

SEQ ID NO: 69             moltype = AA  length = 132
FEATURE                   Location/Qualifiers
source                    1..132
                          mol_type = protein
                          organism = synthetic construct
SEQUENCE: 69
EVQLLESGGG LVQAGGSLRL SCAASGFTFG DYAITWFRQA PGKGLEGVAY ISNFDGMTYY      60
ADSVKGRFTI SSDNSKNTVY LQMNSLRAED TAVYYCAAEG RMGTHSRDSV YFWAFSALYD      120
YWGQGTLVTV SS                                                         132

SEQ ID NO: 70             moltype = AA  length = 132
FEATURE                   Location/Qualifiers
source                    1..132
                          mol_type = protein
                          organism = synthetic construct
SEQUENCE: 70
EVQLLESGGG LVQPGGSLRL SCAASGFTFG DYAITWFRQA PGKELEGVAY ISNFDGMTYY      60
ADSVKGRFTI SSDNSKNTVY LQMNSLRAED TAVYYCAAEG RMGTHSRDSV YFWAFSALYD      120
YWGQGTLVTV SS                                                         132

SEQ ID NO: 71             moltype = AA  length = 132
FEATURE                   Location/Qualifiers
source                    1..132
                          mol_type = protein
                          organism = synthetic construct
SEQUENCE: 71
```

```
EVQLLESGGG LVQPGGSLRL SCAASGFTFG DYAITWFRQA PGKGREGVAY ISNFDGMTYY   60
ADSVKGRFTI SSDNSKNTVY LQMNSLRAED TAVYYCAAEG RMGTHSRDSV YFWAFSALYD  120
YWGQGTLVTV SS                                                      132

SEQ ID NO: 72            moltype = AA  length = 132
FEATURE                  Location/Qualifiers
source                   1..132
                         mol_type = protein
                         organism = synthetic construct
SEQUENCE: 72
EVQLLESGGG LVQPGGSLRL SCAASGFTFG DYAITWFRQA PGKEREGVAY ISNFDGMTYY   60
ADSVKGRFTI SSDNSKNTVY LQMNSLRAED TAVYYCAAEG RMGTHSRDSV YFWAFSALYD  120
YWGQGTLVTV SS                                                      132

SEQ ID NO: 73            moltype = AA  length = 132
FEATURE                  Location/Qualifiers
source                   1..132
                         mol_type = protein
                         organism = synthetic construct
SEQUENCE: 73
EVQLLESGGG LVQPGGSLRL SCAASGFTFG DYAITWFRQA PGKGLEGVAY ISNFDGMTYY   60
ADSVKGRFTI SSDNAKNTVY LQMNSLRAED TAVYYCAAEG RMGTHSRDSV YFWAFSALYD  120
YWGQGTLVTV SS                                                      132

SEQ ID NO: 74            moltype = AA  length = 132
FEATURE                  Location/Qualifiers
source                   1..132
                         mol_type = protein
                         organism = synthetic construct
SEQUENCE: 74
EVQLLESGGG LVQPGGSLRL SCAASGFTFG DYAITWFRQA PGKGLEGVAY ISNFDGMTYY   60
ADSVKGRFTI SSDNSKNTVY LQMDSLRAED TAVYYCAAEG RMGTHSRDSV YFWAFSALYD  120
YWGQGTLVTV SS                                                      132

SEQ ID NO: 75            moltype = AA  length = 132
FEATURE                  Location/Qualifiers
source                   1..132
                         mol_type = protein
                         organism = synthetic construct
SEQUENCE: 75
EVQLLESGGG LVQPGGSLRL SCAASGFTFG DYAITWFRQA PGKGLEGVAY ISNFDGMTYY   60
ADSVKGRFTI SSDNSKNTVY LQMNSLRPED TAVYYCAAEG RMGTHSRDSV YFWAFSALYD  120
YWGQGTLVTV SS                                                      132

SEQ ID NO: 76            moltype = AA  length = 132
FEATURE                  Location/Qualifiers
source                   1..132
                         mol_type = protein
                         organism = synthetic construct
SEQUENCE: 76
EVQLLESGGG LVQPGGSLRL SCAASGFTFG DYAITWFRQA PGKGLEGVSY ISNFDGMTYY   60
ADSVKGRFTI SSDNSKNTVY LQMNSLRAED TAVYYCAAEG RMGTHSRDSV YFWAFSALYD  120
YWGQGTLVTV SS                                                      132

SEQ ID NO: 77            moltype = AA  length = 132
FEATURE                  Location/Qualifiers
source                   1..132
                         mol_type = protein
                         organism = synthetic construct
SEQUENCE: 77
EVQLVESGGG LVQPGGSLRL SCAASGFTFG DYAITWFRQA PGKGLEGVAY ISNFDGMTYY   60
ADSVKGRFTI SSDNSKNTVY LQMNSLRAED TAVYYCAAEG RMGTHSRDSV YFWAFSALYD  120
YWGQGTLVTV SS                                                      132

SEQ ID NO: 78            moltype = AA  length = 132
FEATURE                  Location/Qualifiers
source                   1..132
                         mol_type = protein
                         organism = synthetic construct
SEQUENCE: 78
EVQLLESGGG LVQPGGSLRL SCAASGFTFG DYAITWVRQA PGKGLEGVAY ISNFDGMTYY   60
ADSVKGRFTI SSDNSKNTVY LQMNSLRAED TAVYYCAAEG RMGTHSRDSV YFWAFSALYD  120
YWGQGTLVTV SS                                                      132

SEQ ID NO: 79            moltype = AA  length = 10
FEATURE                  Location/Qualifiers
source                   1..10
                         mol_type = protein
                         organism = synthetic construct
```

```
SEQUENCE: 79
GRTFSNYAMG                                                      10

SEQ ID NO: 80          moltype = AA  length = 10
FEATURE                Location/Qualifiers
source                 1..10
                       mol_type = protein
                       organism = synthetic construct
SEQUENCE: 80
TISWNGGSTY                                                      10

SEQ ID NO: 81          moltype = AA  length = 19
FEATURE                Location/Qualifiers
source                 1..19
                       mol_type = protein
                       organism = synthetic construct
SEQUENCE: 81
RWLPVNQFLG VMRPSFVSA                                            19

SEQ ID NO: 82          moltype = AA  length = 128
FEATURE                Location/Qualifiers
source                 1..128
                       mol_type = protein
                       organism = synthetic construct
SEQUENCE: 82
QLQLVESGGG LVQAGGSLRL SCAASGRTFS NYAMGWFRQA PGKEREFVAT ISWNGGSTYY 60
EDSVKGRFTI SRDNSENTVD LQMNSLKPED TAVYYCAARW LPVNQFLGVM RPSFVSAWGQ 120
GTQVTVSS                                                        128

SEQ ID NO: 83          moltype = AA  length = 10
FEATURE                Location/Qualifiers
source                 1..10
                       mol_type = protein
                       organism = synthetic construct
SEQUENCE: 83
TRTFSHLAMG                                                      10

SEQ ID NO: 84          moltype = AA  length = 10
FEATURE                Location/Qualifiers
source                 1..10
                       mol_type = protein
                       organism = synthetic construct
SEQUENCE: 84
TISWGGDRTY                                                      10

SEQ ID NO: 85          moltype = AA  length = 17
FEATURE                Location/Qualifiers
source                 1..17
                       mol_type = protein
                       organism = synthetic construct
SEQUENCE: 85
DKLLFGWGSP PNTDFGS                                              17

SEQ ID NO: 86          moltype = AA  length = 126
FEATURE                Location/Qualifiers
source                 1..126
                       mol_type = protein
                       organism = synthetic construct
SEQUENCE: 86
QVQLVESGGG LVQAGGSLRL SCAASTRTFS HLAMGWFRQA VGKEREPVAT ISWGGDRTYY 60
ADSVKARFAI SRDNAKSTVY LQMNSLKPED TAIYYCAADK LLFGWGSPPN TDFGSWGQGT 120
QVTVSS                                                          126

SEQ ID NO: 87          moltype = AA  length = 11
FEATURE                Location/Qualifiers
source                 1..11
                       mol_type = protein
                       organism = synthetic construct
SEQUENCE: 87
GRRIFPLLTM G                                                    11

SEQ ID NO: 88          moltype = AA  length = 10
FEATURE                Location/Qualifiers
source                 1..10
                       mol_type = protein
                       organism = synthetic construct
SEQUENCE: 88
VIPRTGDSTY                                                      10
```

-continued

```
SEQ ID NO: 89              moltype = AA   length = 14
FEATURE                    Location/Qualifiers
source                     1..14
                           mol_type = protein
                           organism = synthetic construct
SEQUENCE: 89
RDGSSSPRPA DFGF                                                14

SEQ ID NO: 90              moltype = AA   length = 124
FEATURE                    Location/Qualifiers
source                     1..124
                           mol_type = protein
                           organism = synthetic construct
SEQUENCE: 90
QVQLVESGGG LVQAGDSLRL SCAVSGRRIF PLLTMGWFRQ NPGKDREFVA VIPRTGDSTY   60
YADSVKGRFA ISRDNAKNTV HLQMNSLKPE DTAVYYCAAR DGSSSPRPAD FGFWGQGTQV  120
TVSS                                                          124

SEQ ID NO: 91              moltype = AA   length = 10
FEATURE                    Location/Qualifiers
source                     1..10
                           mol_type = protein
                           organism = synthetic construct
SEQUENCE: 91
GFTFSNHWMY                                                     10

SEQ ID NO: 92              moltype = AA   length = 10
FEATURE                    Location/Qualifiers
source                     1..10
                           mol_type = protein
                           organism = synthetic construct
SEQUENCE: 92
DISPGGISTR                                                     10

SEQ ID NO: 93              moltype = AA   length = 16
FEATURE                    Location/Qualifiers
source                     1..16
                           mol_type = protein
                           organism = synthetic construct
SEQUENCE: 93
GRAYVAGVSR ASQYVY                                              16

SEQ ID NO: 94              moltype = AA   length = 125
FEATURE                    Location/Qualifiers
source                     1..125
                           mol_type = protein
                           organism = synthetic construct
SEQUENCE: 94
QLQLVESGGD LVQPGGSLRL SCLASGFTFS NHWMYWLRQA PGKGLEWVSD ISPGGISTRY   60
ADSVKGRFTI SRDNAKNTVY LEMSSLKPLD TAVYYCAAGR AYVAGVSRAS QYVYWGQGTQ  120
VTVSS                                                         125

SEQ ID NO: 95              moltype = AA   length = 10
FEATURE                    Location/Qualifiers
source                     1..10
                           mol_type = protein
                           organism = synthetic construct
SEQUENCE: 95
GRTFSHYTVG                                                     10

SEQ ID NO: 96              moltype = AA   length = 9
FEATURE                    Location/Qualifiers
source                     1..9
                           mol_type = protein
                           organism = synthetic construct
SEQUENCE: 96
GLSWNHRTK                                                      9

SEQ ID NO: 97              moltype = AA   length = 15
FEATURE                    Location/Qualifiers
source                     1..15
                           mol_type = protein
                           organism = synthetic construct
SEQUENCE: 97
DVSPFITTIQ TDMEY                                               15

SEQ ID NO: 98              moltype = AA   length = 123
FEATURE                    Location/Qualifiers
source                     1..123
```

```
                              mol_type = protein
                              organism = synthetic construct
SEQUENCE: 98
QLQLVESGGG LVQPGGSLRL SCAASGRTFS HYTVGWFRQA PGKEREFVAG LSWNHRTKYA   60
DSVKGRFTIS VDNAKNTVYL QMNSLKPEDT AVYVCTADVS PFITTIQTDM EYWGKGTLVT   120
VSS                                                                 123

SEQ ID NO: 99                 moltype = AA  length = 10
FEATURE                       Location/Qualifiers
source                        1..10
                              mol_type = protein
                              organism = synthetic construct
SEQUENCE: 99
GIIFSKHGMG                                                          10

SEQ ID NO: 100                moltype = AA  length = 9
FEATURE                       Location/Qualifiers
source                        1..9
                              mol_type = protein
                              organism = synthetic construct
SEQUENCE: 100
RITSGGSTS                                                           9

SEQ ID NO: 101                moltype = AA  length = 15
FEATURE                       Location/Qualifiers
source                        1..15
                              mol_type = protein
                              organism = synthetic construct
SEQUENCE: 101
ERFIINVEGA GRGPY                                                    15

SEQ ID NO: 102                moltype = AA  length = 123
FEATURE                       Location/Qualifiers
source                        1..123
                              mol_type = protein
                              organism = synthetic construct
SEQUENCE: 102
QLQLVESGGG LVQSGGSLRL SCTTSGIIFS KHGMGWYRQA PGAQRELVAR ITSGGSTSYA   60
DSGKGRFTIS RDNTKNTLYL QMNSLEPEDT AVYYCNVERF IINVEGAGRG PYWGQGTLVT   120
VSS                                                                 123

SEQ ID NO: 103                moltype = AA  length = 10
FEATURE                       Location/Qualifiers
source                        1..10
                              mol_type = protein
                              organism = synthetic construct
SEQUENCE: 103
GRTFSTLNMG                                                          10

SEQ ID NO: 104                moltype = AA  length = 10
FEATURE                       Location/Qualifiers
source                        1..10
                              mol_type = protein
                              organism = synthetic construct
SEQUENCE: 104
NIGWSGGTTY                                                          10

SEQ ID NO: 105                moltype = AA  length = 16
FEATURE                       Location/Qualifiers
source                        1..16
                              mol_type = protein
                              organism = synthetic construct
SEQUENCE: 105
DIKGLYFPRD ARSFDY                                                   16

SEQ ID NO: 106                moltype = AA  length = 125
FEATURE                       Location/Qualifiers
source                        1..125
                              mol_type = protein
                              organism = synthetic construct
SEQUENCE: 106
QVQLVESGGG LVQAGGSLRL SCAVSGRTFS TLNMGWFRQA PGKEREFVAN IGWSGGTTYS   60
SDSAKGRFTI SRDNAENTVY LQMNSLKPED TAVYYCAADI KGLYFPRDAR SFDYWGQGTQ   120
VTVSS                                                               125

SEQ ID NO: 107                moltype = AA  length = 10
FEATURE                       Location/Qualifiers
source                        1..10
                              mol_type = protein
```

-continued

```
                         organism = synthetic construct
SEQUENCE: 107
GRIFPIYHMG                                                      10

SEQ ID NO: 108          moltype = AA   length = 10
FEATURE                 Location/Qualifiers
source                  1..10
                        mol_type = protein
                        organism = synthetic construct
SEQUENCE: 108
AIRRSDSMTN                                                      10

SEQ ID NO: 109          moltype = AA   length = 14
FEATURE                 Location/Qualifiers
source                  1..14
                        mol_type = protein
                        organism = synthetic construct
SEQUENCE: 109
ALGQYYGANT QYDS                                                 14

SEQ ID NO: 110          moltype = AA   length = 123
FEATURE                 Location/Qualifiers
source                  1..123
                        mol_type = protein
                        organism = synthetic construct
SEQUENCE: 110
QLQLVESGGG LVQAGGSLRL SCAASGRIFP IYHMGWFRQA PGKEREFVAA IRRSDSMTNY 60
ADSVKGRFTI SRDNAKNTLF LQMNSLRPED TGVYNCAAAL GQYYGANTQY DSWGQGTQVT 120
VSS                                                             123

SEQ ID NO: 111          moltype = AA   length = 10
FEATURE                 Location/Qualifiers
source                  1..10
                        mol_type = protein
                        organism = synthetic construct
SEQUENCE: 111
GSIFRFNLMG                                                      10

SEQ ID NO: 112          moltype = AA   length = 9
FEATURE                 Location/Qualifiers
source                  1..9
                        mol_type = protein
                        organism = synthetic construct
SEQUENCE: 112
VMSEGGTTN                                                       9

SEQ ID NO: 113          moltype = AA   length = 11
FEATURE                 Location/Qualifiers
source                  1..11
                        mol_type = protein
                        organism = synthetic construct
SEQUENCE: 113
WGSNSGPVLQ Y                                                    11

SEQ ID NO: 114          moltype = AA   length = 119
FEATURE                 Location/Qualifiers
source                  1..119
                        mol_type = protein
                        organism = synthetic construct
SEQUENCE: 114
QLQLVESGGG LVQPGGSLRL SCAASGSIFR FNLMGWYRQA PGKQRELVAV MSEGGTTNYG 60
DSVKGRFTMS RDNAKNTVYL QMNSLKSEDT AVYYCNFWGS NSGPVLQYWG QGTQVTVSS 119

SEQ ID NO: 115          moltype = AA   length = 10
FEATURE                 Location/Qualifiers
source                  1..10
                        mol_type = protein
                        organism = synthetic construct
SEQUENCE: 115
GRIFVISNAG                                                      10

SEQ ID NO: 116          moltype = AA   length = 10
FEATURE                 Location/Qualifiers
source                  1..10
                        mol_type = protein
                        organism = synthetic construct
SEQUENCE: 116
SISRHGEITN                                                      10
```

-continued

```
SEQ ID NO: 117          moltype = AA   length = 15
FEATURE                 Location/Qualifiers
source                  1..15
                        mol_type = protein
                        organism = synthetic construct
SEQUENCE: 117
TLGHSPRTDP GDFDS                                                      15

SEQ ID NO: 118          moltype = AA   length = 124
FEATURE                 Location/Qualifiers
source                  1..124
                        mol_type = protein
                        organism = synthetic construct
SEQUENCE: 118
QVQLVESGGG SVQPGGSLRL ACAASGRIFV ISNAGWFRQT PGKEREFVAS ISRHGEITNY     60
ADAVKGRFTI SRDNSKNMMY LQMNSLNFED TAVYYCATTL GHSPRTDPGD FDSWGQGTQV    120
TVSS                                                                 124

SEQ ID NO: 119          moltype = AA   length = 10
FEATURE                 Location/Qualifiers
source                  1..10
                        mol_type = protein
                        organism = synthetic construct
SEQUENCE: 119
GSIFRINTMG                                                            10

SEQ ID NO: 120          moltype = AA   length = 9
FEATURE                 Location/Qualifiers
source                  1..9
                        mol_type = protein
                        organism = synthetic construct
SEQUENCE: 120
SFTSGGSPN                                                              9

SEQ ID NO: 121          moltype = AA   length = 15
FEATURE                 Location/Qualifiers
source                  1..15
                        mol_type = protein
                        organism = synthetic construct
SEQUENCE: 121
YIMAWSHGVL KGYDS                                                      15

SEQ ID NO: 122          moltype = AA   length = 123
FEATURE                 Location/Qualifiers
source                  1..123
                        mol_type = protein
                        organism = synthetic construct
SEQUENCE: 122
QVQLVESGGG LVQPGGSLRL SCAASGSIFR INTMGWYRQA PGKQRELVAS FTSGGSPNYA     60
DSVKGRFTIS RDNAKNTVYL QMNSLRPEET AVYYCNAYIM AWSHGVLKGY DSWGQGTQVT    120
VSS                                                                  123

SEQ ID NO: 123          moltype = AA   length = 10
FEATURE                 Location/Qualifiers
source                  1..10
                        mol_type = protein
                        organism = synthetic construct
SEQUENCE: 123
GSIRTVNYMG                                                            10

SEQ ID NO: 124          moltype = AA   length = 9
FEATURE                 Location/Qualifiers
source                  1..9
                        mol_type = protein
                        organism = synthetic construct
SEQUENCE: 124
VVTSGGGTN                                                              9

SEQ ID NO: 125          moltype = AA   length = 13
FEATURE                 Location/Qualifiers
source                  1..13
                        mol_type = protein
                        organism = synthetic construct
SEQUENCE: 125
AASTYSSTVV RSF                                                        13

SEQ ID NO: 126          moltype = AA   length = 121
FEATURE                 Location/Qualifiers
source                  1..121
```

```
                              mol_type = protein
                              organism = synthetic construct
SEQUENCE: 126
QVQLVESGGG LVQPGESLRL SCAASGSIRT VNYMGWHRQA PGKQRELVAV VTSGGGTNYA   60
DSVKGRFTIS RDDTKNTVYL AMNSLKPEDT AVYYCNAAAS TYSSTVVRSF WGQGTQVTVS   120
S                                                                  121

SEQ ID NO: 127              moltype = AA  length = 10
FEATURE                     Location/Qualifiers
source                      1..10
                            mol_type = protein
                            organism = synthetic construct
SEQUENCE: 127
GSIFRINSMG                                                         10

SEQ ID NO: 128              moltype = AA  length = 10
FEATURE                     Location/Qualifiers
source                      1..10
                            mol_type = protein
                            organism = synthetic construct
SEQUENCE: 128
TFTTSGGVTN                                                         10

SEQ ID NO: 129              moltype = AA  length = 15
FEATURE                     Location/Qualifiers
source                      1..15
                            mol_type = protein
                            organism = synthetic construct
SEQUENCE: 129
YVMAWSRGVL KGYDS                                                   15

SEQ ID NO: 130              moltype = AA  length = 124
FEATURE                     Location/Qualifiers
source                      1..124
                            mol_type = protein
                            organism = synthetic construct
SEQUENCE: 130
QVQLVESGGG LVQPGGSLRL SCAASGSIFR INSMGWYRQA PGKQRELVAT FTTSGGVTNY   60
ADSVKGRFTI SRDNAKNTVY LQMNNLTPEE TAVYYCNAYV MAWSRGVLKG YDSWGQGTQV   120
TVSS                                                               124

SEQ ID NO: 131              moltype = AA  length = 10
FEATURE                     Location/Qualifiers
source                      1..10
                            mol_type = protein
                            organism = synthetic construct
SEQUENCE: 131
GRTFSGYRMG                                                         10

SEQ ID NO: 132              moltype = AA  length = 10
FEATURE                     Location/Qualifiers
source                      1..10
                            mol_type = protein
                            organism = synthetic construct
SEQUENCE: 132
SIRWIGPATA                                                         10

SEQ ID NO: 133              moltype = AA  length = 14
FEATURE                     Location/Qualifiers
source                      1..14
                            mol_type = protein
                            organism = synthetic construct
SEQUENCE: 133
DPTPSIDYKR GYDY                                                    14

SEQ ID NO: 134              moltype = AA  length = 123
FEATURE                     Location/Qualifiers
source                      1..123
                            mol_type = protein
                            organism = synthetic construct
SEQUENCE: 134
QVQLVESGGG LVQAGGSLRL SCAASGRTFS GYRMGWFRQA PGKEREFVAS IRWIGPATAY   60
ADSVKGRFTI SRDNAKNTVY LQMNSLKSED TAVYYCAADP TPSIDYKRGY DYWGQGTQVT   120
VSS                                                                123

SEQ ID NO: 135              moltype = AA  length = 10
FEATURE                     Location/Qualifiers
source                      1..10
                            mol_type = protein
```

-continued

```
                        organism = synthetic construct
SEQUENCE: 135
GRTFNTFRTG                                               10

SEQ ID NO: 136          moltype = AA  length = 10
FEATURE                 Location/Qualifiers
source                  1..10
                        mol_type = protein
                        organism = synthetic construct
SEQUENCE: 136
SLNWSSTWTS                                               10

SEQ ID NO: 137          moltype = AA  length = 15
FEATURE                 Location/Qualifiers
source                  1..15
                        mol_type = protein
                        organism = synthetic construct
SEQUENCE: 137
GIAGTPVMRA TSYIY                                         15

SEQ ID NO: 138          moltype = AA  length = 124
FEATURE                 Location/Qualifiers
source                  1..124
                        mol_type = protein
                        organism = synthetic construct
SEQUENCE: 138
QVQLVESGGG LVQPGGSLRV SCAASGRTFN TFRTGWFRQA PGKEREFVAS LNWSSTWTSY  60
ADSVKGRFSI SRDSAKNTVY LQMNSLKPED TADYYCAVGI AGTPVMRATS YIYWGQGTQV 120
TVSS                                                             124

SEQ ID NO: 139          moltype = AA  length = 10
FEATURE                 Location/Qualifiers
source                  1..10
                        mol_type = protein
                        organism = synthetic construct
SEQUENCE: 139
RFIFPIYAMG                                               10

SEQ ID NO: 140          moltype = AA  length = 10
FEATURE                 Location/Qualifiers
source                  1..10
                        mol_type = protein
                        organism = synthetic construct
SEQUENCE: 140
GIERTTDTTL                                               10

SEQ ID NO: 141          moltype = AA  length = 14
FEATURE                 Location/Qualifiers
source                  1..14
                        mol_type = protein
                        organism = synthetic construct
SEQUENCE: 141
RNSRRIGDVN DVDY                                          14

SEQ ID NO: 142          moltype = AA  length = 123
FEATURE                 Location/Qualifiers
source                  1..123
                        mol_type = protein
                        organism = synthetic construct
SEQUENCE: 142
QVQLVESGGG LVQPGGSLRL SCAASRFIFP IYAMGWFRQA PGKEREFVAG IERTTDTTLY  60
ADSVKGRFTI SRDNAKNTVY LQMYSLKPED AAVYYCAARN SRRIGDVNDV DYWGQGTQVT 120
VSS                                                              123

SEQ ID NO: 143          moltype = AA  length = 10
FEATURE                 Location/Qualifiers
source                  1..10
                        mol_type = protein
                        organism = synthetic construct
SEQUENCE: 143
RTIFPLYAMG                                               10

SEQ ID NO: 144          moltype = AA  length = 10
FEATURE                 Location/Qualifiers
source                  1..10
                        mol_type = protein
                        organism = synthetic construct
SEQUENCE: 144
GISRTTSTTL                                               10
```

-continued

```
SEQ ID NO: 145          moltype = AA  length = 14
FEATURE                 Location/Qualifiers
source                  1..14
                        mol_type = protein
                        organism = synthetic construct
SEQUENCE: 145
RNSRTIGDVN DVDY                                              14

SEQ ID NO: 146          moltype = AA  length = 123
FEATURE                 Location/Qualifiers
source                  1..123
                        mol_type = protein
                        organism = synthetic construct
SEQUENCE: 146
QLQLVESGGG LVQAGGSLRL SCAASRTIFP LYAMGWFRQA PGKEREFVAG ISRTTSTTLY 60
ADSVKGRFTI SRDNAANTVY LQMNTLKPED AAVYYCAARN SRTIGDVNDV DYWGQGTQLT 120
VSS                                                         123

SEQ ID NO: 147          moltype = AA  length = 10
FEATURE                 Location/Qualifiers
source                  1..10
                        mol_type = protein
                        organism = synthetic construct
SEQUENCE: 147
GRTISIYMMG                                                  10

SEQ ID NO: 148          moltype = AA  length = 10
FEATURE                 Location/Qualifiers
source                  1..10
                        mol_type = protein
                        organism = synthetic construct
SEQUENCE: 148
AIMPSGSRTY                                                  10

SEQ ID NO: 149          moltype = AA  length = 15
FEATURE                 Location/Qualifiers
source                  1..15
                        mol_type = protein
                        organism = synthetic construct
SEQUENCE: 149
KLFRGSGDYI NDYDH                                            15

SEQ ID NO: 150          moltype = AA  length = 124
FEATURE                 Location/Qualifiers
source                  1..124
                        mol_type = protein
                        organism = synthetic construct
SEQUENCE: 150
QVQLVESGGG LVQAGGSLRL SCAASGRTIS IYMMGWFRQA PGKGREFVSA IMPSGSRTYS 60
ADWVKGRFTI SRDNSKSTVY LQMNSLKPED TAVYYCAAKL FRGSGDYIND YDHWGQGTQV 120
TVSS                                                        124

SEQ ID NO: 151          moltype = AA  length = 121
FEATURE                 Location/Qualifiers
source                  1..121
                        mol_type = protein
                        organism = synthetic construct
SEQUENCE: 151
QVQLVESGGG LVQPGGSLRL SCAASGSIRT VNYMGWHRQA PGKQRELVAV VTSGGGTNYA 60
DSVKGRFTIS RDDTKNTVYL QMNSLRAEDT AVYYCNAAAS TYSSTVVRSF WGQGTLVTVS 120
S                                                           121

SEQ ID NO: 152          moltype = AA  length = 121
FEATURE                 Location/Qualifiers
source                  1..121
                        mol_type = protein
                        organism = synthetic construct
SEQUENCE: 152
QVQLVESGGG LVQPGGSLRL SCAASGSIRT VNYMGWHRQA PGKQRELVAV VTSGGGTNYA 60
DSVKGRFTIS RDNTKNTVYL QMNSLRAEDT AVYYCNAAAS TYSSTVVRSF WGQGTLVTVS 120
S                                                           121

SEQ ID NO: 153          moltype = AA  length = 121
FEATURE                 Location/Qualifiers
source                  1..121
                        mol_type = protein
                        organism = synthetic construct
SEQUENCE: 153
```

```
QVQLVESGGG LVQPGGSLRL SCAASGSIRT VNYMGWHRQA PGKQRELVAV VTSGGGTNYA  60
DSVKGRFTIS RDDSKNTVYL QMNSLRAEDT AVYYCNAAAS TYSSTVVRSF WGQGTLVTVS  120
S                                                                 121

SEQ ID NO: 154          moltype = AA   length = 121
FEATURE                 Location/Qualifiers
source                  1..121
                        mol_type = protein
                        organism = synthetic construct
SEQUENCE: 154
QVQLVESGGG LVQPGGSLRL SCAASGSIRT VNYMGWHRQA PGKQRELVAV VTSGGGTNYA  60
DSVKGRFTIS RDNSKNTVYL QMNSLRAEDT AVYYCNAAAS TYSSTVVRSF WGQGTLVTVS  120
S                                                                 121

SEQ ID NO: 155          moltype = AA   length = 121
FEATURE                 Location/Qualifiers
source                  1..121
                        mol_type = protein
                        organism = synthetic construct
SEQUENCE: 155
QVQLVESGGG LVQPGGSLRL SCAASGSIRT VNYMGWHRQA PGKGRELVAV VTSGGGTNYA  60
DSVKGRFTIS RDDTKNTVYL QMNSLRAEDT AVYYCNAAAS TYSSTVVRSF WGQGTLVTVS  120
S                                                                 121

SEQ ID NO: 156          moltype = AA   length = 121
FEATURE                 Location/Qualifiers
source                  1..121
                        mol_type = protein
                        organism = synthetic construct
SEQUENCE: 156
QVQLVESGGG LVQPGGSLRL SCAASGSIRT VNYMGWHRQA PGKQLELVAV VTSGGGTNYA  60
DSVKGRFTIS RDDTKNTVYL QMNSLRAEDT AVYYCNAAAS TYSSTVVRSF WGQGTLVTVS  120
S                                                                 121

SEQ ID NO: 157          moltype = AA   length = 121
FEATURE                 Location/Qualifiers
source                  1..121
                        mol_type = protein
                        organism = synthetic construct
SEQUENCE: 157
EVQLVESGGG LVQPGGSLRL SCAASGSIRT VNYMGWHRQA PGKQRELVAV VTSGGGTNYA  60
DSVKGRFTIS RDDTKNTVYL QMNSLRAEDT AVYYCNAAAS TYSSTVVRSF WGQGTLVTVS  120
S                                                                 121

SEQ ID NO: 158          moltype = AA   length = 121
FEATURE                 Location/Qualifiers
source                  1..121
                        mol_type = protein
                        organism = synthetic construct
SEQUENCE: 158
QVQLVESGGG LVQPGGSLRL SCAASGSIRT VNYMGWHRQA PGKQRELVSV VTSGGGTNYA  60
DSVKGRFTIS RDDTKNTVYL QMNSLRAEDT AVYYCNAAAS TYSSTVVRSF WGQGTLVTVS  120
S                                                                 121

SEQ ID NO: 159          moltype = AA   length = 232
FEATURE                 Location/Qualifiers
source                  1..232
                        mol_type = protein
                        organism = synthetic construct
SEQUENCE: 159
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 160          moltype = AA   length = 232
FEATURE                 Location/Qualifiers
source                  1..232
                        mol_type = protein
                        organism = synthetic construct
SEQUENCE: 160
EPKSADKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 161          moltype = AA   length = 347
FEATURE                 Location/Qualifiers
source                  1..347
```

```
                              mol_type = protein
                              organism = synthetic construct
SEQUENCE: 161
QVQLVESGGG LVQPGGSLTL SCVAAGSNFS LYAMSYYRQV PGKQRELVAR IRDNGRTNYA    60
DSVKDRFTIS RDSAKNTVYL QMHSLKPEDT AVYYCNADNR VTTFWGRGTQ VTVSSEPKSA   120
DKTHTCPPCP APEAAGGPSV FLFPPKPKDT LMISRTPEVT CVVVDVSHED PEVKFNWYVD   180
GVEVHNAKTK PREEQYNSTY RVVSVLTVLH QDWLNGKEYK CKVSNKALPA PIEKTISKAK   240
GQPREPQVYT LPPSREEMTK NQVSLTCLVK GFYPSDIAVE WESNGQPENN YKTTPPVLDS   300
DGSFFLYSKL TVDKSRWQQG NVFSCSVMHE ALHNHYTQKS LSLSPGK              347

SEQ ID NO: 162          moltype = AA   length = 347
FEATURE                 Location/Qualifiers
source                  1..347
                        mol_type = protein
                        organism = synthetic construct
SEQUENCE: 162
QLQLVESGGG LVQPGGSLRL SCAASGSIFS IDAMGWYRQA PGKERELVAA IGSGTYYADS    60
VKGRFTISRD NAKKNTLYLQ MDSLKPEDTA IYYCASGDSY PDEYWGQGTQ VTVSAEPKSA   120
DKTHTCPPCP APEAAGGPSV FLFPPKPKDT LMISRTPEVT CVVVDVSHED PEVKFNWYVD   180
GVEVHNAKTK PREEQYNSTY RVVSVLTVLH QDWLNGKEYK CKVSNKALPA PIEKTISKAK   240
GQPREPQVYT LPPSREEMTK NQVSLTCLVK GFYPSDIAVE WESNGQPENN YKTTPPVLDS   300
DGSFFLYSKL TVDKSRWQQG NVFSCSVMHE ALHNHYTQKS LSLSPGK              347

SEQ ID NO: 163          moltype = AA   length = 349
FEATURE                 Location/Qualifiers
source                  1..349
                        mol_type = protein
                        organism = synthetic construct
SEQUENCE: 163
QLQLVESGGG LVQPGGSLRL SCAASESDFS IYIMGWYRQA PGKQRELVVT ITPGGNTNYV    60
DSVKGRFTIS RDNTMNTAYL QMNSLKPDDT AVYYCNARNI FRNVDYSGKG TLVTVSSEPK   120
SADKTHTCPP CPAPEAAGGP SVFLFPPKPK DTLMISRTPE VTCVVVDVSH EDPEVKFNWY   180
VDGVEVHNAK TKPREEQYNS TYRVVSVLTV LHQDWLNGKE YKCKVSNKAL PAPIEKTISK   240
AKGQPREPQV YTLPPSREEM TKNQVSLTCL VKGFYPSDIA VEWESNGQPE NNYKTTPPVL   300
DSDGSFFLYS KLTVDKSRWQ QGNVFSCSVM HEALHNHYTQ KSLSLSPGK           349

SEQ ID NO: 164          moltype = AA   length = 349
FEATURE                 Location/Qualifiers
source                  1..349
                        mol_type = protein
                        organism = synthetic construct
SEQUENCE: 164
QVQLVESGGG LVQPGGSLRL SCVASGIEFS IYIMGWYRQA PGKQRELVAT VTPGGNTNYA    60
DSVKGRFTIS RDNTKNTAYL QMNSLKPDDT AVYYCNARNI FRNMDYQGKG TLVTVSSEPK   120
SADKTHTCPP CPAPEAAGGP SVFLFPPKPK DTLMISRTPE VTCVVVDVSH EDPEVKFNWY   180
VDGVEVHNAK TKPREEQYNS TYRVVSVLTV LHQDWLNGKE YKCKVSNKAL PAPIEKTISK   240
AKGQPREPQV YTLPPSREEM TKNQVSLTCL VKGFYPSDIA VEWESNGQPE NNYKTTPPVL   300
DSDGSFFLYS KLTVDKSRWQ QGNVFSCSVM HEALHNHYTQ KSLSLSPGK           349

SEQ ID NO: 165          moltype = AA   length = 349
FEATURE                 Location/Qualifiers
source                  1..349
                        mol_type = protein
                        organism = synthetic construct
SEQUENCE: 165
QVQLVESGGG SVQPGGSLRL SCAASGSDFN IYIMGWYQQA PGKQRELVAT ITPGGNTNYV    60
DSVKGRFTIS RDNTKNTAYL QMNSLKPDDT AVYYCNARNI FRYMDYWGKG TLVTVSSEPK   120
SADKTHTCPP CPAPEAAGGP SVFLFPPKPK DTLMISRTPE VTCVVVDVSH EDPEVKFNWY   180
VDGVEVHNAK TKPREEQYNS TYRVVSVLTV LHQDWLNGKE YKCKVSNKAL PAPIEKTISK   240
AKGQPREPQV YTLPPSREEM TKNQVSLTCL VKGFYPSDIA VEWESNGQPE NNYKTTPPVL   300
DSDGSFFLYS KLTVDKSRWQ QGNVFSCSVM HEALHNHYTQ KSLSLSPGK           349

SEQ ID NO: 166          moltype = AA   length = 364
FEATURE                 Location/Qualifiers
source                  1..364
                        mol_type = protein
                        organism = synthetic construct
SEQUENCE: 166
QVQLVESGGG LVQAGGSLRL SCAASGFIFD DYAIAWFRQA PGKEREGVSF ISNSDGTAYY    60
ADSVKGRFTI SSDNAKNTVY LQMDSLKPDD TADYYCAAEG RMGTHSRDSV YFWAFSALYD   120
YWGQGTQVTV SSEPKSADKT HTCPPCPAPE AAGGPSVFLF PPKPKDTLMI SRTPEVTCVV   180
VDVSHEDPEV KFNWYVDGVE VHNAKTKPRE EQYNSTYRVV SVLTVLHQDW LNGKEYKCKV   240
SNKALPAPIE KTISKAKGQP REPQVYTLPP SREEMTKNQV SLTCLVKGFY PSDIAVEWES   300
NGQPENNYKT TPPVLDSDGS FFLYSKLTVD KSRWQQGNVF SCSVMHEALH NHYTQKSLSL   360
SPGK                                                        364

SEQ ID NO: 167          moltype = AA   length = 364
FEATURE                 Location/Qualifiers
source                  1..364
```

-continued

```
                              mol_type = protein
                              organism = synthetic construct
SEQUENCE: 167
QLQLVESGGG LVQAGGSLRL SCAASGFTFD DYAITWFRQA PGKEREGVAY ISNSDGMTYY     60
VDSVKGRFTI SSDNAKNTVY LQMDSLKPED TAVYYCAAEG IMGTHNRDNV YFWAFSALYD    120
YWGQGTQVTV SSEPKSADKT HTCPPCPAPE AAGGPSVFLF PPKPKDTLMI SRTPEVTCVV    180
VDVSHEDPEV KFNWYVDGVE VHNAKTKPRE EQYNSTYRVV SVLTVLHQDW LNGKEYKCKV    240
SNKALPAPIE KTISKAKGQP REPQVYTLPP SREEMTKNQV SLTCLVKGFY PSDIAVEWES    300
NGQPENNYKT TPPVLDSDGS FFLYSKLTVD KSRWQQGNVF SCSVMHEALH NHYTQKSLSL    360
SPGK                                                                364

SEQ ID NO: 168          moltype = AA  length = 364
FEATURE                 Location/Qualifiers
source                  1..364
                        mol_type = protein
                        organism = synthetic construct
SEQUENCE: 168
QVQLVESGGG LVQAGGSLRL SCAASGFTFD DYAITWFRQA PGKEREGVAY ISNFDGMTYY     60
ADSVKGRFTI SSDNAKNTVY LQMDSLKPED TAVYYCAAEG RMGTHSRDSV YFWAFSALYD    120
HWGQGTQVTV SSEPKSADKT HTCPPCPAPE AAGGPSVFLF PPKPKDTLMI SRTPEVTCVV    180
VDVSHEDPEV KFNWYVDGVE VHNAKTKPRE EQYNSTYRVV SVLTVLHQDW LNGKEYKCKV    240
SNKALPAPIE KTISKAKGQP REPQVYTLPP SREEMTKNQV SLTCLVKGFY PSDIAVEWES    300
NGQPENNYKT TPPVLDSDGS FFLYSKLTVD KSRWQQGNVF SCSVMHEALH NHYTQKSLSL    360
SPGK                                                                364

SEQ ID NO: 169          moltype = AA  length = 364
FEATURE                 Location/Qualifiers
source                  1..364
                        mol_type = protein
                        organism = synthetic construct
SEQUENCE: 169
QVQLVESGGG LVQAGGSLRL SCAASGFTFD DYAITWFRQA PGKEREGVAY ISNSDGMTYY     60
ADSVKGRFTI SSDNAKNTVY LQMDSLKPED TAVYYCAAEG RMGTHSRDSV YFWAFSALYD    120
YWGQGTQVTV SSEPKSADKT HTCPPCPAPE AAGGPSVFLF PPKPKDTLMI SRTPEVTCVV    180
VDVSHEDPEV KFNWYVDGVE VHNAKTKPRE EQYNSTYRVV SVLTVLHQDW LNGKEYKCKV    240
SNKALPAPIE KTISKAKGQP REPQVYTLPP SREEMTKNQV SLTCLVKGFY PSDIAVEWES    300
NGQPENNYKT TPPVLDSDGS FFLYSKLTVD KSRWQQGNVF SCSVMHEALH NHYTQKSLSL    360
SPGK                                                                364

SEQ ID NO: 170          moltype = AA  length = 364
FEATURE                 Location/Qualifiers
source                  1..364
                        mol_type = protein
                        organism = synthetic construct
SEQUENCE: 170
QVQLVESGGG LVQAGGSLRL SCAASGFTFD DYAITWFRQA PGKEREGVAY ISNNDGMTYY     60
ADSVKGRFTI SSDNAKNPVY LQMDSLKPED TAVYYCAAEG RMGTHSRDSV YFWAFSALYD    120
YWGQGTQVTV SSEPKSADKT HTCPPCPAPE AAGGPSVFLF PPKPKDTLMI SRTPEVTCVV    180
VDVSHEDPEV KFNWYVDGVE VHNAKTKPRE EQYNSTYRVV SVLTVLHQDW LNGKEYKCKV    240
SNKALPAPIE KTISKAKGQP REPQVYTLPP SREEMTKNQV SLTCLVKGFY PSDIAVEWES    300
NGQPENNYKT TPPVLDSDGS FFLYSKLTVD KSRWQQGNVF SCSVMHEALH NHYTQKSLSL    360
SPGK                                                                364

SEQ ID NO: 171          moltype = AA  length = 364
FEATURE                 Location/Qualifiers
source                  1..364
                        mol_type = protein
                        organism = synthetic construct
SEQUENCE: 171
QVQLVESGGG LVQAGGSLRL SCAASGFTFG DYAITWFRQA PGKEREGVAY ISNFDGMTYY     60
ADSVKGRFTI SSDNAKNTVY LQMDSLKPED TAVYYCAAEG RMGTHSRDSV YFWAFSALYD    120
YWGQGTQVTV SSEPKSADKT HTCPPCPAPE AAGGPSVFLF PPKPKDTLMI SRTPEVTCVV    180
VDVSHEDPEV KFNWYVDGVE VHNAKTKPRE EQYNSTYRVV SVLTVLHQDW LNGKEYKCKV    240
SNKALPAPIE KTISKAKGQP REPQVYTLPP SREEMTKNQV SLTCLVKGFY PSDIAVEWES    300
NGQPENNYKT TPPVLDSDGS FFLYSKLTVD KSRWQQGNVF SCSVMHEALH NHYTQKSLSL    360
SPGK                                                                364

SEQ ID NO: 172          moltype = AA  length = 364
FEATURE                 Location/Qualifiers
source                  1..364
                        mol_type = protein
                        organism = synthetic construct
SEQUENCE: 172
QVQLVESGGG LVQAGGSLRL SCAASGFIFD DYAIAWFRQA PGKEREGVSF ISNSDGTAYY     60
ADSVKGRFTI SSDNAKNTVY LQMDSLKPDD TADYYCAAEG RMGTHSGDSV YFWSFSALYD    120
YWGQGTQVTV SSEPKSADKT HTCPPCPAPE AAGGPSVFLF PPKPKDTLMI SRTPEVTCVV    180
VDVSHEDPEV KFNWYVDGVE VHNAKTKPRE EQYNSTYRVV SVLTVLHQDW LNGKEYKCKV    240
SNKALPAPIE KTISKAKGQP REPQVYTLPP SREEMTKNQV SLTCLVKGFY PSDIAVEWES    300
NGQPENNYKT TPPVLDSDGS FFLYSKLTVD KSRWQQGNVF SCSVMHEALH NHYTQKSLSL    360
```

-continued

```
SPGK                                                             364

SEQ ID NO: 173          moltype = AA  length = 364
FEATURE                 Location/Qualifiers
source                  1..364
                        mol_type = protein
                        organism = synthetic construct
SEQUENCE: 173
QLQLVESGGG LVQAGGSLRL SCAASGFNFD DYAIAWFRQA PGKEREGVSF ISNSDGTAYY  60
ADSVKGRFTI SSDNAKNTVY LQMDSLKPDD TADYYCAAEG RMGTHSRDSV YFWSFSALYD 120
YWGQGTQVTV SSEPKSADKT HTCPPCPAPE AAGGPSVFLF PPKPKDTLMI SRTPEVTCVV 180
VDVSHEDPEV KFNWYVDGVE VHNAKTKPRE EQYNSTYRVV SVLTVLHQDW LNGKEYKCKV 240
SNKALPAPIE KTISKAKGQP REPQVYTLPP SREEMTKNQV SLTCLVKGFY PSDIAVEWES 300
NGQPENNYKT TPPVLDSDGS FFLYSKLTVD KSRWQQGNVF SCSVMHEALH NHYTQKSLSL 360
SPGK                                                             364

SEQ ID NO: 174          moltype = AA  length = 364
FEATURE                 Location/Qualifiers
source                  1..364
                        mol_type = protein
                        organism = synthetic construct
SEQUENCE: 174
QVQLVESGGG LVQAGGSLRL SCAASGFSFD DYAIAWFRQA PGKEREGVSF ISNSDGTAYY  60
ADSVKGRFTI SSDNAKNTVY LQMDSLKPDD TADYYCAAEG RMGTHSRDSV YFWSFSALYD 120
YWGQGTQVTV SSEPKSADKT HTCPPCPAPE AAGGPSVFLF PPKPKDTLMI SRTPEVTCVV 180
VDVSHEDPEV KFNWYVDGVE VHNAKTKPRE EQYNSTYRVV SVLTVLHQDW LNGKEYKCKV 240
SNKALPAPIE KTISKAKGQP REPQVYTLPP SREEMTKNQV SLTCLVKGFY PSDIAVEWES 300
NGQPENNYKT TPPVLDSDGS FFLYSKLTVD KSRWQQGNVF SCSVMHEALH NHYTQKSLSL 360
SPGK                                                             364

SEQ ID NO: 175          moltype = AA  length = 364
FEATURE                 Location/Qualifiers
source                  1..364
                        mol_type = protein
                        organism = synthetic construct
SEQUENCE: 175
QLQLVESGGG LVQPGGSLRL SCVLSGGTFE RLAMGWFRQA PGKEREGVSF ISNSDGTAYY  60
ADSVKGRFTI SSDNAKNTVY LQMDSLKPDD TADYYCAAEG RMGTHSRDSV YFWSFSALYD 120
YWGQGTQVTV SAEPKSADKT HTCPPCPAPE AAGGPSVFLF PPKPKDTLMI SRTPEVTCVV 180
VDVSHEDPEV KFNWYVDGVE VHNAKTKPRE EQYNSTYRVV SVLTVLHQDW LNGKEYKCKV 240
SNKALPAPIE KTISKAKGQP REPQVYTLPP SREEMTKNQV SLTCLVKGFY PSDIAVEWES 300
NGQPENNYKT TPPVLDSDGS FFLYSKLTVD KSRWQQGNVF SCSVMHEALH NHYTQKSLSL 360
SPGK                                                             364

SEQ ID NO: 176          moltype = AA  length = 364
FEATURE                 Location/Qualifiers
source                  1..364
                        mol_type = protein
                        organism = synthetic construct
SEQUENCE: 176
QVQLVESGGG LVQAGGSLRL SCAASGFTFD DYAITWFRQA PGKEREGVSY ISNNDHNTYY  60
ADSVKGRFTI SSDNAKNTVY LQMDSLKPED TAVYYCAAEG RMGTHSRESS YFWTFPALYD 120
YWGQGTQVTV SSEPKSADKT HTCPPCPAPE AAGGPSVFLF PPKPKDTLMI SRTPEVTCVV 180
VDVSHEDPEV KFNWYVDGVE VHNAKTKPRE EQYNSTYRVV SVLTVLHQDW LNGKEYKCKV 240
SNKALPAPIE KTISKAKGQP REPQVYTLPP SREEMTKNQV SLTCLVKGFY PSDIAVEWES 300
NGQPENNYKT TPPVLDSDGS FFLYSKLTVD KSRWQQGNVF SCSVMHEALH NHYTQKSLSL 360
SPGK                                                             364

SEQ ID NO: 177          moltype = AA  length = 364
FEATURE                 Location/Qualifiers
source                  1..364
                        mol_type = protein
                        organism = synthetic construct
SEQUENCE: 177
QVQLLESGGG LVQPGGSLRL SCAASGFTFD DYAITWFRQA PGKGLEGVAY ISNFDGMTYY  60
ADSVKGRFTI SSDNSKNTVY LQMNSLRAED TAVYYCAAEG RMGTHSRDSV YFWAFSALYD 120
YWGQGTLVTV SSEPKSADKT HTCPPCPAPE AAGGPSVFLF PPKPKDTLMI SRTPEVTCVV 180
VDVSHEDPEV KFNWYVDGVE VHNAKTKPRE EQYNSTYRVV SVLTVLHQDW LNGKEYKCKV 240
SNKALPAPIE KTISKAKGQP REPQVYTLPP SREEMTKNQV SLTCLVKGFY PSDIAVEWES 300
NGQPENNYKT TPPVLDSDGS FFLYSKLTVD KSRWQQGNVF SCSVMHEALH NHYTQKSLSL 360
SPGK                                                             364

SEQ ID NO: 178          moltype = AA  length = 364
FEATURE                 Location/Qualifiers
source                  1..364
                        mol_type = protein
                        organism = synthetic construct
SEQUENCE: 178
EVQLLESGGG LVQPGGSLRL SCAASGFTFG DYAITWFRQA PGKGLEGVAY ISNFDGMTYY  60
```

```
ADSVKGRFTI SSDNSKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                                364

SEQ ID NO: 179          moltype = AA  length = 364
FEATURE                 Location/Qualifiers
source                  1..364
                        mol_type = protein
                        organism = synthetic construct
SEQUENCE: 179
QVQLLESGGG LVQPGGSLRL SCAASGFTFG DYAITWFRQA PGKGLEGVAY ISNFDGMTYY  60
ADSVKGRFTI SRDNSKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                                364

SEQ ID NO: 180          moltype = AA  length = 364
FEATURE                 Location/Qualifiers
source                  1..364
                        mol_type = protein
                        organism = synthetic construct
SEQUENCE: 180
EVQLLESGGG LVQPGGSLRL SCAASGFTFG DYAITWFRQA PGKGLEGVAY ISNFDGMTYY  60
ADSVKGRFTI SRDNSKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                                364

SEQ ID NO: 181          moltype = AA  length = 364
FEATURE                 Location/Qualifiers
source                  1..364
                        mol_type = protein
                        organism = synthetic construct
SEQUENCE: 181
EVQLLESGGG LVQAGGSLRL SCAASGFTFG DYAITWFRQA PGKGLEGVAY ISNFDGMTYY  60
ADSVKGRFTI SSDNSKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                                364

SEQ ID NO: 182          moltype = AA  length = 364
FEATURE                 Location/Qualifiers
source                  1..364
                        mol_type = protein
                        organism = synthetic construct
SEQUENCE: 182
EVQLLESGGG LVQPGGSLRL SCAASGFTFG DYAITWFRQA PGKELEGVAY ISNFDGMTYY  60
ADSVKGRFTI SSDNSKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                                364

SEQ ID NO: 183          moltype = AA  length = 364
FEATURE                 Location/Qualifiers
source                  1..364
                        mol_type = protein
                        organism = synthetic construct
SEQUENCE: 183
EVQLLESGGG LVQPGGSLRL SCAASGFTFG DYAITWFRQA PGKGREGVAY ISNFDGMTYY  60
ADSVKGRFTI SSDNSKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                                364

SEQ ID NO: 184          moltype = AA  length = 364
FEATURE                 Location/Qualifiers
```

```
source                1..364
                      mol_type = protein
                      organism = synthetic construct
SEQUENCE: 184
EVQLLESGGG LVQPGGSLRL SCAASGFTFG DYAITWFRQA PGKEREGVAY ISNFDGMTYY   60
ADSVKGRFTI SSDNSKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                              364

SEQ ID NO: 185        moltype = AA  length = 364
FEATURE               Location/Qualifiers
source                1..364
                      mol_type = protein
                      organism = synthetic construct
SEQUENCE: 185
EVQLLESGGG LVQPGGSLRL SCAASGFTFG DYAITWFRQA PGKGLEGVAY ISNFDGMTYY   60
ADSVKGRFTI SSDNAKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                              364

SEQ ID NO: 186        moltype = AA  length = 364
FEATURE               Location/Qualifiers
source                1..364
                      mol_type = protein
                      organism = synthetic construct
SEQUENCE: 186
EVQLLESGGG LVQPGGSLRL SCAASGFTFG DYAITWFRQA PGKGLEGVAY ISNFDGMTYY   60
ADSVKGRFTI SSDNSKNTVY LQMDSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                              364

SEQ ID NO: 187        moltype = AA  length = 364
FEATURE               Location/Qualifiers
source                1..364
                      mol_type = protein
                      organism = synthetic construct
SEQUENCE: 187
EVQLLESGGG LVQPGGSLRL SCAASGFTFG DYAITWFRQA PGKGLEGVAY ISNFDGMTYY   60
ADSVKGRFTI SSDNSKNTVY LQMNSLRPED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                              364

SEQ ID NO: 188        moltype = AA  length = 364
FEATURE               Location/Qualifiers
source                1..364
                      mol_type = protein
                      organism = synthetic construct
SEQUENCE: 188
EVQLLESGGG LVQPGGSLRL SCAASGFTFG DYAITWFRQA PGKGLEGVSY ISNFDGMTYY   60
ADSVKGRFTI SSDNSKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGK                                                              364

SEQ ID NO: 189        moltype = AA  length = 364
FEATURE               Location/Qualifiers
source                1..364
                      mol_type = protein
                      organism = synthetic construct
SEQUENCE: 189
EVQLVESGGG LVQPGGSLRL SCAASGFTFG DYAITWFRQA PGKGLEGVAY ISNFDGMTYY   60
ADSVKGRFTI SSDNSKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLMI SRTPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
```

```
NGQPENNYKT TPPVLDSDGS FFLYSKLTVD KSRWQQGNVF SCSVMHEALH NHYTQKSLSL   360
SPGK                                                               364

SEQ ID NO: 190              moltype = AA  length = 364
FEATURE                     Location/Qualifiers
source                      1..364
                            mol_type = protein
                            organism = synthetic construct
SEQUENCE: 190
EVQLLESGGG LVQPGGSLRL SCAASGFTFG DYAITWVRQA PGKGLEGVAY ISNFDGMTYY   60
ADSVKGRFTI SSDNSKNTVY LQMNSLRAED TAVYYCAAEG RMGTHSRDSV YFWAFSALYD   120
YWGQGTLVTV SSEPKSADKT HTCPPCPAPE AAGGPSVFLF PPKPKDTLMI SRTPEVTCVV   180
VDVSHEDPEV KFNWYVDGVE VHNAKTKPRE EQYNSTYRVV SVLTVLHQDW LNGKEYKCKV   240
SNKALPAPIE KTISKAKGQP REPQVYTLPP SREEMTKNQV SLTCLVKGFY PSDIAVEWES   300
NGQPENNYKT TPPVLDSDGS FFLYSKLTVD KSRWQQGNVF SCSVMHEALH NHYTQKSLSL   360
SPGK                                                               364

SEQ ID NO: 191              moltype = AA  length = 360
FEATURE                     Location/Qualifiers
source                      1..360
                            mol_type = protein
                            organism = synthetic construct
SEQUENCE: 191
QLQLVESGGG LVQAGGSLRL SCAASGRTFS NYAMGWFRQA PGKEREFVAT ISWNGGSTYY   60
EDSVKGRFTI SRDNSENTVD LQMNSLKPED TAVYYCAARW LPVNQFLGVM RPSFVSAWGQ   120
GTQVTVSSEP KSADKTHTCP PCPAPEAAGG PSVFLFPPKP KDTLMISRTP EVTCVVVDVS   180
HEDPEVKFNW YVDGVEVHNA KTKPREEQYN STYRVVSVLT VLHQDWLNGK EYKCKVSNKA   240
LPAPIEKTIS KAKGQPREPQ VYTLPPSREE MTKNQVSLTC LVKGFYPSDI AVEWESNGQP   300
ENNYKTTPPV LDSDGSFFLY SKLTVDKSRW QQGNVFSCSV MHEALHNHYT QKSLSLSPGK   360

SEQ ID NO: 192              moltype = AA  length = 358
FEATURE                     Location/Qualifiers
source                      1..358
                            mol_type = protein
                            organism = synthetic construct
SEQUENCE: 192
QVQLVESGGG LVQAGGSLRL SCAASTRTFS HLAMGWFRQA VGKEREPVAT ISWGGDRTYY   60
ADSVKARFAI SRDNAKSTVY LQMNSLKPED TAIYYCAADK LLFGWGSPPN TDFGSWGQGT   120
QVTVSSEPKS ADKTHTCPPC PAPEAAGGPS VFLFPPKPKD TLMISRTPEV TCVVVDVSHE   180
DPEVKFNWYV DGVEVHNAKT KPREEQYNST YRVVSVLTVL HQDWLNGKEY KCKVSNKALP   240
APIEKTISKA KGQPREPQVY TLPPSREEMT KNQVSLTCLV KGFYPSDIAV EWESNGQPEN   300
NYKTTPPVLD SDGSFFLYSK LTVDKSRWQQ GNVFSCSVMH EALHNHYTQK SLSLSPGK     358

SEQ ID NO: 193              moltype = AA  length = 356
FEATURE                     Location/Qualifiers
source                      1..356
                            mol_type = protein
                            organism = synthetic construct
SEQUENCE: 193
QVQLVESGGG LVQAGDSLRL SCAVSGRRIF PLLTMGWFRQ NPGKDREFVA VIPRTGDSTY   60
YADSVKGRFA ISRDNAKNTV HLQMNSLKPE DTAVYYCAAR DGSSSPRPAD FGFWGQGTQV   120
TVSSEPKSAD KTHTCPPCPA PEAAGGPSVF LFPPKPKDTL MISRTPEVTC VVVDVSHEDP   180
EVKFNWYVDG VEVHNAKTKP REEQYNSTYR VVSVLTVLHQ DWLNGKEYKC KVSNKALPAP   240
IEKTISKAKG QPREPQVYTL PPSREEMTKN QVSLTCLVKG FYPSDIAVEW ESNGQPENNY   300
KTTPPVLDSD GSFFLYSKLT VDKSRWQQGN VFSCSVMHEA LHNHYTQKSL SLSPGK       356

SEQ ID NO: 194              moltype = AA  length = 357
FEATURE                     Location/Qualifiers
source                      1..357
                            mol_type = protein
                            organism = synthetic construct
SEQUENCE: 194
QLQLVESGGD LVQPGGSLRL SCLASGFTFS NHWMYWLRQA PGKGLEWVSD ISPGGISTRY   60
ADSVKGRFTI SRDNAKNTVY LEMSSLKPLD TAVYYCAAGR AYVAGVSRAS QYVYWGQGTQ   120
VTVSSEPKSA DKTHTCPPCP APEAAGGPSV FLFPPKPKDT LMISRTPEVT CVVVDVSHED   180
PEVKFNWYVD GVEVHNAKTK PREEQYNSTY RVVSVLTVLH QDWLNGKEYK CKVSNKALPA   240
PIEKTISKAK GQPREPQVYT LPPSREEMTK NQVSLTCLVK GFYPSDIAVE WESNGQPENN   300
YKTTPPVLDS DGSFFLYSKL TVDKSRWQQG NVFSCSVMHE ALHNHYTQKS LSLSPGK      357

SEQ ID NO: 195              moltype = AA  length = 355
FEATURE                     Location/Qualifiers
source                      1..355
                            mol_type = protein
                            organism = synthetic construct
SEQUENCE: 195
QLQLVESGGG LVQPGGSLRL SCAASGRTFS HYTVGWFRQA PGKEREFVAG LSWNHRTKYA   60
DSVKGRFTIS VDNAKNTVYL QMNSLKPEDT AVYVCTADVS PFITTIQTDM EYWGKGTLVT   120
VSSEPKSADK THTCPPCPAP EAAGGPSVFL FPPKPKDTLM ISRTPEVTCV VVDVSHEDPE   180
VKFNWYVDGV EVHNAKTKPR EEQYNSTYRV VSVLTVLHQD WLNGKEYKCK VSNKALPAPI   240
```

```
EKTISKAKGQ PREPQVYTLP PSREEMTKNQ VSLTCLVKGF YPSDIAVEWE SNGQPENNYK    300
TTPPVLDSDG SFFLYSKLTV DKSRWQQGNV FSCSVMHEAL HNHYTQKSLS LSPGK         355

SEQ ID NO: 196           moltype = AA  length = 355
FEATURE                  Location/Qualifiers
source                   1..355
                         mol_type = protein
                         organism = synthetic construct
SEQUENCE: 196
QLQLVESGGG LVQSGGSLRL SCTTSGIIFS KHGMGWYRQA PGAQRELVAR ITSGGSTSYA    60
DSGKGRFTIS RDNTKNTLYL QMNSLEPEDT AVYYCNVERF IINVEGAGRG PYWGQGTLVT    120
VSSEPKSADK THTCPPCPAP EAAGGPSVFL FPPKPKDTLM ISRTPEVTCV VVDVSHEDPE    180
VKFNWYVDGV EVHNAKTKPR EEQYNSTYRV VSVLTVLHQD WLNGKEYKCK VSNKALPAPI    240
EKTISKAKGQ PREPQVYTLP PSREEMTKNQ VSLTCLVKGF YPSDIAVEWE SNGQPENNYK    300
TTPPVLDSDG SFFLYSKLTV DKSRWQQGNV FSCSVMHEAL HNHYTQKSLS LSPGK         355

SEQ ID NO: 197           moltype = AA  length = 357
FEATURE                  Location/Qualifiers
source                   1..357
                         mol_type = protein
                         organism = synthetic construct
SEQUENCE: 197
QVQLVESGGG LVQAGGSLRL SCAVSGRTFS TLNMGWFRQA PGKEREFVAN IGWSGGTTYS    60
SDSAKGRFTI SRDNAENTVY LQMNSLKPED TAVYYCAADI KGLYFPRDAR SFDYWGQGTQ    120
VTVSSEPKSA DKTHTCPPCP APEAAGGPSV FLFPPKPKDT LMISRTPEVT CVVVDVSHED    180
PEVKFNWYVD GVEVHNAKTK PREEQYNSTY RVVSVLTVLH QDWLNGKEYK CKVSNKALPA    240
PIEKTISKAK GQPREPQVYT LPPSREEMTK NQVSLTCLVK GFYPSDIAVE WESNGQPENN    300
YKTTPPVLDS DGSFFLYSKL TVDKSRWQQG NVFSCSVMHE ALHNHYTQKS LSLSPGK       357

SEQ ID NO: 198           moltype = AA  length = 355
FEATURE                  Location/Qualifiers
source                   1..355
                         mol_type = protein
                         organism = synthetic construct
SEQUENCE: 198
QLQLVESGGG LVQAGGSLRL SCAASGRIFP IYHMGWFRQA PGKEREFVAA IRRSDSMTNY    60
ADSVKGRFTI SRDNAKNTLF LQMNSLRPED TGVYNCAAAL GQYYGANTQY DSWGQGTQVT    120
VSSEPKSADK THTCPPCPAP EAAGGPSVFL FPPKPKDTLM ISRTPEVTCV VVDVSHEDPE    180
VKFNWYVDGV EVHNAKTKPR EEQYNSTYRV VSVLTVLHQD WLNGKEYKCK VSNKALPAPI    240
EKTISKAKGQ PREPQVYTLP PSREEMTKNQ VSLTCLVKGF YPSDIAVEWE SNGQPENNYK    300
TTPPVLDSDG SFFLYSKLTV DKSRWQQGNV FSCSVMHEAL HNHYTQKSLS LSPGK         355

SEQ ID NO: 199           moltype = AA  length = 351
FEATURE                  Location/Qualifiers
source                   1..351
                         mol_type = protein
                         organism = synthetic construct
SEQUENCE: 199
QLQLVESGGG LVQPGGSLRL SCAASGSIFR FNLMGWYRQA PGKQRELVAV MSEGGTTNYG    60
DSVKGRFTMS RDNAKNTVYL QMNSLKSEDT AVYYCNFWGS NSGPVLQYWG QGTQVTVSSE    120
PKSADKTHTC PPCPAPEAAG GPSVFLFPPK PKDTLMISRT PEVTCVVVDV SHEDPEVKFN    180
WYVDGVEVHN AKTKPREEQY NSTYRVVSVL TVLHQDWLNG KEYKCKVSNK ALPAPIEKTI    240
SKAKGQPREP QVYTLPPSRE EMTKNQVSLT CLVKGFYPSD IAVEWESNGQ PENNYKTTPP    300
VLDSDGSFFL YSKLTVDKSR WQQGNVFSCS VMHEALHNHY TQKSLSLSPG K             351

SEQ ID NO: 200           moltype = AA  length = 356
FEATURE                  Location/Qualifiers
source                   1..356
                         mol_type = protein
                         organism = synthetic construct
SEQUENCE: 200
QVQLVESGGG SVQPGGSLRL ACAASGRIFV ISNAGWFRQT PGKEREFVAS ISRHGEITNY    60
ADAVKGRFTI SRDNSKNMMY LQMNSLNFED TAVYYCATTL GHSPRTDPGD FDSWGQGTQV    120
TVSSEPKSAD KTHTCPPCPA PEAAGGPSVF LFPPKPKDTL MISRTPEVTC VVVDVSHEDP    180
EVKFNWYVDG VEVHNAKTKP REEQYNSTYR VVSVLTVLHQ DWLNGKEYKC KVSNKALPAP    240
IEKTISKAKG QPREPQVYTL PPSREEMTKN QVSLTCLVKG FYPSDIAVEW ESNGQPENNY    300
KTTPPVLDSD GSFFLYSKLT VDKSRWQQGN VFSCSVMHEA LHNHYTQKSL SLSPGK        356

SEQ ID NO: 201           moltype = AA  length = 355
FEATURE                  Location/Qualifiers
source                   1..355
                         mol_type = protein
                         organism = synthetic construct
SEQUENCE: 201
QVQLVESGGG LVQPGGSLRL SCAASGSIFR INTMGWYRQA PGKQRELVAS FTSGGSPNYA    60
DSVKGRFTIS RDNAKNTVYL QMNSLRPEET AVYYCNAYIM AWSHGVLKGY DSWGQGTQVT    120
VSSEPKSADK THTCPPCPAP EAAGGPSVFL FPPKPKDTLM ISRTPEVTCV VVDVSHEDPE    180
VKFNWYVDGV EVHNAKTKPR EEQYNSTYRV VSVLTVLHQD WLNGKEYKCK VSNKALPAPI    240
EKTISKAKGQ PREPQVYTLP PSREEMTKNQ VSLTCLVKGF YPSDIAVEWE SNGQPENNYK    300
```

```
TTPPVLDSDG SFFLYSKLTV DKSRWQQGNV FSCSVMHEAL HNHYTQKSLS LSPGK         355

SEQ ID NO: 202        moltype = AA  length = 353
FEATURE               Location/Qualifiers
source                1..353
                      mol_type = protein
                      organism = synthetic construct
SEQUENCE: 202
QVQLVESGGG LVQPGESLRL SCAASGSIRT VNYMGWHRQA PGKQRELVAV VTSGGGTNYA     60
DSVKGRFTIS RDDTKNTVYL AMNSLKPEDT AVYYCNAAAS TYSSTVVRSF WGQGTQVTVS     120
SEPKSADKTH TCPPCPAPEA AGGPSVFLFP PKPKDTLMIS RTPEVTCVVV DVSHEDPEVK     180
FNWYVDGVEV HNAKTKPREE QYNSTYRVVS VLTVLHQDWL NGKEYKCKVS NKALPAPIEK     240
TISKAKGQPR EPQVYTLPPS REEMTKNQVS LTCLVKGFYP SDIAVEWESN GQPENNYKTT     300
PPVLDSDGSF FLYSKLTVDK SRWQQGNVFS CSVMHEALHN HYTQKSLSLS PGK           353

SEQ ID NO: 203        moltype = AA  length = 356
FEATURE               Location/Qualifiers
source                1..356
                      mol_type = protein
                      organism = synthetic construct
SEQUENCE: 203
QVQLVESGGG LVQPGGSLRL SCAASGSIFR INSMGWYRQA PGKQRELVAT FTTSGGVTNY     60
ADSVKGRFTI SRDNAKNTVY LQMNNLTPEE TAVYYCNAYV MAWSRGVLKG YDSWGQGTQV     120
TVSSEPKSAD KTHTCPPCPA PEAAGGPSVF LFPPKPKDTL MISRTPEVTC VVVDVSHEDP     180
EVKFNWYVDG VEVHNAKTKP REEQYNSTYR VVSVLTVLHQ DWLNGKEYKC KVSNKALPAP     240
IEKTISKAKG QPREPQVYTL PPSREEMTKN QVSLTCLVKG FYPSDIAVEW ESNGQPENNY     300
KTTPPVLDSD GSFFLYSKLT VDKSRWQQGN VFSCSVMHEA LHNHYTQKSL SLSPGK        356

SEQ ID NO: 204        moltype = AA  length = 355
FEATURE               Location/Qualifiers
source                1..355
                      mol_type = protein
                      organism = synthetic construct
SEQUENCE: 204
QVQLVESGGG LVQAGGSLRL SCAASGRTFS GYRMGWFRQA PGKEREFVAS IRWIGPATAY     60
ADSVKGRFTI SRDNAKNTVY LQMNSLKSED TAVYYCAADP TPSIDYKRGY DYWGQGTQVT     120
VSSEPKSADK THTCPPCPAP EAAGGPSVFL FPPKPKDTLM ISRTPEVTCV VVDVSHEDPE     180
VKFNWYVDGV EVHNAKTKPR EEQYNSTYRV VSVLTVLHQD WLNGKEYKC KVSNKALPAPI     240
EKTISKAKGQ PREPQVYTLP PSREEMTKNQ VSLTCLVKGF YPSDIAVEWE SNGQPENNYK     300
TTPPVLDSDG SFFLYSKLTV DKSRWQQGNV FSCSVMHEAL HNHYTQKSLS LSPGK         355

SEQ ID NO: 205        moltype = AA  length = 356
FEATURE               Location/Qualifiers
source                1..356
                      mol_type = protein
                      organism = synthetic construct
SEQUENCE: 205
QVQLVESGGG LVQPGGSLRV SCAASGRTFN TFRTGWFRQA PGKEREFVAS LNWSSTWTSY     60
ADSVKGRFSI SRDSAKNTVY LQMNSLKPED TADYYCAVGI AGTPVMRATS YIYWGQGTQV     120
TVSSEPKSAD KTHTCPPCPA PEAAGGPSVF LFPPKPKDTL MISRTPEVTC VVVDVSHEDP     180
EVKFNWYVDG VEVHNAKTKP REEQYNSTYR VVSVLTVLHQ DWLNGKEYKC KVSNKALPAP     240
IEKTISKAKG QPREPQVYTL PPSREEMTKN QVSLTCLVKG FYPSDIAVEW ESNGQPENNY     300
KTTPPVLDSD GSFFLYSKLT VDKSRWQQGN VFSCSVMHEA LHNHYTQKSL SLSPGK        356

SEQ ID NO: 206        moltype = AA  length = 355
FEATURE               Location/Qualifiers
source                1..355
                      mol_type = protein
                      organism = synthetic construct
SEQUENCE: 206
QVQLVESGGG LVQPGGSLRL SCAASRFIFP IYAMGWFRQA PGKEREFVAG IERTTDTTLY     60
ADSVKGRFTI SRDNAKNTVY LQMYSLKPED AAVYYCAARN SRRIGDVNDV DYWGQGTQVT     120
VSSEPKSADK THTCPPCPAP EAAGGPSVFL FPPKPKDTLM ISRTPEVTCV VVDVSHEDPE     180
VKFNWYVDGV EVHNAKTKPR EEQYNSTYRV VSVLTVLHQD WLNGKEYKCK VSNKALPAPI     240
EKTISKAKGQ PREPQVYTLP PSREEMTKNQ VSLTCLVKGF YPSDIAVEWE SNGQPENNYK     300
TTPPVLDSDG SFFLYSKLTV DKSRWQQGNV FSCSVMHEAL HNHYTQKSLS LSPGK         355

SEQ ID NO: 207        moltype = AA  length = 355
FEATURE               Location/Qualifiers
source                1..355
                      mol_type = protein
                      organism = synthetic construct
SEQUENCE: 207
QLQLVESGGG LVQAGGSLRL SCAASRTIFP LYAMGWFRQA PGKEREFVAG ISRTTSTTLY     60
ADSVKGRFTI SRDNAANTVY LQMNTLKPED AAVYYCAARN SRTIGDVNDV DYWGQGTQLT     120
VSSEPKSADK THTCPPCPAP EAAGGPSVFL FPPKPKDTLM ISRTPEVTCV VVDVSHEDPE     180
VKFNWYVDGV EVHNAKTKPR EEQYNSTYRV VSVLTVLHQD WLNGKEYKCK VSNKALPAPI     240
EKTISKAKGQ PREPQVYTLP PSREEMTKNQ VSLTCLVKGF YPSDIAVEWE SNGQPENNYK     300
TTPPVLDSDG SFFLYSKLTV DKSRWQQGNV FSCSVMHEAL HNHYTQKSLS LSPGK         355
```

```
SEQ ID NO: 208            moltype = AA  length = 356
FEATURE                   Location/Qualifiers
source                    1..356
                          mol_type = protein
                          organism = synthetic construct
SEQUENCE: 208
QVQLVESGGG LVQAGGSLRL SCAASGRTIS IYMMGWFRQA PGKGREFVSA IMPSGSRTYS    60
ADWVKGRFTI SRDNSKSTVY LQMNSLKPED TAVYYCAAKL FRGSGDYIND YDHWGQGTQV   120
TVSSEPKSAD KTHTCPPCPA PEAAGGPSVF LFPPKPKDTL MISRTPEVTC VVVDVSHEDP   180
EVKFNWYVDG VEVHNAKTKP REEQYNSTYR VVSVLTVLHQ DWLNGKEYKC KVSNKALPAP   240
IEKTISKAKG QPREPQVYTL PPSREEMTKN QVSLTCLVKG FYPSDIAVEW ESNGQPENNY   300
KTTPPVLDSD GSFFLYSKLT VDKSRWQQGN VFSCSVMHEA LHNHYTQKSL SLSPGK       356

SEQ ID NO: 209            moltype = AA  length = 353
FEATURE                   Location/Qualifiers
source                    1..353
                          mol_type = protein
                          organism = synthetic construct
SEQUENCE: 209
QVQLVESGGG LVQPGGSLRL SCAASGSIRT VNYMGWHRQA PGKQRELVAV VTSGGGTNYA    60
DSVKGRFTIS RDDTKNTVYL QMNSLRAEDT AVYYCNAAAS TYSSTVVRSF WGQGTLVTVS   120
SEPKSADKTH TCPPCPAPEA AGGPSVFLFP PKPKDTLMIS RTPEVTCVVV DVSHEDPEVK   180
FNWYVDGVEV HNAKTKPREE QYNSTYRVVS VLTVLHQDWL NGKEYKCKVS NKALPAPIEK   240
TISKAKGQPR EPQVYTLPPS REEMTKNQVS LTCLVKGFYP SDIAVEWESN GQPENNYKTT   300
PPVLDSDGSF FLYSKLTVDK SRWQQGNVFS CSVMHEALHN HYTQKSLSLS PGK          353

SEQ ID NO: 210            moltype = AA  length = 353
FEATURE                   Location/Qualifiers
source                    1..353
                          mol_type = protein
                          organism = synthetic construct
SEQUENCE: 210
QVQLVESGGG LVQPGGSLRL SCAASGSIRT VNYMGWHRQA PGKQRELVAV VTSGGGTNYA    60
DSVKGRFTIS RDNTKNTVYL QMNSLRAEDT AVYYCNAAAS TYSSTVVRSF WGQGTLVTVS   120
SEPKSADKTH TCPPCPAPEA AGGPSVFLFP PKPKDTLMIS RTPEVTCVVV DVSHEDPEVK   180
FNWYVDGVEV HNAKTKPREE QYNSTYRVVS VLTVLHQDWL NGKEYKCKVS NKALPAPIEK   240
TISKAKGQPR EPQVYTLPPS REEMTKNQVS LTCLVKGFYP SDIAVEWESN GQPENNYKTT   300
PPVLDSDGSF FLYSKLTVDK SRWQQGNVFS CSVMHEALHN HYTQKSLSLS PGK          353

SEQ ID NO: 211            moltype = AA  length = 353
FEATURE                   Location/Qualifiers
source                    1..353
                          mol_type = protein
                          organism = synthetic construct
SEQUENCE: 211
QVQLVESGGG LVQPGGSLRL SCAASGSIRT VNYMGWHRQA PGKQRELVAV VTSGGGTNYA    60
DSVKGRFTIS RDDSKNTVYL QMNSLRAEDT AVYYCNAAAS TYSSTVVRSF WGQGTLVTVS   120
SEPKSADKTH TCPPCPAPEA AGGPSVFLFP PKPKDTLMIS RTPEVTCVVV DVSHEDPEVK   180
FNWYVDGVEV HNAKTKPREE QYNSTYRVVS VLTVLHQDWL NGKEYKCKVS NKALPAPIEK   240
TISKAKGQPR EPQVYTLPPS REEMTKNQVS LTCLVKGFYP SDIAVEWESN GQPENNYKTT   300
PPVLDSDGSF FLYSKLTVDK SRWQQGNVFS CSVMHEALHN HYTQKSLSLS PGK          353

SEQ ID NO: 212            moltype = AA  length = 353
FEATURE                   Location/Qualifiers
source                    1..353
                          mol_type = protein
                          organism = synthetic construct
SEQUENCE: 212
QVQLVESGGG LVQPGGSLRL SCAASGSIRT VNYMGWHRQA PGKQRELVAV VTSGGGTNYA    60
DSVKGRFTIS RDNSKNTVYL QMNSLRAEDT AVYYCNAAAS TYSSTVVRSF WGQGTLVTVS   120
SEPKSADKTH TCPPCPAPEA AGGPSVFLFP PKPKDTLMIS RTPEVTCVVV DVSHEDPEVK   180
FNWYVDGVEV HNAKTKPREE QYNSTYRVVS VLTVLHQDWL NGKEYKCKVS NKALPAPIEK   240
TISKAKGQPR EPQVYTLPPS REEMTKNQVS LTCLVKGFYP SDIAVEWESN GQPENNYKTT   300
PPVLDSDGSF FLYSKLTVDK SRWQQGNVFS CSVMHEALHN HYTQKSLSLS PGK          353

SEQ ID NO: 213            moltype = AA  length = 353
FEATURE                   Location/Qualifiers
source                    1..353
                          mol_type = protein
                          organism = synthetic construct
SEQUENCE: 213
QVQLVESGGG LVQPGGSLRL SCAASGSIRT VNYMGWHRQA PGKGRELVAV VTSGGGTNYA    60
DSVKGRFTIS RDDTKNTVYL QMNSLRAEDT AVYYCNAAAS TYSSTVVRSF WGQGTLVTVS   120
SEPKSADKTH TCPPCPAPEA AGGPSVFLFP PKPKDTLMIS RTPEVTCVVV DVSHEDPEVK   180
FNWYVDGVEV HNAKTKPREE QYNSTYRVVS VLTVLHQDWL NGKEYKCKVS NKALPAPIEK   240
TISKAKGQPR EPQVYTLPPS REEMTKNQVS LTCLVKGFYP SDIAVEWESN GQPENNYKTT   300
PPVLDSDGSF FLYSKLTVDK SRWQQGNVFS CSVMHEALHN HYTQKSLSLS PGK          353
```

-continued

```
SEQ ID NO: 214          moltype = AA   length = 353
FEATURE                 Location/Qualifiers
source                  1..353
                        mol_type = protein
                        organism = synthetic construct
SEQUENCE: 214
QVQLVESGGG LVQPGGSLRL SCAASGSIRT VNYMGWHRQA PGKQLELVAV VTSGGGTNYA  60
DSVKGRFTIS RDDTKNTVYL QMNSLRAEDT AVYYCNAAAS TYSSTVVRSF WGQGTLVTVS  120
SEPKSADKTH TCPPCPAPEA AGGPSVFLFP PKPKDTLMIS RTPEVTCVVV DVSHEDPEVK  180
FNWYVDGVEV HNAKTKPREE QYNSTYRVVS VLTVLHQDWL NGKEYKCKVS NKALPAPIEK  240
TISKAKGQPR EPQVYTLPPS REEMTKNQVS LTCLVKGFYP SDIAVEWESN GQPENNYKTT  300
PPVLDSDGSF FLYSKLTVDK SRWQQGNVFS CSVMHEALHN HYTQKSLSLS PGK         353

SEQ ID NO: 215          moltype = AA   length = 353
FEATURE                 Location/Qualifiers
source                  1..353
                        mol_type = protein
                        organism = synthetic construct
SEQUENCE: 215
EVQLVESGGG LVQPGGSLRL SCAASGSIRT VNYMGWHRQA PGKQRELVAV VTSGGGTNYA  60
DSVKGRFTIS RDDTKNTVYL QMNSLRAEDT AVYYCNAAAS TYSSTVVRSF WGQGTLVTVS  120
SEPKSADKTH TCPPCPAPEA AGGPSVFLFP PKPKDTLMIS RTPEVTCVVV DVSHEDPEVK  180
FNWYVDGVEV HNAKTKPREE QYNSTYRVVS VLTVLHQDWL NGKEYKCKVS NKALPAPIEK  240
TISKAKGQPR EPQVYTLPPS REEMTKNQVS LTCLVKGFYP SDIAVEWESN GQPENNYKTT  300
PPVLDSDGSF FLYSKLTVDK SRWQQGNVFS CSVMHEALHN HYTQKSLSLS PGK         353

SEQ ID NO: 216          moltype = AA   length = 353
FEATURE                 Location/Qualifiers
source                  1..353
                        mol_type = protein
                        organism = synthetic construct
SEQUENCE: 216
QVQLVESGGG LVQPGGSLRL SCAASGSIRT VNYMGWHRQA PGKQRELVSV VTSGGGTNYA  60
DSVKGRFTIS RDDTKNTVYL QMNSLRAEDT AVYYCNAAAS TYSSTVVRSF WGQGTLVTVS  120
SEPKSADKTH TCPPCPAPEA AGGPSVFLFP PKPKDTLMIS RTPEVTCVVV DVSHEDPEVK  180
FNWYVDGVEV HNAKTKPREE QYNSTYRVVS VLTVLHQDWL NGKEYKCKVS NKALPAPIEK  240
TISKAKGQPR EPQVYTLPPS REEMTKNQVS LTCLVKGFYP SDIAVEWESN GQPENNYKTT  300
PPVLDSDGSF FLYSKLTVDK SRWQQGNVFS CSVMHEALHN HYTQKSLSLS PGK         353

SEQ ID NO: 217          moltype = AA   length = 231
FEATURE                 Location/Qualifiers
source                  1..231
                        mol_type = protein
                        organism = synthetic construct
SEQUENCE: 217
EPKSADKTHT CPPCPAPEAA GGPSVFLFPP KPKDTLYITR EPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP G           231

SEQ ID NO: 218          moltype = AA   length = 500
FEATURE                 Location/Qualifiers
source                  1..500
                        mol_type = protein
                        organism = synthetic construct
SEQUENCE: 218
EVQLLESGGG LVQPGGSLRL SCAASGFTFG DYAITWFRQA PGKGLEGVAY ISNFDGMTYY  60
ADSVKGRFTI SSDNAKNTVY LQMNSLRAED TAVYYCAAEG RMGTHSRDSV YFWAFSALYD  120
YWGQGTLVTV SSEPKSADKT HTCPPCPAPE AAGGPSVFLF PPKPKDTLYI TREPEVTCVV  180
VDVSHEDPEV KFNWYVDGVE VHNAKTKPRE EQYNSTYRVV SVLTVLHQDW LNGKEYKCKV  240
SNKALPAPIE KTISKAKGQP REPQVYTLPP SREEMTKNQV SLTCLVKGFY PSDIAVEWES  300
NGQPENNYKT TPPVLDSDGS FFLYSKLTVD KSRWQQGNVF SCSVMHEALH NHYTQKSLSL  360
SPGGGGGSGG GGSGGGGSQV QLVESGGGLV QPGGSLRLSC AASGSIRTVN YMGWHRQAPG  420
KQRELVAVVT SGGGTNYADS VKGRFTISRD NSKNTVYLQM NSLRAEDTAV YYCNAAASTY  480
SSTVVRSFWG QGTLVTVSSA                                             500
```

TSLP-BINDING MOLECULES, IL-33-BINDING MOLECULES, AND BISPECIFIC ANTIGEN-BINDING MOLECULES, AND USES THEREOF

CROSS-REFERENCE TO RELATED APPLICATIONS

The present application is based upon and claims the right of priority to CN patent application No. 2025100213824, filed Jan. 3, 2025, the disclosure of which is hereby incorporated by reference herein in its entirety for all purposes.

SEQUENCE LISTING

The instant application contains a Sequence Listing which has been submitted electronically in XML format and is hereby incorporated by reference in its entirety. Said XML copy, created on Feb. 27, 2025, is named CIE25S6003US-ST26.xml and is 217,631 bytes in size.

TECHNICAL FIELD

The application relates to the field of immunology. More specifically, the application relates to TSLP-binding molecules, IL-33-binding molecules, and bispecific antigen-binding molecules that simultaneously target TSLP and IL-33.

BACKGROUND

Immune responses play a certain protective role for the human body in defending against foreign antigens. However, when these responses are overactive, they may lead to chronic inflammation and tissue damage, thereby triggering a series of allergic diseases such as asthma, atopic dermatitis, and allergic rhinitis. With the in-depth study of immunology, type 2 inflammatory response, which underlies the pathogenesis of multiple allergic diseases, has gradually become clearer.

Type 2 inflammatory response is driven by both the innate and adaptive immune systems, mainly involving ILC2 cells, Th2 cells, and Th2-type cytokines secreted therefrom. When epithelial tissues contact with allergens, damaged epithelial cells rapidly secrete epithelial alarmin cytokines such as Interleukin-33 (IL-33), Interleukin-25 (IL-25), and Thymic Stromal Lymphopoietin (TSLP), etc. These cytokines can activate ILC2 cells and Th2 cells, prompting them to secrete Th2-type cytokines. This, in turn, drives B cell class switching and IgE production, differentiation and migration of eosinophils, as well as degranulation of basophils and mast cells, thereby triggering an inflammatory cascade.

Skin, as the first line of defense against foreign antigens, has a key role in initiating type 2 inflammatory responses through the alarmin cytokines secreted by epithelial cells. TSLP, as a member of the IL-2 family of cytokines, binds to the heterodimeric complex receptor composed of IL-7Ra and TSLPR, activating downstream JAK/STAT and PI3K signaling pathways to regulate the activation and polarization of immune cells. TSLP can not only induce the polarization of naïve CD4+ T cells toward Th2 cells via dendritic cells, but also directly act on ILC2 cells to promote the activation of STAT5 and the expression of the key transcription factor GATA3, thereby promoting the secretion of Th2-type cytokines. IL-33, as a tissue-derived nuclear cytokine from the IL-1 family, activates downstream My D88-dependent nuclear factor κB (NF-κB) and MAPK signaling pathways through the complex receptor formed by its receptor ST2 and IL-1 receptor accessory protein (IL-1RAcP), promoting the secretion of Th2-type cytokines from ILC2 cells and Th2 cells.

Recent studies have shown that compared with the stimulation of ILC2 cells with IL-33 alone, the combined use of TSLP and IL-33 significantly promotes the proliferation of ILC2 cells and the secretion of Th2-type cytokines. This indicates a significant synergistic effect of the two in type 2 inflammatory responses.

Given the synergistic effect of TSLP and IL-33 in type 2 inflammatory responses, dual-target molecules that simultaneously block TSLP and IL-33 have shown great potential for the treatment of type 2 inflammation-related diseases.

CONTENT OF THE DISCLOSURE

After in-depth research and creative work, the inventors immunized Alpaca multiple times using human TSLP protein and human IL-33 protein as antigens. Through extensive screening and modification, the inventors successfully obtained heavy-chain single-domain antibodies that can specifically bind to human TSLP and human IL-33. These antibodies can more effectively block the binding of human TSLP or human IL-33 with their receptors and inhibit their signaling than anti-TSLP antibodies (such as Tezepelumab) and anti-IL-33 antibodies (such as Itepekimab and Etokimab) in the prior art. Furthermore, based on the anti-TSLP heavy-chain single-domain antibodies and anti-IL-33 heavy-chain single-domain antibodies, the inventors constructed bispecific antibodies simultaneously targeting human TSLP and human IL-33, which can more effectively modulate type 2 inflammatory responses than the use of TSLP antibodies or IL-33 antibodies alone. Therefore, the heavy-chain single-domain antibodies bispecific antibodies provided by the present disclosure have the potential for the treatment, prevention, or alleviation of inflammatory diseases.

Therefore, in a first aspect, the present disclosure provides a thymic stromal lymphopoietin (TSLP)-binding molecule comprising at least one immunoglobulin single variable domain specifically binding to TSLP, the immunoglobulin single variable domain specifically binding to TSLP comprises:

1) a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3;

2) a CDR1 comprising the amino acid sequence set forth in SEQ ID NO: 5, a CDR2 comprising the amino acid sequence set forth in SEQ ID NO: 6, and a CDR3 comprising the amino acid sequence set forth in SEQ ID NO: 7;

3) a CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11;

4) a CDR1 comprising the amino acid sequence set forth in SEQ ID NO: 13, a CDR2 comprising the amino acid sequence set forth in SEQ ID NO: 14, and a CDR3 comprising the amino acid sequence set forth in SEQ ID NO: 15;

5) a CDR1 comprising the amino acid sequence set forth in SEQ ID NO: 17, a CDR2 comprising the amino acid sequence set forth in SEQ ID NO: 18, and a CDR3 comprising the amino acid sequence set forth in SEQ ID NO: 19;

6) a CDR1 comprising the amino acid sequence set forth in SEQ ID NO: 21, a CDR2 comprising the amino acid sequence set forth in SEQ ID NO: 22, and a CDR3 comprising the amino acid sequence set forth in SEQ ID NO: 23;

7) a CDR1 comprising the amino acid sequence set forth in SEQ ID NO: 25, a CDR2 comprising the amino acid sequence set forth in SEQ ID NO: 26, and a CDR3 comprising the amino acid sequence set forth in SEQ ID NO: 27;

8) a CDR1 comprising the amino acid sequence set forth in SEQ ID NO: 29, a CDR2 comprising the amino acid sequence set forth in SEQ ID NO: 30, and a CDR3 comprising the amino acid sequence set forth in SEQ ID NO: 31;

9) a CDR1 comprising the amino acid sequence set forth in SEQ ID NO: 33, a CDR2 comprising the amino acid sequence set forth in SEQ ID NO: 34, and a CDR3 comprising the amino acid sequence set forth in SEQ ID NO: 35;

10) a CDR1 comprising the amino acid sequence set forth in SEQ ID NO: 37, a CDR2 comprising the amino acid sequence set forth in SEQ ID NO: 38, and a CDR3 comprising the amino acid sequence set forth in SEQ ID NO: 39;

11) a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43;

12) a CDR1 comprising the amino acid sequence set forth in SEQ ID NO: 45, a CDR2 comprising the amino acid sequence set forth in SEQ ID NO: 46, and a CDR3 comprising the amino acid sequence set forth in SEQ ID NO: 47;

13) a CDR1 comprising the amino acid sequence set forth in SEQ ID NO: 49, a CDR2 comprising the amino acid sequence set forth in SEQ ID NO: 50, and a CDR3 comprising the amino acid sequence set forth in SEQ ID NO: 51;

14) a CDR1 comprising the amino acid sequence set forth in SEQ ID NO: 53, a CDR2 comprising the amino acid sequence set forth in SEQ ID NO: 54, and a CDR3 comprising the amino acid sequence set forth in SEQ ID NO: 55;

15) a CDR1 comprising the amino acid sequence set forth in SEQ ID NO: 57, a CDR2 comprising the amino acid sequence set forth in SEQ ID NO: 58, and a CDR3 comprising the amino acid sequence set forth in SEQ ID NO: 59; or 16) a CDR1 comprising the amino acid sequence set forth in SEQ ID NO: 61, a CDR2 comprising the amino acid sequence set forth in SEQ ID NO: 62, and a CDR3 comprising the amino acid sequence set forth in SEQ ID NO: 63.

In some embodiments, the immunoglobulin single variable domain specifically binding to TSLP comprises the amino acid sequence set forth in SEQ ID NO: 4, 8, 12, 16, 20, 24, 28, 32, 36, 40, 44, 48, 52, 56, 60, 64, 65, 66, 67, 68, 69, 70, 71, 72, 73, 74, 75, 76, 77 or 78, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 4, 8, 12, 16, 20, 24, 28, 32, 36, 40, 44, 48, 52, 56, 60, 64, 65, 66, 67, 68, 69, 70, 71, 72, 73, 74, 75, 76, 77 or 78, and maintaining the specific binding to TSLP.

In a second aspect, the present disclosure provides an interleukin-33 (IL-33)-binding molecule comprising at least one immunoglobulin single variable domain specifically binding to IL-33, the immunoglobulin single variable domain specifically binding to IL-33 comprises:

1) a CDR1 comprising the amino acid sequence set forth in SEQ ID NO: 79, a CDR2 comprising the amino acid sequence set forth in SEQ ID NO: 80, and a CDR3 comprising the amino acid sequence set forth in SEQ ID NO: 81;

2) a CDR1 comprising the amino acid sequence set forth in SEQ ID NO: 83, a CDR2 comprising the amino acid sequence set forth in SEQ ID NO: 84, and a CDR3 comprising the amino acid sequence set forth in SEQ ID NO: 85;

3) a CDR1 comprising the amino acid sequence set forth in SEQ ID NO: 87, a CDR2 comprising the amino acid sequence set forth in SEQ ID NO: 88, and a CDR3 comprising the amino acid sequence set forth in SEQ ID NO: 89;

4) a CDR1 comprising the amino acid sequence set forth in SEQ ID NO: 91, a CDR2 comprising the amino acid sequence set forth in SEQ ID NO: 92, and a CDR3 comprising the amino acid sequence set forth in SEQ ID NO: 93;

5) a CDR1 comprising the amino acid sequence set forth in SEQ ID NO: 95, a CDR2 comprising the amino acid sequence set forth in SEQ ID NO: 96, and a CDR3 comprising the amino acid sequence set forth in SEQ ID NO: 97;

6) a CDR1 comprising the amino acid sequence set forth in SEQ ID NO: 99, a CDR2 comprising the amino acid sequence set forth in SEQ ID NO: 100, and a CDR3 comprising the amino acid sequence set forth in SEQ ID NO: 101;

7) a CDR1 comprising the amino acid sequence set forth in SEQ ID NO: 103, a CDR2 comprising the amino acid sequence set forth in SEQ ID NO: 104, and a CDR3 comprising the amino acid sequence set forth in SEQ ID NO: 105;

8) a CDR1 comprising the amino acid sequence set forth in SEQ ID NO: 107, a CDR2 comprising the amino acid sequence set forth in SEQ ID NO: 108, and a CDR3 comprising the amino acid sequence set forth in SEQ ID NO: 109;

9) a CDR1 comprising the amino acid sequence set forth in SEQ ID NO: 111, a CDR2 comprising the amino acid sequence set forth in SEQ ID NO: 112, and a CDR3 comprising the amino acid sequence set forth in SEQ ID NO: 113;

10) a CDR1 comprising the amino acid sequence set forth in SEQ ID NO: 115, a CDR2 comprising the amino acid sequence set forth in SEQ ID NO: 116, and a CDR3 comprising the amino acid sequence set forth in SEQ ID NO: 117;

11) a CDR1 comprising the amino acid sequence set forth in SEQ ID NO: 119, a CDR2 comprising the amino acid sequence set forth in SEQ ID NO: 120, and a CDR3 comprising the amino acid sequence set forth in SEQ ID NO: 121;

12) a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125;

13) a CDR1 comprising the amino acid sequence set forth in SEQ ID NO: 127, a CDR2 comprising the amino acid sequence set forth in SEQ ID NO: 128, and a CDR3 comprising the amino acid sequence set forth in SEQ ID NO: 129;

14) a CDR1 comprising the amino acid sequence set forth in SEQ ID NO: 131, a CDR2 comprising the amino acid sequence set forth in SEQ ID NO: 132, and a CDR3 comprising the amino acid sequence set forth in SEQ ID NO: 133;

15) a CDR1 comprising the amino acid sequence set forth in SEQ ID NO: 135, a CDR2 comprising the amino acid sequence set forth in SEQ ID NO: 136, and a CDR3 comprising the amino acid sequence set forth in SEQ ID NO: 137;

16) a CDR1 comprising the amino acid sequence set forth in SEQ ID NO: 139, a CDR2 comprising the amino acid sequence set forth in SEQ ID NO: 140, and a CDR3 comprising the amino acid sequence set forth in SEQ ID NO: 141;

17) a CDR1 comprising the amino acid sequence set forth in SEQ ID NO: 143, a CDR2 comprising the amino acid sequence set forth in SEQ ID NO: 144, and a CDR3 comprising the amino acid sequence set forth in SEQ ID NO: 145; or 18) a CDR1 comprising the amino acid sequence set forth in SEQ ID NO: 147, a CDR2 comprising the amino acid sequence set forth in SEQ ID NO: 148, and a CDR3 comprising the amino acid sequence set forth in SEQ ID NO: 149.

In some embodiments, the immunoglobulin single variable domain specifically binding to IL-33 comprises the amino acid sequence set forth in SEQ ID NO: 82, 86, 90, 94, 98, 102, 106, 110, 114, 118, 122, 126, 130, 134, 138, 142, 146, 150, 151, 152, 153, 154, 155, 156, 157 or 158, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 82, 86, 90, 94, 98, 102, 106, 110, 114, 118, 122, 126, 130, 134, 138, 142, 146, 150, 151, 152, 153, 154, 155, 156, 157 or 158, and maintaining the specific binding to IL-33.

In a third aspect, the present disclosure provides a multispecific antigen-binding molecule, which comprises the TSLP-binding molecule described in the first aspect of the present disclosure and/or the IL-33-binding molecule described in the second aspect of the present disclosure, and one or more additional antigen-binding functional regions, the one or more additional antigen-binding functional regions binds to different antigens or different epitopes of the same antigen from the TSLP-binding molecule and/or the IL-33-binding molecule.

In a fourth aspect, the present disclosure provides a bispecific antigen-binding molecule, which comprises the TSLP-binding molecule described in the first aspect of the present disclosure and the IL-33-binding molecule described in the second aspect of the present disclosure.

In some embodiments, the bispecific antigen-binding molecule comprises a first antigen-binding functional region and a second antigen-binding functional region, wherein the first antigen-binding functional region comprises at least one immunoglobulin single variable domain specifically binding to TSLP, and the immunoglobulin single variable domain specifically binding to TSLP comprises:

1) a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3;

2) a CDR1 comprising the amino acid sequence set forth in SEQ ID NO: 5, a CDR2 comprising the amino acid sequence set forth in SEQ ID NO: 6, and a CDR3 comprising the amino acid sequence set forth in SEQ ID NO: 7;

3) a CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11;

4) a CDR1 comprising the amino acid sequence set forth in SEQ ID NO: 13, a CDR2 comprising the amino acid sequence set forth in SEQ ID NO: 14, and a CDR3 comprising the amino acid sequence set forth in SEQ ID NO: 15;

5) a CDR1 comprising the amino acid sequence set forth in SEQ ID NO: 17, a CDR2 comprising the amino acid sequence set forth in SEQ ID NO: 18, and a CDR3 comprising the amino acid sequence set forth in SEQ ID NO: 19;

6) a CDR1 comprising the amino acid sequence set forth in SEQ ID NO: 21, a CDR2 comprising the amino acid sequence set forth in SEQ ID NO: 22, and a CDR3 comprising the amino acid sequence set forth in SEQ ID NO: 23;

7) a CDR1 comprising the amino acid sequence set forth in SEQ ID NO: 25, a CDR2 comprising the amino acid sequence set forth in SEQ ID NO: 26, and a CDR3 comprising the amino acid sequence set forth in SEQ ID NO: 27;

8) a CDR1 comprising the amino acid sequence set forth in SEQ ID NO: 29, a CDR2 comprising the amino acid sequence set forth in SEQ ID NO: 30, and a CDR3 comprising the amino acid sequence set forth in SEQ ID NO: 31;

9) a CDR1 comprising the amino acid sequence set forth in SEQ ID NO: 33, a CDR2 comprising the amino acid sequence set forth in SEQ ID NO: 34, and a CDR3 comprising the amino acid sequence set forth in SEQ ID NO: 35;

10) a CDR1 comprising the amino acid sequence set forth in SEQ ID NO: 37, a CDR2 comprising the amino acid sequence set forth in SEQ ID NO: 38, and a CDR3 comprising the amino acid sequence set forth in SEQ ID NO: 39;

11) a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43;

12) a CDR1 comprising the amino acid sequence set forth in SEQ ID NO: 45, a CDR2 comprising the amino acid sequence set forth in SEQ ID NO: 46, and a CDR3 comprising the amino acid sequence set forth in SEQ ID NO: 47;

13) a CDR1 comprising the amino acid sequence set forth in SEQ ID NO: 49, a CDR2 comprising the amino acid sequence set forth in SEQ ID NO: 50, and a CDR3 comprising the amino acid sequence set forth in SEQ ID NO: 51;

14) a CDR1 comprising the amino acid sequence set forth in SEQ ID NO: 53, a CDR2 comprising the amino acid sequence set forth in SEQ ID NO: 54, and a CDR3 comprising the amino acid sequence set forth in SEQ ID NO: 55;

15) a CDR1 comprising the amino acid sequence set forth in SEQ ID NO: 57, a CDR2 comprising the amino acid sequence set forth in SEQ ID NO: 58, and a CDR3 comprising the amino acid sequence set forth in SEQ ID NO: 59: or 16) a CDR1 comprising the amino acid sequence set forth in SEQ ID NO: 61, a CDR2 comprising the amino acid sequence set forth in SEQ ID NO: 62, and a CDR3 comprising the amino acid sequence set forth in SEQ ID NO: 63; and the second antigen-binding functional region comprises at least one immunoglobulin single variable domain specifically binding to IL-33, and the immunoglobulin single variable domain specifically binding to IL-33 comprises;

1) a CDR1 comprising the amino acid sequence set forth in SEQ ID NO: 79, a CDR2 comprising the amino acid sequence set forth in SEQ ID NO: 80, and a CDR3 comprising the amino acid sequence set forth in SEQ ID NO: 81;

2) a CDR1 comprising the amino acid sequence set forth in SEQ ID NO: 83, a CDR2 comprising the amino acid sequence set forth in SEQ ID NO: 84, and a CDR3 comprising the amino acid sequence set forth in SEQ ID NO: 85;

3) a CDR1 comprising the amino acid sequence set forth in SEQ ID NO: 87, a CDR2 comprising the amino acid sequence set forth in SEQ ID NO: 88, and a CDR3 comprising the amino acid sequence set forth in SEQ ID NO: 89;

4) a CDR1 comprising the amino acid sequence set forth in SEQ ID NO: 91, a CDR2 comprising the amino acid sequence set forth in SEQ ID NO: 92, and a CDR3 comprising the amino acid sequence set forth in SEQ ID NO: 93;

5) a CDR1 comprising the amino acid sequence set forth in SEQ ID NO: 95, a CDR2 comprising the amino acid sequence set forth in SEQ ID NO: 96, and a CDR3 comprising the amino acid sequence set forth in SEQ ID NO: 97;

6) a CDR1 comprising the amino acid sequence set forth in SEQ ID NO: 99, a CDR2 comprising the amino acid sequence set forth in SEQ ID NO: 100, and a CDR3 comprising the amino acid sequence set forth in SEQ ID NO: 101;

7) a CDR1 comprising the amino acid sequence set forth in SEQ ID NO: 103, a CDR2 comprising the amino acid sequence set forth in SEQ ID NO: 104, and a CDR3 comprising the amino acid sequence set forth in SEQ ID NO: 105;

8) a CDR1 comprising the amino acid sequence set forth in SEQ ID NO: 107, a CDR2 comprising the amino acid sequence set forth in SEQ ID NO: 108, and a CDR3 comprising the amino acid sequence set forth in SEQ ID NO: 109;

9) a CDR1 comprising the amino acid sequence set forth in SEQ ID NO: 111, a CDR2 comprising the amino acid sequence set forth in SEQ ID NO: 112, and a CDR3 comprising the amino acid sequence set forth in SEQ ID NO: 113;

10) a CDR1 comprising the amino acid sequence set forth in SEQ ID NO: 115, a CDR2 comprising the amino acid sequence set forth in SEQ ID NO: 116, and a CDR3 comprising the amino acid sequence set forth in SEQ ID NO: 117;

11) a CDR1 comprising the amino acid sequence set forth in SEQ ID NO: 119, a CDR2 comprising the amino acid sequence set forth in SEQ ID NO: 120, and a CDR3 comprising the amino acid sequence set forth in SEQ ID NO: 121;

12) a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125;

13) a CDR1 comprising the amino acid sequence set forth in SEQ ID NO: 127, a CDR2 comprising the amino acid sequence set forth in SEQ ID NO: 128, and a CDR3 comprising the amino acid sequence set forth in SEQ ID NO: 129;

14) a CDR1 comprising the amino acid sequence set forth in SEQ ID NO: 131, a CDR2 comprising the amino acid sequence set forth in SEQ ID NO: 132, and a CDR3 comprising the amino acid sequence set forth in SEQ ID NO: 133;

15) a CDR1 comprising the amino acid sequence set forth in SEQ ID NO: 135, a CDR2 comprising the amino acid sequence set forth in SEQ ID NO: 136, and a CDR3 comprising the amino acid sequence set forth in SEQ ID NO: 137;

16) a CDR1 comprising the amino acid sequence set forth in SEQ ID NO: 139, a CDR2 comprising the amino acid sequence set forth in SEQ ID NO: 140, and a CDR3 comprising the amino acid sequence set forth in SEQ ID NO: 141;

17) a CDR1 comprising the amino acid sequence set forth in SEQ ID NO: 143, a CDR2 comprising the amino acid sequence set forth in SEQ ID NO: 144, and a CDR3 comprising the amino acid sequence set forth in SEQ ID NO: 145; or 18) a CDR1 comprising the amino acid sequence set forth in SEQ ID NO: 147, a CDR2 comprising the amino acid sequence set forth in SEQ ID NO: 148, and a CDR3 comprising the amino acid sequence set forth in SEQ ID NO: 149.

In some embodiments, the immunoglobulin single variable domain specifically binding to TSLP comprises the amino acid sequence set forth in SEQ ID NO: 4, 8, 12, 16, 20, 24, 28, 32, 36, 40, 44, 48, 52, 56, 60, 64, 65, 66, 67, 68, 69, 70, 71, 72, 73, 74, 75, 76, 77 or 78, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 4, 8, 12, 16, 20, 24, 28, 32, 36, 40, 44, 48, 52, 56, 60, 64, 65, 66, 67, 68, 69, 70, 71, 72, 73, 74, 75, 76, 77 or 78 and maintaining the specific binding to TSLP; and the immunoglobulin single variable domain specifically binding to IL-33 comprises the amino acid sequence set forth in SEQ ID NO: 82, 86, 90, 94, 98, 102, 106, 110, 114, 118, 122, 126, 130, 134, 138, 142, 146, 150, 151, 152, 153, 154, 155, 156, 157 or 158, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 82, 86, 90, 94, 98, 102, 106, 110, 114, 118, 122, 126, 130, 134, 138, 142, 146, 150, 151, 152, 153, 154, 155, 156, 157 or 158 and maintaining the specific binding to IL-33.

In some embodiments, the immunoglobulin single variable domain specifically binding to TSLP comprises a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43.

In some embodiments, the immunoglobulin single variable domain specifically binding to TSLP comprises the amino acid sequence set forth in SEQ ID NO: 73, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 73, and maintaining the specific binding to TSLP.

In some embodiments, the immunoglobulin single variable domain specifically binding to IL-33 comprises a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125.

In some embodiments, the immunoglobulin single variable domain specifically binding to IL-33 comprises the amino acid sequence set forth in SEQ ID NO: 154, or the amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 154, and maintaining the specific binding to IL-33.

In some embodiments, the immunoglobulin single variable domain specifically binding to TSLP comprises a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43; and the immunoglobulin single variable domain specifically binding to IL-33 comprises a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125.

In some embodiments, the immunoglobulin single variable domain specifically binding to TSLP comprises the amino acid sequence set forth in SEQ ID NO: 73, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 73 and maintaining the specific binding to TSLP; and the immunoglobulin single variable domain specifically binding to IL-33 comprises the amino acid sequence set forth in SEQ ID NO: 154, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 154 and maintaining the specific binding to IL-33

In some embodiments, the immunoglobulin single variable domain specifically binding to TSLP and/or the immunoglobulin single variable domain specifically binding to IL-33 further comprise one or more substitutions, additions and/or deletions of amino acid residues and maintain the specific binding to TSLP and/or IL-33, the one or more substitutions, additions and/or deletions of amino acid residues occur in the sequence of the immunoglobulin single variable domain but not in the sequences of any CDR.

In some embodiments, the immunoglobulin single variable domain is a VHH.

In some embodiments, the immunoglobulin single variable domain is a VHH derived from a camelid, the camelid preferably is an alpaca or a llama.

In some embodiments, the immunoglobulin single variable domain is a humanized VHH.

In some embodiments, the TSLP-binding molecule is an anti-TSLP antibody or an antigen-binding fragment thereof, and/or the IL-33-binding molecule is an anti-IL-33 antibody or an antigen-binding fragment thereof.

In some embodiments, the TSLP-binding molecule and/or the IL-33-binding molecule are each independently a heavy-chain antibody, a heavy-chain single-domain antibody, a chimeric antibody, or a humanized antibody.

In some embodiments, the first antigen-binding functional region is an anti-TSLP antibody or an antigen-binding fragment thereof and/or the second antigen-binding functional region is an anti-IL-33 antibody or an antigen-binding fragment thereof.

In some embodiments, the first antigen-binding functional region and the second antigen-binding functional region are each independently a heavy-chain antibody, a heavy-chain single-domain antibody, a chimeric antibody, or a humanized antibody.

In some embodiments, the TSLP-binding molecule comprises a plurality of immunoglobulin single variable domains specifically binding to TSLP, and/or the IL-33-binding molecule comprises a plurality of immunoglobulin single variable domains that specifically binding to IL-33.

In some embodiments, the first antigen-binding functional region in the bispecific antigen-binding molecule comprises a plurality of immunoglobulin single variable domains specifically binding to TSLP, and/or the second antigen-binding functional region comprises a plurality of immunoglobulin single variable domains that specifically binding to IL-33.

In some embodiments, the numbers of the first antigen-binding functional region and the second antigen-binding functional region are each independently 1, 2, or more than 2.

In some embodiments, the plurality of immunoglobulin single variable domains and/or the plurality of antigen-binding functional regions are optionally connected via a linker, preferably, the linker is (GS)n, (GGS)n, (GGGS)n, or (GGGGS)n, where n is 1, 2, 3, 4, or 5.

In some embodiments, the TSLP-binding molecule, the IL-33-binding molecule, the multispecific binding molecule, and/or the bispecific antigen-binding molecule further comprise an immunoglobulin Fc domain.

In some embodiments, the immunoglobulin Fc domain is a human immunoglobulin Fc domain, preferably an Fc domain derived from human IgG, more preferably an Fc domain derived from human IgG1 or IgG4.

In some embodiments, wherein the immunoglobulin Fc domain further comprises one or more amino acid mutations selected from $C_{220}A$, $L_{234}A$, $L_{235}A$, $M_{252}Y$, $S_{254}T$, $T_{256}E$ and $K_{447}del$.

In some embodiments, the immunoglobulin Fc domain comprises the amino acid sequence set forth in SEQ ID NO: 159, 160 or 217, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 159, 160 or 217.

In some embodiments, the immunoglobulin Fc domain is independently connected to the immunoglobulin single variable domain and/or the first antigen-binding functional region and/or the second antigen-binding functional region via an immunoglobulin hinge region or a linker, preferably, the linker is (GS)n, (GGS)n, (GGGS)n, or (GGGGS)n, where n is 1, 2, 3, 4, or 5.

In some embodiments, the TSLP-binding molecule comprises the amino acid sequence set forth in any one of SEQ ID NOs: 161-190, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in any one of SEQ ID NOs: 161-190, and maintaining the specific binding to TSLP.

In some embodiments, the IL-33-binding molecule comprises the amino acid sequence set forth in any one of SEQ ID NOs: 191-216, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in any one of SEQ ID NOs: 191-216, and maintaining the specific binding to IL-33.

In some embodiments, the bispecific antigen-binding molecule comprises one or more polypeptide chains each independently having the structure as shown in V1-Fc-L1-V2 from the N-terminus to the C-terminus, wherein V1 and V2 are different from each other and are each independently selected from the first antigen-binding functional region or the second antigen-binding functional region, L1 is a linker, and Fc is an immunoglobulin Fc domain: preferably, V1 and V2 are the first antigen-binding functional region or the second antigen-binding functional region respectively.

In some embodiments, the bispecific antigen-binding molecule comprises the amino acid sequence set forth in SEQ ID NO: 218, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in any one of SEQ ID NO: 218 and maintaining the specific binding to TSLP and IL-33.

In a fifth aspect, the present disclosure provides a fusion protein, which comprises the TSLP-binding molecule described in the first aspect of the present disclosure, the IL-33-binding molecule described in the second aspect of the present disclosure, the multispecific antigen-binding molecule described in the third aspect of the present disclosure, and/or the bispecific antigen-binding molecule described in the fourth aspect of the present disclosure, and a polypeptide or a protein that is expressed in fusion therewith.

In a sixth aspect, the present disclosure provides a conjugate, which comprises the TSLP-binding molecule described in the first aspect of the present disclosure, the IL-33-binding molecule described in the second aspect of the present disclosure, the multispecific antigen-binding molecule described in the third aspect of the present disclosure, the bispecific antigen-binding molecule described in the fourth aspect of the present disclosure, and/or the fusion protein described in the fifth aspect of the present disclosure, and a conjugate that is conjugated thereto.

In a seventh aspect, the present disclosure provides a nucleic acid molecule, which comprises a nucleotide sequence encoding the TSLP-binding molecule described in the first aspect of the present disclosure, the IL-33-binding molecule described in the second aspect of the present disclosure, the multispecific antigen-binding molecule described in the third aspect of the present disclosure, the bispecific antigen-binding molecule described in the fourth aspect of the present disclosure, and/or the fusion protein described in the fifth aspect of the present disclosure.

In an eighth aspect, the present disclosure provides an expression vector, which comprises the nucleic acid molecule described in the seventh aspect of the present disclosure operably linked to an expression regulatory element.

In a ninth aspect, the present disclosure provides a host cell, which comprises the nucleic acid molecule described in the seventh aspect of the present disclosure and/or the expression vector described in the eighth aspect of the present disclosure.

In a tenth aspect, the present disclosure provides a method for preparing the TSLP-binding molecule described in the first aspect of the present disclosure, the IL-33-binding molecule described in the second aspect of the present disclosure, the multispecific antigen-binding molecule described in the third aspect of the present disclosure, the bispecific antigen-binding molecule described in the fourth aspect of the present disclosure, and/or the fusion protein described in the fifth aspect of the present disclosure, the method comprises:

culturing the host cell described in the ninth aspect of the present disclosure under conditions suitable for expressing the expression vector described in the eighth aspect of the present disclosure, and optionally separating and/or purifying the TSLP-binding molecule, the IL-33-binding molecule, the multispecific antigen-binding molecule, the bispecific antigen-binding molecule and/or the fusion protein from the host cell or the host cell culture.

In an eleventh aspect, the present disclosure provides a composition, which comprises the TSLP-binding molecule described in the first aspect of the present disclosure, the IL-33-binding molecule described in the second aspect of the present disclosure, the multispecific antigen-binding molecule described in the third aspect of the present disclosure, the bispecific antigen-binding molecule described in the fourth aspect of the present disclosure, the fusion protein described in the fifth aspect of the present disclosure, and/or the conjugate described in the sixth aspect of the present disclosure.

In some embodiments, the composition is a pharmaceutical composition, the pharmaceutical composition further comprises at least one pharmaceutically acceptable carrier and/or excipient, and optionally comprises one or more other pharmaceutically active therapeutic agents.

In a twelfth aspect, the present disclosure provides a use of the TSLP-binding molecule described in the first aspect of the present disclosure, the IL-33-binding molecule described in the second aspect of the present disclosure, the multispecific antigen-binding molecule described in the third aspect of the present disclosure, the bispecific antigen-binding molecule described in the fourth aspect of the present disclosure, the fusion protein described in the fifth aspect of the present disclosure, the conjugate described in the sixth aspect of the present disclosure, and/or the composition described in the eleventh aspect of the present disclosure in the preparation of a medicament for treating, preventing or alleviating inflammatory diseases.

In some embodiments, the inflammatory disease is a type 2 inflammatory disease.

In some embodiments, the type 2 inflammatory disease is selected from asthma, chronic rhinosinusitis with or without nasal polyps, allergic rhinitis, chronic obstructive pulmonary disease, atopic dermatitis, prurigo nodularis, chronic spontaneous urticaria, and eosinophilic esophagitis.

In some embodiments, the medicament further comprises one or more other therapeutic agents for treating inflammatory diseases.

In a thirteenth aspect, the present disclosure provides a method for treating, preventing or alleviating inflammatory diseases, which comprises administering a therapeutically effective amount of the TSLP-binding molecule described in the first aspect of the present disclosure, the IL-33-binding molecule described in the second aspect of the present disclosure, the multispecific antigen-binding molecule described in the third aspect of the present disclosure, the bispecific antigen-binding molecule described in the fourth aspect of the present disclosure, the fusion protein described in the fifth aspect of the present disclosure, the conjugate described in the sixth aspect of the present disclosure, and/or the composition described in the eleventh aspect of the present disclosure to a subject in need thereof.

In some embodiments, the inflammatory disease is a type 2 inflammatory disease.

In some embodiments, the type 2 inflammatory disease is selected from asthma, chronic rhinosinusitis with or without nasal polyps, allergic rhinitis, chronic obstructive pulmonary disease, atopic dermatitis, prurigo nodularis, chronic spontaneous urticaria, and eosinophilic esophagitis.

In some embodiments, the method further comprises using in combination with one or more other therapeutic agents for treating inflammatory diseases.

In a fourteenth aspect, the present disclosure provides a use of the TSLP-binding molecule described in the first aspect of the present disclosure, the IL-33-binding molecule described in the second aspect of the present disclosure, the multispecific antigen-binding molecule described in the third aspect of the present disclosure, the bispecific antigen-binding molecule described in the fourth aspect of the present disclosure, the fusion protein described in the fifth aspect of the present disclosure, and/or the conjugate described in the sixth aspect of the present disclosure in inhibiting or blocking TSLP and/or IL-33 signaling in vivo or in vitro.

14

Figure 2:
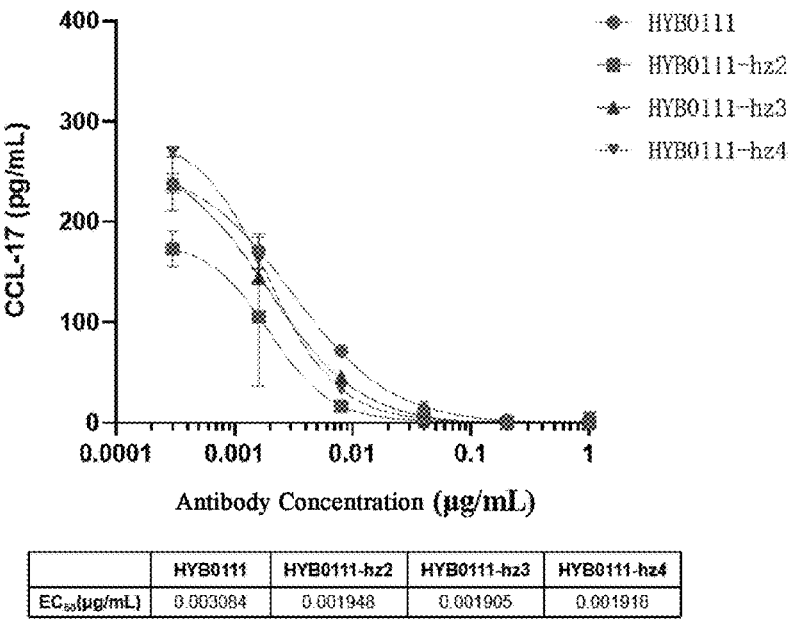

FIG. 2: Inhibition efficacy results of the humanized TSLP heavy-chain antibody on TSLP-induced CCL-17 release from human PBMCs. The experiment was performed in double replicate wells.

Figure 3:
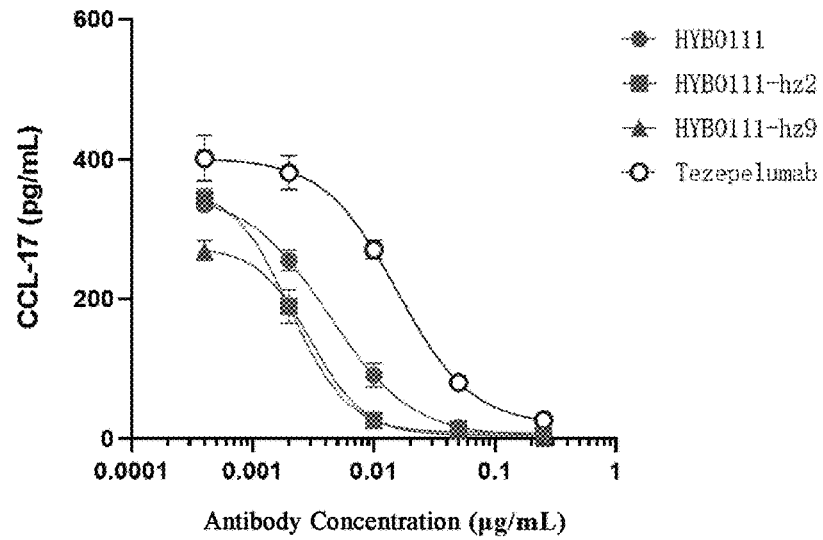

FIG. 3: Inhibition efficacy results of the further modified TSLP heavy-chain antibody on TSLP-induced CCL-17 release from human PBMCs. The experiment was performed in double replicate wells.

Figure 4:
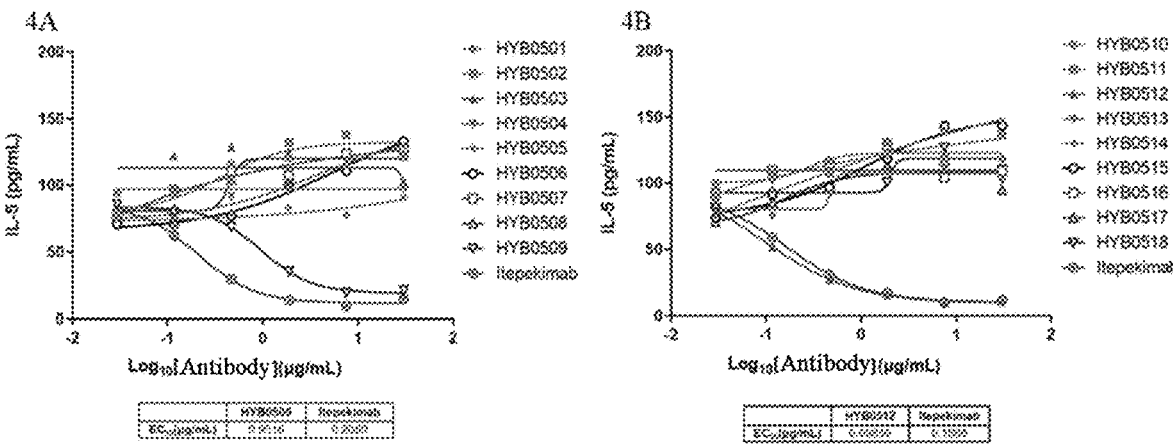

FIG. 4: Inhibition efficacy results of the initial IL-33 heavy-chain antibody on IL-33-induced IL-5 release from KU812 cells. The experiment was performed in single replicate wells and divided into two plates (see FIG. 4A and FIG. 4B).

Figure 5:
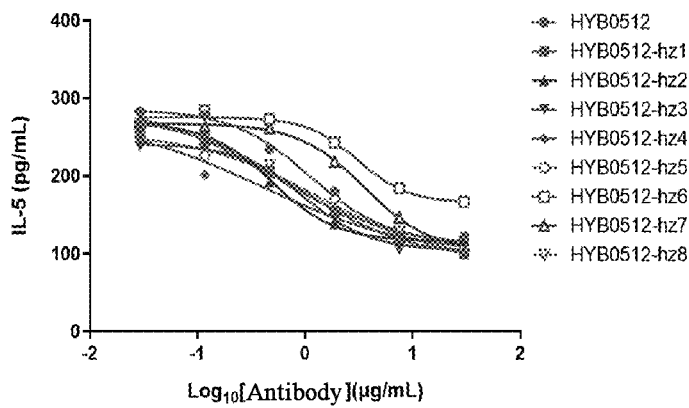

FIG. 5: Inhibition efficacy results of the humanized IL-33 heavy-chain antibody on IL-33-induced IL-5 release from KU812 cells. The experiment was performed in single replicate wells.

Figure 6:
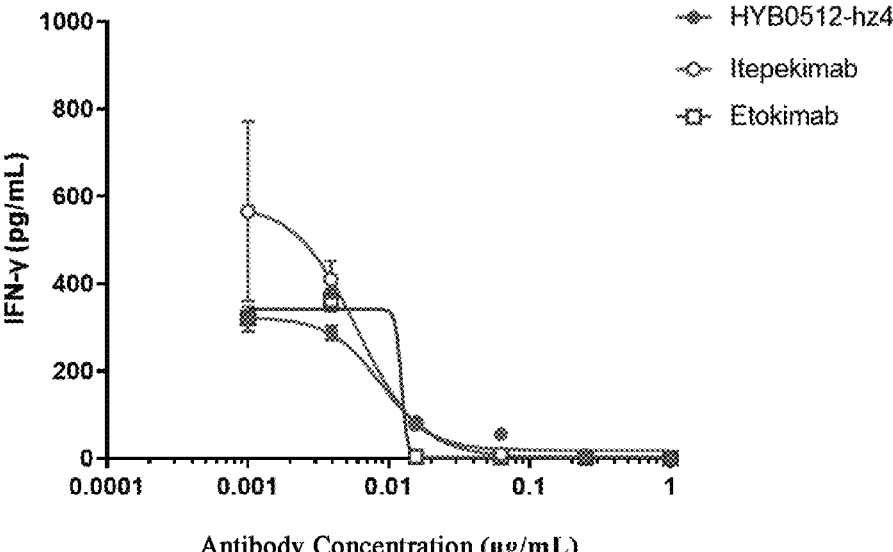

FIG. 6: Inhibition efficacy results of HYB0512-hz4 on IL-33-induced IFN-γ release from PBMCs. The experiment was performed in triple replicate wells.

Figure 7:
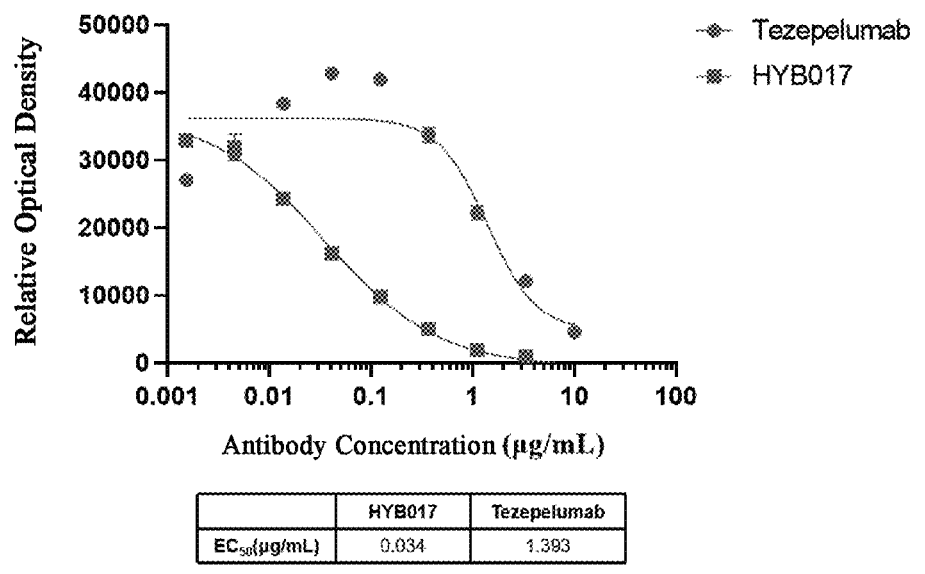

FIG. 7: Inhibition assay results of the bispecific antibody on TSLP-induced proliferation of huTSLPR&huIL-7Ra/BaF3 cells. The experiment was performed in triple replicate wells, with Tezepelumab as a positive control.

Figure 8:
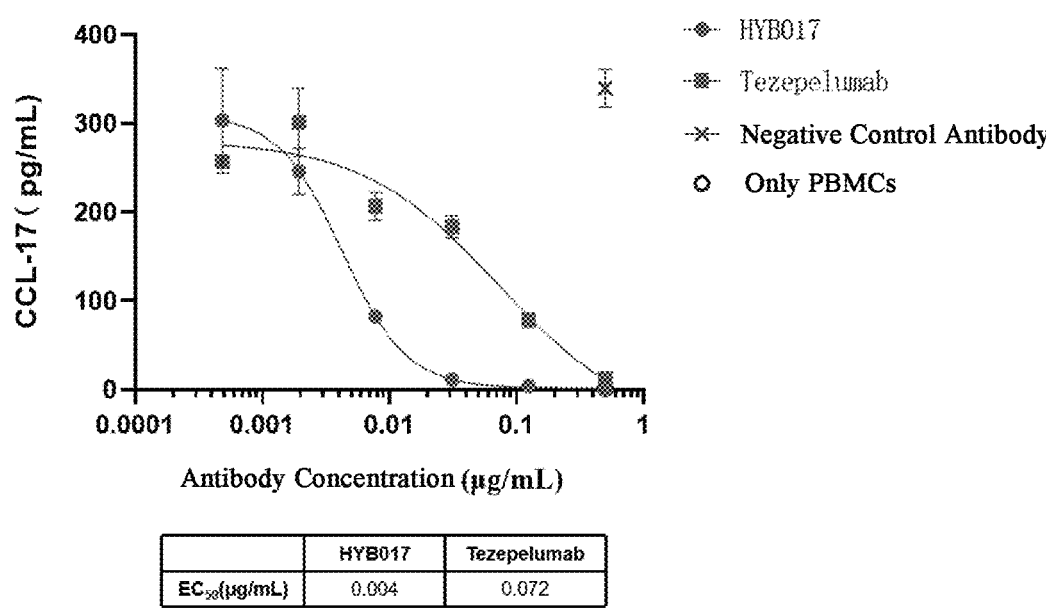

FIG. 8: Inhibition efficacy results of the bispecific antibody on TSLP-induced CCL-17 release from human PBMCs. The experiment was performed in triple replicate wells, with Tezepelumab as a positive control.

Figure 9:
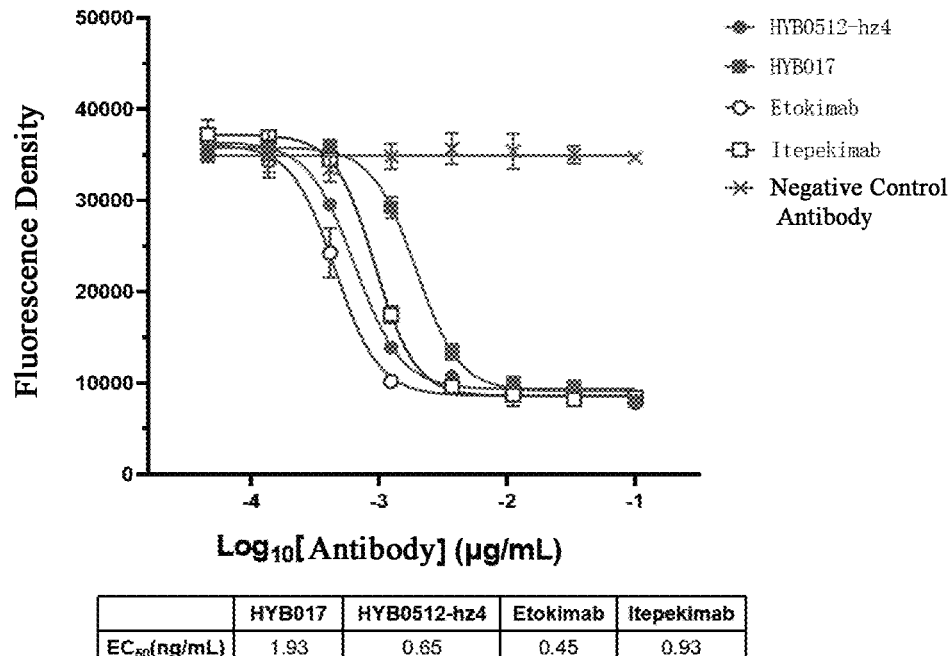

FIG. 9: Inhibition efficacy results of the bispecific antibody on IL-33-mediated reporter gene cell signaling pathway. The experiment was performed in double replicate wells, with Itepekimab and Etokimab as positive controls.

DETAILED DESCRIPTION OF THE
PREFERRED EMBODIMENT

Although the present disclosure can be implemented in many different forms, the specific illustrative embodiments disclosed herein are intended to verify the principles of the present disclosure. It should be noted that the present disclosure is not limited to the specific embodiments illustrated. It would be obvious to those skilled in the art that various equivalent forms, modifications, or changes can be made without departing from the scope of the present disclosure as disclosed, and it should be understood that these equivalent embodiments are included herein. All references cited herein, including patent publications, patents, and patent applications, are incorporated herein by reference in their entirety. In addition, any section headings used herein are for organizational purposes only and are not to be interpreted as limiting the subject matter described.

Unless otherwise defined herein, scientific and technical terms used in conjunction with the present disclosure shall have the meanings that are commonly understood by those of ordinary skill in the art. Moreover, unless otherwise required in the context, terms in the singular shall include the plural, and vice versa. More specifically, as used in the specification and the appended claims, unless otherwise specified in the context, the singular forms "a." "an," and "the" include plural referents. In the application, unless otherwise stated, the use of "or" means "and/or." In this application, terms "first," "second," and the like have no substantive meaning and are used merely to distinguish identical terms. In addition, the use of the terms "comprising." "including." "containing," and the like is not restrictive. Furthermore, the ranges provided in the specification and the appended claims include the endpoints and all values between the endpoints. The term "about," when used in conjunction with numerical values, means a range of numerical values that are within 10% below and 10% above the specified numerical value.

Generally, the terms and techniques related to cell and tissue culture, molecular biology, immunology, microbiology, genetics, and protein and nucleic acid chemistry and hybridization described herein are well-known and commonly used terms in the art. Unless otherwise specified, the methods and techniques of the present disclosure are generally performed according to conventional methods known in the art and as described in the various general and more specific references cited and discussed throughout the specification. See, for example, Sambrook J. & Russell D., Molecular Cloning: A Laboratory Manual, 3rd ed., Cold Spring Harbor Laboratory Press, Cold Spring Harbor, N.Y. (2000): Abbas et al., Cellular and Molecular Immunology, 6th ed., W.B. Saunders Company (2010): Harlow and Lane, Using Antibodies: A Laboratory Manual, Cold Spring Harbor Laboratory Press, Cold Spring Harbor, N.Y. (1998): Ausubel et al., Short Protocols in Molecular Biology: A Compendium of Methods from Current Protocols in Molecular Biology, Wiley, John & Sons, Inc. (2002); and Coligan et al., Short Protocols in Protein Science, Wiley, John & Sons, Inc. (2003). The terms and laboratory procedures and techniques related to analytical chemistry, synthetic organic chemistry, and pharmaceutical and medicinal chemistry described herein are also well-known and commonly used terms in the art.

Definitions

To better understand the present disclosure, the definitions and explanations of relevant terms are provided as follows.

As used herein, the term "antigen-binding molecule" may encompass any molecule that specifically binds to a particular antigen. In some cases, "antigen-binding molecule" may encompass "antigen antagonist." "Antigen antagonist" refers to any compound or biomolecule that blocks the specific binding of a particular antigen to its natural receptor. Antigen-binding molecules or antigen antagonists can be antigen-binding proteins. "Antigen-binding protein" generally refers to a protein molecule that comprises an antigen-binding portion, and optionally a scaffold or framework portion that allows the antigen-binding portion to adopt a conformation that facilitates the binding of the antigen-binding molecule to the antigen. Antigen-binding proteins may typically include the antibody light chain variable region (VL), the antibody heavy chain variable region (VH), or both, and functional fragments thereof. The variable regions of the heavy and light chains contain the binding domains that interact with the antigen. In this disclosure, the term "antigen-binding molecule" also encompasses heavy chain single-domain antibodies and proteins containing immunoglobulin single variable domains. Examples of antigen-binding molecules include, but are not limited to, antibodies, antigen-binding fragments, heavy chain single-domain antibodies, immunoconjugates, multispecific antibodies (e.g., bispecific antibodies), antibody fragments, antibody derivatives, antibody analogs, or fusion proteins, etc., as long as they exhibit the desired antigen-binding activity.

As used herein, the term "antibody" or "immunoglobulin," whether referring to a heavy chain antibody or a conventional four-chain antibody herein, is used as general term to include full-length antibodies, their individual chains, and all portions, domains, or fragments thereof (including, but not limited to, antigen-binding domains or fragments, such as the VHH domain or the VH/VL domains, respectively). In addition, the term "sequence" (such as in terms "immunoglobulin sequence." "antibody sequence," "single variable domain sequence." "VHH sequence." or "protein sequence," etc.) generally should be understood to comprise both the relevant amino acid sequence and the nucleic acid sequence or nucleotide sequence encoding said sequence, unless a more limited interpretation is required herein.

As used herein, the term "domain" (of a polypeptide or protein) refers to a folded protein structure that can maintain its tertiary structure independently of the rest of the protein. Generally, domains are responsible for a single functional property of a protein, and in many cases, domains can be added, removed, or transferred to other proteins without losing the function of the rest of the protein and/or the domain.

As used herein, the term "immunoglobulin domain" refers to a globular region of an antibody chain (e.g., the chain of a conventional four-chain antibody or the chain of a heavy chain antibody), or refers to a polypeptide that is essentially composed of such a globular region. Immunoglobulin domains are characterized by their maintenance of the immunoglobulin fold characteristic of the antibody molecule.

As used herein, the term "immunoglobulin variable domain" refers to an immunoglobulin domain that is essentially composed of four "framework regions" known in the art and hereinafter as "Framework Region 1" or "FR1," "Framework Region 2" or "FR2." "Framework Region 3" or "FR3." and "Framework Region 4" or "FR4." wherein said framework regions are separated by three "complementarity-determining regions" or "CDRs" known in the art and hereinafter as "Complementarity-Determining Region 1" or "CDR1." "Complementarity-Determining Region 2" or "CDR2." and "Complementarity-Determining Region 3" or "CDR3." Thus, the general structure or sequence of an immunoglobulin variable domain can be represented as: FR1-CDR1-FR2-CDR2-FR3-CDR3-FR4. The immunoglobulin variable domain is endowed with the specificity of the antibody against the antigen due to its antigen-binding site.

Methods for numbering the amino acid residues of VH domain are known in the art, and these methods can also be similarly applied to VHH domains. For example, the methods comprise the Chothia numbering based on the three-dimensional structure of the antibody and the topology of the CDR loops (Chothia et al. (1989) Nature 342:877-883: Al-Lazikani et al., "Standard conformations for the canonical structures of immunoglobulins." Journal of Molecular Biology. 273, 927-948 (1997)), the Kabat numbering based on the variability of the antibody sequence (Kabat et al., Sequences of Proteins of Immunological Interest. 4th edition. U.S. Department of Health and Human Services. National Institutes of Health (1987)), the AbM numbering (University of Bath), the Contact numbering (University College London), the International ImMunoGeneTics database (IMGT numbering) (1999 Nucleic Acids Research. 27, 209-212), and the North numbering based on affinity propagation clustering using a large number of crystal structures. The variable regions and CDRs in antibody sequences can be identified according to the general rules developed in the art (as mentioned above, for example, the AbM numbering scheme) or by comparing the sequences with a database of known variable regions. The precise amino acid sequence boundaries of the CDRs of the variable regions of the antibodies provided by the disclosure can be determined by those skilled in the art according to any scheme in the art (for example, different numbering schemes or combinations).

It should be noted that the boundaries of the CDRs of the variable regions of the same antibody obtained based on different numbering schemes may vary. That is, the CDR sequences of the same antibody variable region defined under different numbering schemes are different. Therefore, when involving the use of specific CDR sequences of antibodies defined by the disclosure, the scope of the antibody also encompasses such antibodies whose variable region sequences contain the specific CDR sequences, but due to the use of different schemes (for example, different numbering schemes or combinations), the claimed CDR boundaries are different from the specific CDR boundaries defined by the disclosure. Unless otherwise stated, all CDR amino acid residues in immunoglobulin variable domains described herein are numbered and located according to the AbM numbering scheme.

As used herein, the term "immunoglobulin single variable domain" or "single variable domain" refers to an immunoglobulin variable domain that can specifically bind to an antigenic epitope without pairing with another immunoglobulin variable domain. Typically, in conventional immunoglobulins, the heavy chain variable domain (VH) and the light chain variable domain (VL) interact to form the antigen-binding site. In contrast, an immunoglobulin single variable domain can specifically bind to an antigenic epitope without pairing with another immunoglobulin variable domain. Therefore, an example of the immunoglobulin single variable domain described herein is a "single-domain antibody," such as the immunoglobulin single variable domains VH and VL (VH and VL domains): another example of the immunoglobulin single variable domain is a "VHH domain" of camelids as defined below (or simply referred to as "VHH").

The "VHH domain," also known as heavy chain single-domain antibody, VHH, VHH antibody fragment, VHH antibody, or sdAb, is the variable domain of the antigen-binding immunoglobulin known as "heavy chain antibody (HCab)" (i.e., "antibody lacking light chains"). The term "VHH domain" is used to distinguish this variable domain from the heavy chain variable domain present in conventional four-chain antibodies (referred to herein as "VH domain") and the light chain variable domain present in conventional four-chain antibodies (referred to herein as "VL domain"). The VHH domain specifically binds to epitopes without the cooperation of other antigen-binding domains (which is in contrast to the VH or VL domains in conventional four-chain antibodies, wherein the epitope is recognized together with the VL domain and VH domain). The VHH domain is a small, stable, and efficient antigen recognition unit formed by a single immunoglobulin domain.

In the context of this disclosure, the terms "heavy chain single-domain antibody," "VHH domain." "VHH," "VHH antibody fragment." "VHH antibody," and "sdAb" are used interchangeably.

The VHH domain (which has been naturally "designed" to functionally bind to antigens in the absence of a light chain variable domain and without interacting with a light chain variable domain) can be used as a single, relatively small functional antigen-binding structural unit, domain, or polypeptide. This characteristic distinguishes the VHH domain from the VH and VL domains of conventional four-chain antibodies. These VH and VL domains themselves are generally not suitable for practical application as single antigen-binding proteins or immunoglobulin single variable domains and need to be combined in certain form or another form to provide a functional antigen-binding unit (e.g., in the form of conventional antibody fragments such as Fab fragments; or in the form of scFv composed of a VH domain covalently linked to a VL domain).

Due to these unique properties, the use of the VHH domain-alone or as a part of a larger polypeptide—provides many significant advantages over the use of conventional VH and VL domains, scFv, or conventional antibody fragments (e.g., Fab or F(ab')$_2$ fragments): only a single domain is required to bind antigens with a high affinity and a high selectivity, thus eliminating the need for the presence of two separate domains and the need to ensure that these two domains are in the proper spatial conformation and configuration (for example, scFv generally requires the use of a specially designed linker); the VHH domain can be expressed from a single gene and does not require post-translational folding or modification; the VHH domain can be easily engineered into multivalent and multispecific (formatting); the VHH domain is highly soluble and do not have a tendency to aggregate; the VHH domain is highly stable to heat, pH, proteases, and other denaturing agents or conditions, and therefore can be prepared, stored, or transported without the need for refrigeration equipment, thereby achieving cost, time, and environmental savings; the VHH domain is easy to prepare and relatively inexpensive, even on a scale required for production; the VHH domain is relatively small (approximately 15 kDa or one-tenth the size of a conventional IgG) than conventional four-chain antibodies and antigen-binding fragments thereof, thus showing a relatively higher tissue permeability and the ability to be administered at higher doses compared to conventional four-chain antibodies and antigen-binding fragments thereof; the VHH domain can exhibit so-called cavity-binding properties (especially due to its extended CDR3 loop compared to conventional VH domains), so that they can access targets and epitopes that are inaccessible to conventional four-chain antibodies and antigen-binding fragments thereof.

The heavy chain single-domain antibodies disclosed herein can be prepared by those skilled in the art according to known methods in the art or any future methods. Methods for obtaining VHH that binds to a specific antigen or epitope have previously been disclosed in, for example, the following documents: R. van der Linden et al., Journal of Immunological Methods, 240(2000)185-195; Li et al., J Biol Chem., 287(2012)13713-13721; Deffar et al., African Journal of Biotechnology, Vol. 8, (12), pp. 2645-2652, 17 Jun., 2009 and WO94/04678.

The present disclosure is not limited in terms of the origin of the immunoglobulin single variable domain sequence (or of the nucleotide sequence used to express it), nor in terms of the way in which the immunoglobulin single variable domain sequence or nucleotide sequence is (or has been) generated or obtained. The present disclosure can use immunoglobulin sequences from different origins, such as camelid immunoglobulin sequences. The present disclosure also includes fully human, humanized, or chimeric sequences. For example, the present disclosure includes camelid immunoglobulin sequences, humanized camelid immunoglobulin sequences, and chimeric sequences wherein the single variable domain sequence is derived from camelid immunoglobulin and the constant region sequence (e.g., the Fc domain) is derived from a human immunoglobulin. In addition, the present disclosure also uses fused immunoglobulin sequences to form, for example, multivalent and/or multispecific antigen-binding molecules; and immuno-globulin sequences containing labels or other functional portions (e.g., biologically active compounds or peptides, detectable labels, water-soluble polymers, etc.) derived from the immunoglobulin sequences of the present disclosure.

When the most effective animal-derived immunoglobulin is identified, its amino acid sequence can be optimized, for example, by affinity maturation or humanization.

The VHH domain derived from camelids can be "human-ized" (also referred to herein as "sequence optimization") by replacing one or more amino acid residues in the original VHH sequence with one or more amino acid residues present at the corresponding positions in the VH domain of a human conventional four-chain antibody. In addition to humanization, "sequence optimization" can also encompass other modifications to the sequence that provide improved properties for the VHH, such as increased transient trans-fection expression yield. Humanization can prevent an immune response in humans to animal-derived VHH. The humanized VHH domain may contain one or more fully human framework region sequences. Humanization can be carried out in a manner known in the art, which is clear to those skilled in the art, for example, based on the further description herein and the prior art (e.g., WO2008/020079). In addition, it should be noted that such humanized VHH can be obtained in any suitable manner known in the art and is therefore not strictly limited to peptides obtained using naturally occurring VHH domains as starting materials.

As used herein, the term "thymic stromal lymphopoietin" or "TSLP" refers to a protein belonging to the cytokine family and is known to be involved in type 2 inflammation through the activation of dendritic cells, mast cells, and ILC2. The signaling of TSLP are performed through a heterodimeric receptor complex composed of the thymic stromal lymphopoietin receptor TSLPR and the IL-7Ra chain. After TSLP binds to this heterodimeric receptor complex, the phosphorylation of STAT5 is induced, thereby in turn leading to downstream gene expression.

As used herein, the term "interleukin-33" or "IL-33" is a tissue-derived nuclear cytokine from the IL-1 family. After being processed by proteases of mast cell or certain allergens with enzymatical activity, IL-33 directly activates locally infiltrating basophils, mast cells, ILC2 cells, T cells, and eosinophils to induce type 2 inflammatory responses. IL-33 activates the NF-κB and MAPK signaling pathways by binding to the complex receptor composed of ST2 and IL-TRAcP, thereby stimulating target cells and leading to a series of immune responses, including the production of cytokines and chemokines by target cells.

In general, the term "specificity" refers to the non-random binding interaction between two molecules, such as a par-ticular antigen and its natural receptor, and/or a particular antigen and an antigen-binding molecule (e.g., the immu-noglobulin single variable domain, heavy chain single-domain antibody, TSLP-binding molecule, or IL-33-binding molecule of the present disclosure). The specificity can be determined based on the affinity and/or avidity of the anti-gen-binding molecule. The affinity, represented by the equi-librium dissociation constant ($K_D$) of the antigen and the antigen-binding molecule, is a measure of the strength of the binding between the epitope and the antigen-binding site on the antigen-binding molecule: the smaller the $K_D$ value, the stronger the binding strength between the epitope and the antigen-binding molecule (or, affinity can also be expressed as the association constant ($K_A$), which is $1/K_D$). As those skilled in the art will understand, depending on the specific antigen of interest, affinity can be measured in known ways.

Avidity is a measure of the strength of the binding between an antigen-binding molecule (e.g., immunoglobulin, anti-body, immunoglobulin single variable domain, or peptide containing the same) and the relevant antigen. Avidity is related to both the affinity between the antigen-binding site on the antigen-binding molecule and the relevant antigen, and the number of relevant binding sites present on the antigen-binding molecule.

As used herein, the ability to "block" refers to the ability of an antigen-binding molecule to inhibit the specific bind-ing interaction between two molecules (e.g., a particular target antigen and its natural receptor, such as TSLP and TSLPR and/or IL-7Rα, and/or IL-33 and ST2 and/or IL-1RAcP) to any detectable extent. In some embodiments, an antigen-binding molecule that blocks the specific binding interaction between two molecules inhibits the binding interaction between the two molecules by at least 50%. In some embodiments, the inhibition can be greater than 60%, greater than 70%, greater than 80%, or greater than 90%.

The term "TSLP-binding molecule" as used herein refers to any molecule that can specifically bind to thymic stromal lymphopoietin (TSLP) and block the binding interaction between TSLP and TSLPR and/or IL-7Rα. In some cases, the "TSLP-binding molecule" may comprise at least one immunoglobulin single variable domain that binds to TSLP and blocks the binding interaction between TSLP and TSLPR and/or IL-7Rα as defined herein, such as an VHH.

The term "IL-33-binding molecule" as used herein refers to any molecule that can specifically bind to interleukin-33 (IL-33) and block the binding interaction between IL-33 and ST2 and/or IL-1RAcP. In some cases, the "IL-33-binding molecule" may comprise at least one immunoglobulin single variable domain that binds to IL-33 and blocks the binding interaction between IL-33 and ST2 and/or IL-1RAcP as defined herein, such as an VHH.

In some embodiments, the "TSLP-binding molecule" or "IL-33-binding molecule" as used herein may each inde-pendently contain 2, 3, 4, or more immunoglobulin single variable domains that bind to the target antigen, such as an VHH.

As used herein, the term "valency" refers to the presence of a specified number of antigen-binding sites in a given molecule. The term "monovalent" refers to an antigen-binding molecule that has only a single antigen-binding site; and the term "multivalent" refers to an antigen-binding molecule that has multiple antigen-binding sites. Accord-ingly, the terms "bivalent," "tetravalent," and "hexavalent" respectively indicate the presence of 2, 4, and 6 binding sites in the antigen-binding molecule. In some embodiments, the TSLP-binding molecule or IL-33-binding molecule pro-vided herein is bivalent.

In some embodiments, the "TSLP-binding molecule" or "IL-33-binding molecule" of the invention also encom-passes multispecific antigen-binding molecules, which com-prise at least one immunoglobulin single variable domain that specifically binds to TSLP and blocks the binding interaction between TSLP and TSLPR and/or IL-7Rα, and/ or at least one immunoglobulin single variable domain that specifically binds to IL-33 and blocks the binding interaction between IL-33 and ST2 and/or IL-1RAcP, and further com-prise antigen-binding domains or immunoglobulin single variable domains that bind to different antigens or different regions of the same antigen (e.g., different epitopes).

In some embodiments, the present disclosure also encom-passes "TSLP/IL-33 bispecific antigen-binding molecules," which contain at least one immunoglobulin single variable domain that specifically binds to TSLP and blocks the binding interaction between TSLP and TSLPR and/or IL-7Rα, and at least one immunoglobulin single variable domain that specifically binds to IL-33 and blocks the binding interaction between IL-33 and ST2 and/or IL-1RAcP.

In addition to the immunoglobulin single variable domains that bind to the targeted antigens, the "TSLP-binding molecule," "IL-33-binding molecule," and/or "TSLP/IL-33 bispecific antigen-binding molecule" of the present disclosure may also comprise linkers and/or functional portions, such as biologically active compounds or polypeptides (e.g., Fc domains) and/or conjugates that can modulate (e.g., increase or decrease) the natural activity of the antigen-binding molecule or confer new activities on the molecule.

As used herein, the term "isolated" generally refers to a biological material (e.g., a virus, nucleic acid, or protein) that is substantially free of components that normally accompany or interact with it in its naturally occurring environment. The isolated biological material may optionally contain additional materials that are not found in its natural environment (e.g., nucleic acids or proteins). Herein, when referring to proteins, "isolated" generally means that the molecule is separated and isolated from the whole organism in which the molecule naturally exists, or that it is essentially free of other biological macromolecules of the same type. When referring to nucleic acid molecules, it is completely or partially separated from the sequences with which it is naturally associated, or the nucleic acid has heterologous sequences associated with it, or the nucleic acid is separated from the chromosome.

As used herein, the terms "polypeptide" and "protein" are used interchangeably and generally refer to a polymer of amino acid residues. The term also applies to amino acid polymers in which one or more amino acid residues are analogs or mimetics of the corresponding naturally occurring amino acids, as well as naturally occurring amino acid polymers. The term also includes modified amino acid polymers, for example, by adding glycosyl residues to form glycoproteins or by phosphorylation modification. Polypeptides and proteins can be produced by naturally occurring and non-recombinant cells or by genetically engineered or recombinant cells, and can comprise molecules with the amino acid sequence of a natural protein, or molecules with one or more amino acids deleted, added, and/or substituted from the natural sequence. The terms "polypeptide" and "protein" particularly include sequences in which one or more amino acids in the antigen-binding protein described in the present disclosure are deleted, added, and/or substituted.

Amino acid residues will be represented according to the standard three-letter or one-letter amino acid codes known and agreed upon in the art. When comparing two amino acid sequences, the term "amino acid difference" refers to the insertion, deletion, or substitution of a specified number of amino acid residues at a particular position in the reference sequence compared to another sequence. In the case of substitution, the substitution will preferably be a conservative amino acid substitution, which refers to the replacement of an amino acid residue with another amino acid residue of similar chemical structure, which has little or essentially no effect on the function, activity, or other biological properties of the polypeptide. Conservative amino acid substitutions are well known in the art, for example, conservative amino acid substitutions are preferably one amino acid within groups (i) to (v) being replaced by another amino acid within the same group: (i) small aliphatic non-polar or weakly polar residues: Ala, Ser, Thr, Pro, and Gly; (ii) polar negatively charged residues and their (uncharged) amides: Asp, Asn, Glu, and Gln; (iii) polar positively charged residues: His, Arg, and Lys; (iv) larger aliphatic non-polar residues: Met, Leu, Ile, Val, and Cys; and (v) aromatic residues: Phe, Tyr, and Trp. Particularly preferred conservative amino acid substitutions are as follows: Ala substituted by Gly or Ser; Arg substituted by Lys; Asn substituted by Gln or His; Asp substituted by Glu; Cys substituted by Ser; Gln substituted by Asn; Glu substituted by Asp; Gly substituted by Ala or Pro; His substituted by Asn or Gln; Ile substituted by Leu or Val; Leu substituted by Ile or Val; Lys substituted by Arg, Gln, or Glu; Met substituted by Leu, Tyr, or Ile; Phe substituted by Met, Leu, or Tyr; Ser substituted by Thr; Thr substituted by Ser; Trp substituted by Tyr; Tyr substituted by Trp or Phe; or Val substituted by Ile or Leu.

"Sequence identity" between two polypeptide sequences indicates the percentage of identical amino acids between the sequences. "Sequence similarity" indicates the percentage of amino acids that are identical or represent conserved amino acid substitutions. Methods for evaluating the degree of sequence identity between amino acids or nucleotides are known to those skilled in the art. For example, amino acid sequence identity is usually measured using sequence analysis software. For example, the BLAST program in the NCBI database can be used to determine identity. For the determination of sequence identity, see, for example: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987 and Sequence Analysis Primer, Gribskov, M. and Devereux, J., eds., M Stockton Press, New York, 1991.

As used herein, the term "$EC_{50}$," also known as "half-maximum effective concentration," refers to the concentration of a drug, an antibody, or a toxic agent that induces a response of 50% between the baseline and the maximum after a specific exposure time. In the context of the application, the unit of $EC_{50}$ is "μg/mL."

As used herein, the term "operably linked" generally means that at least one nucleic acid molecule and at least one regulatory element are in a functional relationship with each other. For example, if a promoter can initiate or otherwise control/regulate the transcription and/or expression of a coding sequence, the promoter is considered to be "operably linked" to the coding sequence (where the coding sequence should be understood to be "under the control" of the promoter). Typically, when two nucleotide sequences are operably linked, they will be in the same orientation and usually also in the same reading frame. They are also generally substantially contiguous.

As used herein, the term "subject" includes any animal, and more specifically, mammals. Among mammals, humans and non-human mammals can be distinguished. Non-human animals can be, for example, companion animals (e.g., dogs, cats, etc.), livestock (e.g., cattle, pigs, horses, sheep, goats, etc.), and experimental animals commonly used for research purposes and/or for the production of antibodies (e.g., rats, mice, guinea pigs, non-human primates (such as *Macaca fascicularis*), or camelids, etc.). In the context of prophylactic and/or therapeutic purposes, the subject is preferably a human.

As used herein, the terms "prevent," "preventing," and "prevention" refer to the method of preventing or delaying the occurrence of a disease or condition or symptom (e.g., inflammatory disease) in a subject. The terms "treat," "treating," and "treatment" refer to obtaining the desired pharmacological and/or physiological effect. The effect can be prophylactic in terms of completely or partially preventing the disease or its symptoms, and/or therapeutic in terms of partially or completely curing the disease and/or adverse effects caused by the disease. The "treatment" used herein encompasses diseases in mammals, particularly humans, and includes: (a) preventing the occurrence of a disease or condition in an individual who is susceptible to the disease but has not yet been diagnosed with the disease; (b) inhibiting the disease, such as arresting the progression of the disease; or (c) alleviating the disease, such as alleviating the symptoms associated with the disease. The "treatment" used herein includes the administration of drugs or compounds to individuals to treat, cure, alleviate, improve, mitigate, or inhibit the disease of the individual, including but not limited to administering drugs containing the compounds described herein to individuals in need.

As used herein, the term "effective amount" refers to the amount sufficient to achieve or at least partially achieve the desired effect. For example, an effective amount for preventing disease refers to the amount sufficient to prevent, stop, or delay the occurrence of the disease; an effective amount for treating disease refers to the amount sufficient to cure or at least partially prevent the disease and its complications in patients who already affected with the disease. Determining such an effective amount is well within the capabilities of those skilled in the art. For example, the effective amount for therapeutic use will depend on the severity of the disease to be treated, the overall state of the patient's own immune system, the patient's general condition such as age, weight, and gender, the route of administration of the drug, and other treatments administered concurrently, etc.

As used herein, the term "pharmaceutical composition" can be used for the treatment of disease, as well as in vitro cell culture experiments. When used for the treatment of disease, the term "pharmaceutical composition" usually refers to a unit dose form and can be prepared by any of the well-known methods in the pharmaceutical field. All methods include the step of combining the active ingredient with excipients that constitute one or more auxiliary components. Typically, the composition is prepared by uniformly and thoroughly combining the active compound with liquid excipients, finely divided solid excipients, or both.

The present disclosure aims to provide novel drugs for the treatment, prevention, or alleviation of inflammatory diseases (e.g., type 2 inflammatory diseases, typically such as asthma and atopic dermatitis).

In some embodiments, the present disclosure relates to TSLP-binding molecules, IL-33-binding molecules, and bispecific antigen-binding molecules simultaneously targeting TSLP and IL-33. The TSLP-binding molecules and IL-33-binding molecules can more effectively block the binding of human TSLP or human IL-33 with their receptors and inhibit their signaling than anti-TSLP antibodies (such as Tezepelumab) and anti-IL-33 antibodies (such as Itepekimab and Etokimab) in the prior art. The bispecific antigen-binding molecules can more effectively regulate type 2 inflammatory responses than the use of TSLP antibodies or IL-33 antibodies alone.

TSLP-Binding Molecules

The TSLP-binding molecules provided by the present disclosure can more effectively block the binding of human TSLP to the complex of TSLPR and IL-7Rα than anti-TSLP antibodies in the prior art (such as Tezepelumab), thereby providing biological activities, including, for example, inhibiting the production of Th2-type cytokines and thus alleviating inflammatory responses.

Therefore, in some aspects, the present disclosure provides a TSLP-binding molecule, which comprises at least one immunoglobulin single variable domain specifically binding to TSLP.

In some embodiments, the at least one immunoglobulin single variable domain specifically binding to TSLP may comprise a CDR1, a CDR2 and a CDR3 in the VHH as shown in SEQ ID NO: 4, 8, 12, 16, 20, 24, 28, 32, 36, 40, 44, 48, 52, 56, 60 or 64. The CDRs may be defined according to any of the following definition systems: Kabat CDR, AbM CDR, Chothia CDR, or IMGT CDR.

In some embodiments, the at least one immunoglobulin single variable domain specifically binding to TSLP comprises a CDR1, a CDR2, and a CDR3 selected from any one or more of the following groups defined according to the AbM numbering system:

1) a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3;

2) a CDR1 comprising the amino acid sequence set forth in SEQ ID NO: 5, a CDR2 comprising the amino acid sequence set forth in SEQ ID NO: 6, and a CDR3 comprising the amino acid sequence set forth in SEQ ID NO: 7;

3) a CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11;

4) a CDR1 comprising the amino acid sequence set forth in SEQ ID NO: 13, a CDR2 comprising the amino acid sequence set forth in SEQ ID NO: 14, and a CDR3 comprising the amino acid sequence set forth in SEQ ID NO: 15;

5) a CDR1 comprising the amino acid sequence set forth in SEQ ID NO: 17, a CDR2 comprising the amino acid sequence set forth in SEQ ID NO: 18, and a CDR3 comprising the amino acid sequence set forth in SEQ ID NO: 19;

6) a CDR1 comprising the amino acid sequence set forth in SEQ ID NO: 21, a CDR2 comprising the amino acid sequence set forth in SEQ ID NO: 22, and a CDR3 comprising the amino acid sequence set forth in SEQ ID NO: 23;

7) a CDR1 comprising the amino acid sequence set forth in SEQ ID NO: 25, a CDR2 comprising the amino acid sequence set forth in SEQ ID NO: 26, and a CDR3 comprising the amino acid sequence set forth in SEQ ID NO: 27;

8) a CDR1 comprising the amino acid sequence set forth in SEQ ID NO: 29, a CDR2 comprising the amino acid sequence set forth in SEQ ID NO: 30, and a CDR3 comprising the amino acid sequence set forth in SEQ ID NO: 31;

9) a CDR1 comprising the amino acid sequence set forth in SEQ ID NO: 33, a CDR2 comprising the amino acid sequence set forth in SEQ ID NO: 34, and a CDR3 comprising the amino acid sequence set forth in SEQ ID NO: 35;

10) a CDR1 comprising the amino acid sequence set forth in SEQ ID NO: 37, a CDR2 comprising the amino acid sequence set forth in SEQ ID NO: 38, and a CDR3 comprising the amino acid sequence set forth in SEQ ID NO: 39;

11) a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43;

12) a CDR1 comprising the amino acid sequence set forth in SEQ ID NO: 45, a CDR2 comprising the amino acid sequence set forth in SEQ ID NO: 46, and a CDR3 comprising the amino acid sequence set forth in SEQ ID NO: 47;

13) a CDR1 comprising the amino acid sequence set forth in SEQ ID NO: 49, a CDR2 comprising the amino acid sequence set forth in SEQ ID NO: 50, and a CDR3 comprising the amino acid sequence set forth in SEQ ID NO: 51;

14) a CDR1 comprising the amino acid sequence set forth in SEQ ID NO: 53, a CDR2 comprising the amino acid sequence set forth in SEQ ID NO: 54, and a CDR3 comprising the amino acid sequence set forth in SEQ ID NO: 55;

15) a CDR1 comprising the amino acid sequence set forth in SEQ ID NO: 57, a CDR2 comprising the amino acid sequence set forth in SEQ ID NO: 58, and a CDR3 comprising the amino acid sequence set forth in SEQ ID NO: 59; or 16) a CDR1 comprising the amino acid sequence set forth in SEQ ID NO: 61, a CDR2 comprising the amino acid sequence set forth in SEQ ID NO: 62, and a CDR3 comprising the amino acid sequence set forth in SEQ ID NO: 63.

In some preferred embodiments, the at least one immunoglobulin single variable domain specifically binding to TSLP comprises a CDR1, a CDR2 and a CDR3 in the VHH as shown in SEQ ID NO: 8, 24, 32, 40, 44, 48, 52, 56, 60 or 64. The CDRs may be defined according to any of the following definition systems: Kabat CDR, AbM CDR, Chothia CDR, or IMGT CDR.

In some preferred embodiments, the at least one immunoglobulin single variable domain specifically binding to TSLP comprises a CDR1, a CDR2, and a CDR3 selected from any one or more of the following groups defined according to the AbM numbering system:

1) a CDR1 comprising the amino acid sequence set forth in SEQ ID NO: 5, a CDR2 comprising the amino acid sequence set forth in SEQ ID NO: 6, and a CDR3 comprising the amino acid sequence set forth in SEQ ID NO: 7;

2) a CDR1 comprising the amino acid sequence set forth in SEQ ID NO: 21, a CDR2 comprising the amino acid sequence set forth in SEQ ID NO: 22, and a CDR3 comprising the amino acid sequence set forth in SEQ ID NO: 23;

3) a CDR1 comprising the amino acid sequence set forth in SEQ ID NO: 29, a CDR2 comprising the amino acid sequence set forth in SEQ ID NO: 30, and a CDR3 comprising the amino acid sequence set forth in SEQ ID NO: 31;

4) a CDR1 comprising the amino acid sequence set forth in SEQ ID NO: 37, a CDR2 comprising the amino acid sequence set forth in SEQ ID NO: 38, and a CDR3 comprising the amino acid sequence set forth in SEQ ID NO: 39;

5) a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43;

6) a CDR1 comprising the amino acid sequence set forth in SEQ ID NO: 45, a CDR2 comprising the amino acid sequence set forth in SEQ ID NO: 46, and a CDR3 comprising the amino acid sequence set forth in SEQ ID NO: 47;

7) a CDR1 comprising the amino acid sequence set forth in SEQ ID NO: 49, a CDR2 comprising the amino acid sequence set forth in SEQ ID NO: 50, and a CDR3 comprising the amino acid sequence set forth in SEQ ID NO: 51;

8) a CDR1 comprising the amino acid sequence set forth in SEQ ID NO: 53, a CDR2 comprising the amino acid sequence set forth in SEQ ID NO: 54, and a CDR3 comprising the amino acid sequence set forth in SEQ ID NO: 55;

8) a CDR1 comprising the amino acid sequence set forth in SEQ ID NO: 57, a CDR2 comprising the amino acid sequence set forth in SEQ ID NO: 58, and a CDR3 comprising the amino acid sequence set forth in SEQ ID NO: 59; or 10) a CDR1 comprising the amino acid sequence set forth in SEQ ID NO: 61, a CDR2 comprising the amino acid sequence set forth in SEQ ID NO: 62, and a CDR3 comprising the amino acid sequence set forth in SEQ ID NO: 63.

In some embodiments, the TSLP-binding molecule provided by the present disclosure comprises at least one immunoglobulin single variable domain specifically binding to TSLP, said at least one immunoglobulin single variable domain specifically binding to TSLP comprises the amino acid sequence set forth in SEQ ID NO: 4, 8, 12, 16, 20, 24, 28, 32, 36, 40, 44, 48, 52, 56, 60 or 64, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 4, 8, 12, 16, 20, 24, 28, 32, 36, 40, 44, 48, 52, 56, 60 or 64, and maintaining the specific binding to TSLP.

In some preferred embodiments, said at least one immunoglobulin single variable domain specifically binding to TSLP comprises the amino acid sequence set forth in SEQ ID NO: 8, 24, 32, 40, 44, 48, 52, 56, 60 or 64, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 8, 24, 32, 40, 44, 48, 52, 56, 60 or 64, and maintaining the specific binding to TSLP.

In some embodiments, the immunoglobulin single variable domain specifically binding to TSLP is a VHH, such as a VHH derived from a camelid, the camelid preferably is an alpaca or a llama.

In some preferred embodiments, the immunoglobulin single variable domain specifically binding to TSLP is a humanized VHH. A humanized VHH is desired for its reduced immunogenicity in human. Said humanized VHH comprises the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 44. In some embodiments, the amino acid sequence of the humanized VHH comprises one or more amino acid substitutions compared to SEQ ID NO: 44, preferably conservative amino acid substitutions. For example, the amino acid sequence of the humanized immunoglobulin single variable domain comprises 1, 2, 3, 4, 5, 6, 7, 8, 9, or 10 conservative amino acid substitutions compared to SEQ ID NO: 44. In some preferred embodiments, the humanized VHH comprises the amino acid sequence set forth in any one of SEQ ID NOs: 65-78, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in any one of SEQ ID NOs: 65-78, and maintaining the specific binding to TSLP.

In some embodiments, the TSLP-binding molecule is an anti-TSLP antibody or antigen-binding fragment thereof. In a further embodiment, the TSLP-binding molecule is a heavy chain antibody, a heavy chain single domain antibody, a chimeric antibody or a humanized antibody.

IL-33-Binding Molecule

The IL-33 binding molecules provided by the present disclosure can more effectively block the binding of human IL-33 to the complex of ST2 and IL-1RAcP than anti-IL-33 antibodies in the prior art (such as Itepekimab and Etokimab), thereby providing biological activities, including, for example, inhibiting the production of Th2-type cytokines and thus alleviating inflammatory responses.

Therefore, in some aspects, the present disclosure provides an IL-33-binding molecule, which comprises at least one immunoglobulin single variable domain specifically binding to IL-33.

In some embodiments, the at least one immunoglobulin single variable domain specifically binding to IL-33 may comprise a CDR1, a CDR2, and a CDR3 in the VHH as shown in SEQ ID NO: 82, 86, 90, 94, 98, 102, 106, 110, 114, 118, 122, 126, 130, 134, 138, 142, 146 or 150. The CDRs may be defined according to any of the following definition systems: Kabat CDR, AbM CDR, Chothia CDR, or IMGT CDR.

In some embodiments, the at least one immunoglobulin single variable domain specifically binding to IL-33 comprises a CDR1, a CDR2, and a CDR3 selected from any one or more of the following groups defined according to the AbM numbering system:

1) a CDR1 comprising the amino acid sequence set forth in SEQ ID NO: 79, a CDR2 comprising the amino acid sequence set forth in SEQ ID NO: 80, and a CDR3 comprising the amino acid sequence set forth in SEQ ID NO: 81;

2) a CDR1 comprising the amino acid sequence set forth in SEQ ID NO: 83, a CDR2 comprising the amino acid sequence set forth in SEQ ID NO: 84, and a CDR3 comprising the amino acid sequence set forth in SEQ ID NO: 85;

3) a CDR1 comprising the amino acid sequence set forth in SEQ ID NO: 87, a CDR2 comprising the amino acid sequence set forth in SEQ ID NO: 88, and a CDR3 comprising the amino acid sequence set forth in SEQ ID NO: 89;

4) a CDR1 comprising the amino acid sequence set forth in SEQ ID NO: 91, a CDR2 comprising the amino acid sequence set forth in SEQ ID NO: 92, and a CDR3 comprising the amino acid sequence set forth in SEQ ID NO: 93;

5) a CDR1 comprising the amino acid sequence set forth in SEQ ID NO: 95, a CDR2 comprising the amino acid sequence set forth in SEQ ID NO: 96, and a CDR3 comprising the amino acid sequence set forth in SEQ ID NO: 97;

6) a CDR1 comprising the amino acid sequence set forth in SEQ ID NO: 99, a CDR2 comprising the amino acid sequence set forth in SEQ ID NO: 100, and a CDR3 comprising the amino acid sequence set forth in SEQ ID NO: 101;

7) a CDR1 comprising the amino acid sequence set forth in SEQ ID NO: 103, a CDR2 comprising the amino acid sequence set forth in SEQ ID NO: 104, and a CDR3 comprising the amino acid sequence set forth in SEQ ID NO: 105;

8) a CDR1 comprising the amino acid sequence set forth in SEQ ID NO: 107, a CDR2 comprising the amino acid sequence set forth in SEQ ID NO: 108, and a CDR3 comprising the amino acid sequence set forth in SEQ ID NO: 109;

9) a CDR1 comprising the amino acid sequence set forth in SEQ ID NO: 111, a CDR2 comprising the amino acid sequence set forth in SEQ ID NO: 112, and a CDR3 comprising the amino acid sequence set forth in SEQ ID NO: 113;

10) a CDR1 comprising the amino acid sequence set forth in SEQ ID NO: 115, a CDR2 comprising the amino acid sequence set forth in SEQ ID NO: 116, and a CDR3 comprising the amino acid sequence set forth in SEQ ID NO: 117;

11) a CDR1 comprising the amino acid sequence set forth in SEQ ID NO: 119, a CDR2 comprising the amino acid sequence set forth in SEQ ID NO: 120, and a CDR3 comprising the amino acid sequence set forth in SEQ ID NO: 121;

12) a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125;

13) a CDR1 comprising the amino acid sequence set forth in SEQ ID NO: 127, a CDR2 comprising the amino acid sequence set forth in SEQ ID NO: 128, and a CDR3 comprising the amino acid sequence set forth in SEQ ID NO: 129;

14) a CDR1 comprising the amino acid sequence set forth in SEQ ID NO: 131, a CDR2 comprising the amino acid sequence set forth in SEQ ID NO: 132, and a CDR3 comprising the amino acid sequence set forth in SEQ ID NO: 133;

15) a CDR1 comprising the amino acid sequence set forth in SEQ ID NO: 135, a CDR2 comprising the amino acid sequence set forth in SEQ ID NO: 136, and a CDR3 comprising the amino acid sequence set forth in SEQ ID NO: 137;

16) a CDR1 comprising the amino acid sequence set forth in SEQ ID NO: 139, a CDR2 comprising the amino acid sequence set forth in SEQ ID NO: 140, and a CDR3 comprising the amino acid sequence set forth in SEQ ID NO: 141;

17) a CDR1 comprising the amino acid sequence set forth in SEQ ID NO: 143, a CDR2 comprising the amino acid sequence set forth in SEQ ID NO: 144, and a CDR3 comprising the amino acid sequence set forth in SEQ ID NO: 145; or 18) a CDR1 comprising the amino acid sequence set forth in SEQ ID NO: 147, a CDR2 comprising the amino acid sequence set forth in SEQ ID NO: 148, and a CDR3 comprising the amino acid sequence set forth in SEQ ID NO: 149.

In some embodiments, the at least one immunoglobulin single variable domain specifically binding to IL-33 may comprise a CDR1, a CDR2, and a CDR3 in the VHH as shown in SEQ ID NO: 114 or 126. The CDRs may be defined according to any of the following definition systems: Kabat CDR, AbM CDR, Chothia CDR, or IMGT CDR.

In some embodiments, the at least one immunoglobulin single variable domain specifically binding to IL-33 comprises a CDR1, a CDR2, and a CDR3 selected from any one or more of the following groups defined according to the AbM numbering system:

9) a CDR1 comprising the amino acid sequence set forth in SEQ ID NO: 111, a CDR2 comprising the amino acid sequence set forth in SEQ ID NO: 112, and a CDR3 comprising the amino acid sequence set forth in SEQ ID NO: 113;

12) a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125.

In some embodiments, the IL-33-binding molecule provided by the present disclosure comprises at least one immunoglobulin single variable domain specifically binding to IL-33, and the at least one immunoglobulin single variable domain specifically binding to IL-33 may comprise the amino acid sequence set forth in SEQ ID NO: 82, 86, 90, 94, 98, 102, 106, 110, 114, 118, 122, 126, 130, 134, 138, 142, 146 or 150, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 82, 86, 90, 94, 98, 102, 106, 110, 114, 118, 122, 126, 130, 134, 138, 142, 146 or 150, and maintaining the specific binding to IL-33.

In some preferred embodiments, the at least one immunoglobulin single variable domain specifically binding to IL-33 comprises the amino acid sequence set forth in SEQ ID NO: 114 or 126, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 114 or 126, and maintaining the specific binding to IL-33.

In some embodiments, the immunoglobulin single variable domain specifically binding to IL-33 is a VHH, such as a VHH from camelids, the camelids preferably is alpacas or llamas.

In some preferred embodiments, the immunoglobulin single variable domain specifically binding to IL-33 is a humanized VHH. A humanized VHH is desired for its reduced immunogenicity in human. The humanized VHH comprises the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 126. In some embodiments, the amino acid sequence of the humanized VHH comprises one or more amino acid substitutions compared to SEQ ID NO: 126, preferably conservative amino acid substitutions. For example, the amino acid sequence of the humanized immunoglobulin single variable domain comprises 1, 2, 3, 4, 5, 6, 7, 8, 9, or 10 conservative amino acid substitutions compared to SEQ ID NO: 126. In some preferred embodiments, the humanized VHH comprises the amino acid sequence set forth in any one of SEQ ID NOs: 151-158, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in any one of SEQ ID NOs: 151-158, and maintaining the specific binding to IL-33.

In some embodiments, the IL-33-binding molecule is an anti-IL-33 antibody or antigen-binding fragment thereof. In a further embodiment, the IL-33-binding molecule is a heavy chain antibody, a heavy chain single domain antibody, a chimeric antibody or a humanized antibody.

In some embodiments, the TSLP-binding molecule and/or the IL-33-binding molecule provided by the present disclosure respectively comprise a plurality of immunoglobulin single variable domains specifically binding to targeted antigen. The plurality of immunoglobulin single variable domains may be directly or indirectly connected to each other, thereby generating a multivalent antigen-binding molecule.

In some embodiments, the TSLP-binding molecule and/or the IL-33-binding molecule provided by the present disclosure comprise at least one immunoglobulin single variable domain and further comprise an immunoglobulin Fc domain. The Fc domain that can be used in the present disclosure may be derived from different immunoglobulin subtypes, such as IgG (e.g., IgG1, IgG2, IgG3, or IgG4 subtypes), IgA1, IgA2, IgD, IgE, or IgM. The immunoglobulin Fc domain is preferably a human immunoglobulin Fc domain, such as the Fc domain of human IgG1, IgG2, IgG3, or IgG4. In some embodiments, the TSLP-binding molecule and/or the IL-33-binding molecule provided herein comprise an Fc domain derived from a human IgG1 (the amino acid sequence thereof is as shown in SEQ ID NO: 159). In some embodiments, the TSLP-binding molecule and/or the IL-33-binding molecule provided herein comprise a variant of the Fc domain derived from a human IgG1. In some embodiments, the variant of the Fc domain derived from a human IgG1 comprises one or more mutations selected from $C_{220}A$, $L_{234}A$, $L_{235}A$, $M_{252}Y$, $S_{254}T$, $T_{256}E$, and $K_{447}$del. In some embodiments, the variant of the Fc domain derived from a human IgG1 comprises the $C_{220}A$, $L_{234}A$, and $L_{235}A$ mutations. In some embodiments, the variant of the Fc domain derived from a human IgG1 comprises the $C_{220}A$, $L_{234}A$, $L_{235}A$, $M_{252}Y$, $S_{254}T$, $T_{256}E$, and $K_{447}$del mutations. In some particular embodiments, the amino acid sequence of the variant of the Fc domain derived from a human IgG1 is, for example, as shown in SEQ ID NO: 160 or 217.

In some embodiments, in the TSLP-binding molecule and/or IL-33-binding molecule provided by the present disclosure, the immunoglobulin Fc domain (e.g., the Fc domain of a human IgG1) may be directly or indirectly connected to the C-terminus and/or N-terminus of the immunoglobulin single variable domain via a hinge region or a linker. The inclusion of an immunoglobulin Fc domain in the TSLP-binding molecule and/or IL-33-binding molecule provided by the present disclosure can enable the binding molecule to form a dimeric molecule. In some embodiments, the dimer is a homodimer. In some embodiments, the dimer is a heterodimer.

In some particular embodiments, the TSLP-binding molecule and/or IL-33-binding molecule provided by the present disclosure respectively comprise one or more immunoglobulin single variable domains specifically binding to the target antigen, which are directly or indirectly connected via a linker. The immunoglobulin single variable domains specifically binding to the target antigen are directly or indirectly connected to the N-terminus of the immunoglobulin Fc domain via a hinge region or a linker, forming a structure represented as (V)n-Fc, wherein V represents the immunoglobulin single variable domain, n represents the number of immunoglobulin single variable domains that are directly or indirectly connected via a linker, and wherein n≥1.

In some particular embodiments, the TSLP binding molecule and/or IL-33 binding molecule provided by the present disclosure respectively comprise a plurality of immunoglobulin single variable domains specifically binding to the target antigen. The immunoglobulin single variable domains specifically binding to the target antigen are directly or indirectly connected to the N-terminus and/or C-terminus of the immunoglobulin Fc domain via a hinge region or a linker, forming a structure represented as $(V1)_n$-Fc-$(V2)_m$, wherein V1 and V2 represent the immunoglobulin single variable domains, n and m represent the number of immunoglobulin single variable domains that are directly or indirectly connected via a linker, and wherein n≥1.

In some embodiments, when the C-terminus of the immunoglobulin single variable domain provided by the present disclosure is not connected to another domain (such as the Fc domain), in order to reduce the immunogenicity of the immunoglobulin single variable domain, an extension of 1 to 5 amino acids, such as a single alanine extension, may be included at the C-terminus of the immunoglobulin single variable domain.

In some embodiments, the plurality of immunoglobulin variable domains specifically binding to the target antigen in the TSLP-binding molecule and/or IL-33-binding molecule may respectively bind to different regions or different epitopes of the target antigen.

The plurality of immunoglobulin single variable domains, and/or the immunoglobulin single variable domains and the immunoglobulin Fc domain of the present disclosure may be directly connected or indirectly connected via a linker. The linker may be a non-functional amino acid sequence with a length of 1-20 or more amino acids and without secondary or higher structures. For example, the linker is a flexible linker, such as (GS)n, (GGS)n, (GGGS)n, or (GGGGS)n, wherein n is 1, 2, 3, 4, or 5. In some embodiments, the linker is $(GGGGS)_3$. In some embodiments, the linker is $(GGGGS)_4$.

In some embodiments, the TSLP-binding molecule comprises the amino acid sequence set forth in any one of SEQ ID NOs: 161-190, or the amino acid sequence having at least 80%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in any one of SEQ ID NOs: 161-190, and maintaining the specific binding to TSLP.

In some embodiments, the IL-33-binding molecule comprises the amino acid sequence set forth in any one of SEQ ID NOs: 191-216, or the amino acid sequence having at least 80%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in any one of SEQ ID NOs: 191-216, and maintaining the specific binding to IL-33.

Multispecific Antigen-Binding Molecules

In another aspect, the present disclosure also provides a multispecific antigen-binding molecule, which comprises the TSLP-binding molecule and/or the IL-33-binding molecule provided by the present disclosure.

The term "multispecific" refers to the ability of an antigen-binding molecule to specifically bind to various different target antigens or antigen epitopes. For example, "bispecific" means that the antigen-binding molecule can specifically bind to two different target antigens or antigen epitopes.

In some embodiments, in addition to the TSLP-binding molecule and/or the IL-33-binding molecule, the multispecific antigen-binding molecule further comprises one or more additional antigen-binding functional regions that bind to different antigens or different epitopes of the same antigen compared to the TSLP-binding molecule and/or the IL-33-binding molecule.

Bispecific Antigen-Binding Molecules

In another aspect, the present disclosure also provides a TSLP×IL-33 bispecific antigen-binding molecule, which can simultaneously target both TSLP and IL-33, and inhibit or block the signaling of both TSLP and IL-33.

In some embodiments, the bispecific antigen-binding molecule comprises the TSLP-binding molecule and IL-33-binding molecule provided by the present disclosure.

In some embodiments, the bispecific antigen-binding molecule comprises a first antigen-binding functional region and a second antigen-binding functional region, wherein the first antigen-binding functional region comprises at least one immunoglobulin single variable domain specifically binding to TSLP, which comprises:

1) a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3;

2) a CDR1 comprising the amino acid sequence set forth in SEQ ID NO: 5, a CDR2 comprising the amino acid sequence set forth in SEQ ID NO: 6, and a CDR3 comprising the amino acid sequence set forth in SEQ ID NO: 7;

3) a CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11;

4) a CDR1 comprising the amino acid sequence set forth in SEQ ID NO: 13, a CDR2 comprising the amino acid sequence set forth in SEQ ID NO: 14, and a CDR3 comprising the amino acid sequence set forth in SEQ ID NO: 15;

5) a CDR1 comprising the amino acid sequence set forth in SEQ ID NO: 17, a CDR2 comprising the amino acid sequence set forth in SEQ ID NO: 18, and a CDR3 comprising the amino acid sequence set forth in SEQ ID NO: 19;

6) a CDR1 comprising the amino acid sequence set forth in SEQ ID NO: 21, a CDR2 comprising the amino acid sequence set forth in SEQ ID NO: 22, and a CDR3 comprising the amino acid sequence set forth in SEQ ID NO: 23;

7) a CDR1 comprising the amino acid sequence set forth in SEQ ID NO: 25, a CDR2 comprising the amino acid sequence set forth in SEQ ID NO: 26, and a CDR3 comprising the amino acid sequence set forth in SEQ ID NO: 27;

8) a CDR1 comprising the amino acid sequence set forth in SEQ ID NO: 29, a CDR2 comprising the amino acid sequence set forth in SEQ ID NO: 30, and a CDR3 comprising the amino acid sequence set forth in SEQ ID NO: 31;

9) a CDR1 comprising the amino acid sequence set forth in SEQ ID NO: 33, a CDR2 comprising the amino acid sequence set forth in SEQ ID NO: 34, and a CDR3 comprising the amino acid sequence set forth in SEQ ID NO: 35;

10) a CDR1 comprising the amino acid sequence set forth in SEQ ID NO: 37, a CDR2 comprising the amino acid sequence set forth in SEQ ID NO: 38, and a CDR3 comprising the amino acid sequence set forth in SEQ ID NO: 39;

11) a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43;

12) a CDR1 comprising the amino acid sequence set forth in SEQ ID NO: 45, a CDR2 comprising the amino acid sequence set forth in SEQ ID NO: 46, and a CDR3 comprising the amino acid sequence set forth in SEQ ID NO: 47;

13) a CDR1 comprising the amino acid sequence set forth in SEQ ID NO: 49, a CDR2 comprising the amino acid sequence set forth in SEQ ID NO: 50, and a CDR3 comprising the amino acid sequence set forth in SEQ ID NO: 51;

14) a CDR1 comprising the amino acid sequence set forth in SEQ ID NO: 53, a CDR2 comprising the amino acid sequence set forth in SEQ ID NO: 54, and a CDR3 comprising the amino acid sequence set forth in SEQ ID NO: 55;

15) a CDR1 comprising the amino acid sequence set forth in SEQ ID NO: 57, a CDR2 comprising the amino acid sequence set forth in SEQ ID NO: 58, and a CDR3 comprising the amino acid sequence set forth in SEQ ID NO: 59; or 16) a CDR1 comprising the amino acid sequence set forth in SEQ ID NO: 61, a CDR2 comprising the amino acid sequence set forth in SEQ ID NO: 62, and a CDR3 comprising the amino acid sequence set forth in SEQ ID NO: 63; and the second antigen-binding functional region comprises at least one immunoglobulin single variable domain specifically binding to IL-33, which comprises:

1) a CDR1 comprising the amino acid sequence set forth in SEQ ID NO: 79, a CDR2 comprising the amino acid sequence set forth in SEQ ID NO: 80, and a CDR3 comprising the amino acid sequence set forth in SEQ ID NO: 81;

2) a CDR1 comprising the amino acid sequence set forth in SEQ ID NO: 83, a CDR2 comprising the amino acid sequence set forth in SEQ ID NO: 84, and a CDR3 comprising the amino acid sequence set forth in SEQ ID NO: 85;

3) a CDR1 comprising the amino acid sequence set forth in SEQ ID NO: 87, a CDR2 comprising the amino acid sequence set forth in SEQ ID NO: 88, and a CDR3 comprising the amino acid sequence set forth in SEQ ID NO: 89;

4) a CDR1 comprising the amino acid sequence set forth in SEQ ID NO: 91, a CDR2 comprising the amino acid sequence set forth in SEQ ID NO: 92, and a CDR3 comprising the amino acid sequence set forth in SEQ ID NO: 93;

5) a CDR1 comprising the amino acid sequence set forth in SEQ ID NO: 95, a CDR2 comprising the amino acid sequence set forth in SEQ ID NO: 96, and a CDR3 comprising the amino acid sequence set forth in SEQ ID NO: 97;

6) a CDR1 comprising the amino acid sequence set forth in SEQ ID NO: 99, a CDR2 comprising the amino acid sequence set forth in SEQ ID NO: 100, and a CDR3 comprising the amino acid sequence set forth in SEQ ID NO: 101;

7) a CDR1 comprising the amino acid sequence set forth in SEQ ID NO: 103, a CDR2 comprising the amino acid sequence set forth in SEQ ID NO: 104, and a CDR3 comprising the amino acid sequence set forth in SEQ ID NO: 105;

8) a CDR1 comprising the amino acid sequence set forth in SEQ ID NO: 107, a CDR2 comprising the amino acid sequence set forth in SEQ ID NO: 108, and a CDR3 comprising the amino acid sequence set forth in SEQ ID NO: 109;

9) a CDR1 comprising the amino acid sequence set forth in SEQ ID NO: 111, a CDR2 comprising the amino acid sequence set forth in SEQ ID NO: 112, and a CDR3 comprising the amino acid sequence set forth in SEQ ID NO: 113;

10) a CDR1 comprising the amino acid sequence set forth in SEQ ID NO: 115, a CDR2 comprising the amino acid sequence set forth in SEQ ID NO: 116, and a CDR3 comprising the amino acid sequence set forth in SEQ ID NO: 117;

11) a CDR1 comprising the amino acid sequence set forth in SEQ ID NO: 119, a CDR2 comprising the amino acid sequence set forth in SEQ ID NO: 120, and a CDR3 comprising the amino acid sequence set forth in SEQ ID NO: 121;

12) a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125;

13) a CDR1 comprising the amino acid sequence set forth in SEQ ID NO: 127, a CDR2 comprising the amino acid sequence set forth in SEQ ID NO: 128, and a CDR3 comprising the amino acid sequence set forth in SEQ ID NO: 129;

14) a CDR1 comprising the amino acid sequence set forth in SEQ ID NO: 131, a CDR2 comprising the amino acid sequence set forth in SEQ ID NO: 132, and a CDR3 comprising the amino acid sequence set forth in SEQ ID NO: 133;

15) a CDR1 comprising the amino acid sequence set forth in SEQ ID NO: 135, a CDR2 comprising the amino acid sequence set forth in SEQ ID NO: 136, and a CDR3 comprising the amino acid sequence set forth in SEQ ID NO: 137;

16) a CDR1 comprising the amino acid sequence set forth in SEQ ID NO: 139, a CDR2 comprising the amino acid sequence set forth in SEQ ID NO: 140, and a CDR3 comprising the amino acid sequence set forth in SEQ ID NO: 141;

17) a CDR1 comprising the amino acid sequence set forth in SEQ ID NO: 143, a CDR2 comprising the amino acid sequence set forth in SEQ ID NO: 144, and a CDR3 comprising the amino acid sequence set forth in SEQ ID NO: 145; or 18) a CDR1 comprising the amino acid sequence set forth in SEQ ID NO: 147, a CDR2 comprising the amino acid sequence set forth in SEQ ID NO: 148, and a CDR3 comprising the amino acid sequence set forth in SEQ ID NO: 149.

In some embodiments, the immunoglobulin single variable domain specifically binding to TSLP comprises the amino acid sequence set forth in SEQ ID NO: 4, 8, 12, 16, 20, 24, 28, 32, 36, 40, 44, 48, 52, 56, 60, 64, 65, 66, 67, 68, 69, 70, 71, 72, 73, 74, 75, 76, 77 or 78, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 4, 8, 12, 16, 20, 24, 28, 32, 36, 40, 44, 48, 52, 56, 60, 64, 65, 66, 67, 68, 69, 70, 71, 72, 73, 74, 75, 76, 77 or 78, and maintaining the specific binding to TSLP; and the immunoglobulin single variable domain specifically binding to IL-33 comprises the amino acid sequence set forth in SEQ ID NO: 82, 86, 90, 94, 98, 102, 106, 110, 114, 118, 122, 126, 130, 134, 138, 142, 146, 150, 151, 152, 153, 154, 155, 156, 157 or 158, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 82, 86, 90, 94, 98, 102, 106, 110, 114, 118, 122, 126, 130, 134, 138, 142, 146, 150, 151, 152, 153, 154, 155, 156, 157 or 158 and maintaining the specific binding to IL-33.

In some preferred embodiments, the immunoglobulin single variable domain specifically binding to TSLP comprises a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43.

In some preferred embodiments, the immunoglobulin single variable domain specifically binding to TSLP comprises the amino acid sequence set forth in SEQ ID NO: 73, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 73, and maintaining the specific binding to TSLP.

In some preferred embodiments, the immunoglobulin single variable domain specifically binding to IL-33 comprises a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125.

In some preferred embodiments, the immunoglobulin single variable domain specifically binding to IL-33 comprises the amino acid sequence set forth in SEQ ID NO: 154, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 154, and maintaining the specific binding to IL-33.

In some more preferred embodiments, the immunoglobulin single variable domain specifically binding to TSLP comprises a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43; and the immunoglobulin single variable domain specifically binding to IL-33 comprises a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125.

In some more preferred embodiments, the immunoglobulin single variable domain specifically binding to TSLP comprises the amino acid sequence set forth in SEQ ID NO: 73, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 73 and maintaining the specific binding to TSLP; and the immunoglobulin single variable domain specifically binding to IL-33 comprises the amino acid sequence set forth in SEQ ID NO: 154, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 154 and maintaining the specific binding to IL-33.

In some embodiments, the immunoglobulin single variable domain is a VHH, such as a VHH from camelids, the camelids preferably is alpacas or llamas. In some preferred embodiments, the immunoglobulin single variable domain specifically binding to TSLP is a humanized VHH.

In some embodiments, the first antigen-binding functional region is an anti-TSLP antibody or antigen-binding fragment thereof, and/or the second antigen-binding functional region is an anti-IL-33 antibody or antigen-binding fragment thereof. In a further embodiment, the first antigen-binding functional region and the second antigen-binding functional region are each independently a heavy chain antibody, a heavy chain single domain antibody, a chimeric antibody or a humanized antibody.

In some embodiments, the first antigen-binding functional region in the TSLP×IL-33 bispecific antigen-binding molecule provided by the present disclosure comprises a plurality of the immunoglobulin single variable domains specifically binding to TSLP and/or the second antigen-binding functional region comprises a plurality of the immunoglobulin single variable domains specifically binding to IL-33.

The plurality of immunoglobulin single variable domains may be directly or indirectly connected to each other.

In some embodiments, the numbers of the first and second antigen-binding functional regions are each independently 1, 2, or more than 2.

In some embodiments, in addition to the antigen-binding functional regions, the TSLP×IL-33 bispecific antigen-binding molecule provided by the present disclosure further comprises an immunoglobulin Fc domain. The Fc domain used in the present disclosure may be derived from different immunoglobulin subtypes, such as IgG (e.g., IgG1, IgG2, IgG3, or IgG4 subtypes), IgA1, IgA2, IgD, IgE, or IgM. The immunoglobulin Fc domain is preferably a human immunoglobulin Fc domain, such as the Fc domain of human IgG1, IgG2, IgG3, or IgG4. In some embodiments, the TSLP×IL-33 bispecific antigen-binding molecule provided herein comprises an Fc domain derived from a human IgG1 (the amino acid sequence thereof is as shown in SEQ ID NO: 159). In some embodiments, the TSLP×IL-33 bispecific antigen-binding molecule provided herein comprises a variant of the Fc domain derived from a human IgG1. In some embodiments, the variant of the Fc domain derived from a human IgG1 comprises one or more mutations selected from $C_{220}A$, $L_{234}A$, $L_{235}A$, $M_{252}Y$, $S_{254}T$, $T_{256}E$, and $K_{447}del$. In some embodiments, the variant of the Fc domain derived from a human IgG1 comprises the $C_{220}A$, $L_{234}A$, and $L_{235}A$ mutations. In some embodiments, the variant of the Fc domain derived from a human IgG1 comprises the $C_{220}A$, $L_{234}A$, $L_{235}A$, $M_{252}Y$, $S_{254}T$, $T_{256}E$, and $K_{447}del$ mutations. In some particular embodiments, the amino acid sequence of the variant of the Fc domain derived from a human IgG1 is as shown in SEQ ID NO: 160 or 217.

In some embodiments, in the TSLP×IL-33 bispecific antigen-binding molecule provided by the present disclosure, the immunoglobulin Fc domain (e.g., the Fc domain of a human IgG1) is directly or indirectly connected to the C-terminus and/or N-terminus of the first and/or second antigen-binding functional region via a hinge region or a linker. The inclusion of an immunoglobulin Fc domain in the TSLP×IL-33 bispecific antigen-binding molecule provided by the present disclosure can enable the binding molecule to form a dimeric molecule. In some embodiments, the dimer is a homodimer. In some embodiments, the dimer is a heterodimer.

In some particular embodiments, the TSLP×IL-33 bispecific antigen-binding molecule comprises one or more polypeptide chains, which each independently has the structure as shown in V1-L1-V2-Fc-L2-V3 from the N-terminus to the C-terminus, wherein V1, V2, and V3 each independently are absent, the first antigen-binding functional region, or the second antigen-binding functional region, and V1, V2, and V3 comprise at least one the first antigen-binding functional region and at least one the second antigen-binding functional region; L1 and L2 each independently are absent or a linker peptide; Fc is absent or an immunoglobulin Fc segment; and "-" represents a peptide bond.

In a preferred embodiment, the one or more polypeptide chains each independently has the structure as shown in V1-Fc-L1-V2 from the N-terminus to the C-terminus, wherein V1 and V2 are different from each other and each independently are selected from the first antigen-binding functional region or the second antigen-binding functional region, L1 is a linker, and Fc is an immunoglobulin Fc domain; more preferably, V1 and V2 are the first antigen-binding functional region and the second antigen-binding functional region, respectively.

In some embodiments, when the C-terminus of the immunoglobulin single variable domain provided by the present disclosure is not connected to another domain (such as the Fc domain), in order to reduce the immunogenicity of the immunoglobulin single variable domain, an extension of 1 to 5 amino acids, such as a single alanine extension, may be included at the C-terminus of the immunoglobulin single variable domain.

The plurality of immunoglobulin single variable domains, and/or the immunoglobulin single variable domains and the immunoglobulin Fc domain of the present disclosure may be directly or indirectly connected via a linker. The linker may be a non-functional amino acid sequence with a length of 1-20 or more amino acids and without secondary or higher structures. For example, the linker is a flexible linker, such as (GS)n, (GGS)n, (GGGS)n, or (GGGGS)n, wherein n is 1, 2, 3, 4, or 5. In some embodiments, the linker is $(GGGGS)_3$.

In some embodiments, the TSLP×IL-33 bispecific antigen-binding molecule comprises the amino acid sequence set forth in SEQ ID NO: 218, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 218, and maintaining the specific binding to TSLP and IL-33.

Fusion Proteins

In another aspect, the present disclosure also provides a fusion protein, which comprises the TSLP-binding molecule, IL-33-binding molecule, multispecific antigen-binding molecule, and/or bispecific antigen-binding molecule described herein.

In some embodiments, in addition to the TSLP-binding molecule, IL-33-binding molecule, multispecific antigen-binding molecule, and/or bispecific antigen-binding molecule, the fusion protein further comprises one or more additional bioactive proteins. These bioactive proteins can be any protein that has biological, therapeutic, preventive, or diagnostic significance or function. When administered to a subject, they may mediate bioactivity and prevent or alleviate diseases, disorders, or conditions. Specifically, the bioactive proteins can be an agonist, antagonist, modulator, ligand, cytokine, enzyme, or hormone, particularly bioactive proteins that can be used for the treatment, prevention, and/or alleviation of inflammatory diseases.

Conjugates

In another aspect, the present disclosure provides a conjugate, which comprise the TSLP-binding molecule, the IL-33-binding molecule, the multispecific antigen-binding molecule, the bispecific antigen-binding molecule, and/or the fusion protein described herein, and a conjugate that is conjugated thereto.

In this context, the term "conjugation" refers to any method known in the art for functionally connecting protein domains, including but not limited to: recombinant fusion with or without a linker, intein-mediated fusion, non-covalent binding, and covalent bonding, such as disulfide bonding, peptide bonding, hydrogen bonding, electrostatic bonding, and conformational bonding, for example, biotin-avidin binding. In some embodiments, conjugation to an effector can be performed by chemical or recombinant methods, and the chemical method involves forming a covalent bond between two molecules to generate a single molecule.

In this context, the term "conjugate" refers to a component or functional group that can modulate (e.g., increase or decrease) the natural activity of the molecule to which it is attached or confer novel activity on that molecule. In some embodiments, the effector is a biologically active compound or polypeptide, or a non-proteinaceous module, such as a detectable label or a water-soluble polymer.

In some embodiments, the conjugate can be a therapeutic moiety, which refers to a compound or polypeptide that can be used as a therapeutic agent. In some embodiments, the therapeutic moiety comprises therapeutic agents or drugs for the treatment of inflammatory diseases. In some embodiments, the conjugate moiety comprises a β2-adrenergic receptor agonist, antibiotic, anticholinergic, antihistamine, proton pump inhibitor, kinase inhibitor, corticosteroid, etc.

In some embodiments, the conjugate can be a detectable label. The detectable label described by the present disclosure can be any substance that can be detected by fluorescent, spectroscopic, photochemical, biochemical, immunological, electrical, optical, or chemical means. Such labels are well-known in the art, and examples include, but are not limited to, enzymes (e.g., horseradish peroxidase), radioisotopes (e.g., 3H), fluorescent dyes (e.g., fluorescein isothiocyanate (FITC)), luminescent substances (e.g., acridinium ester compounds), magnetic beads, and biotin for binding to avidin (e.g., streptavidin) modified with the above-mentioned labels.

In certain embodiments, the conjugate moiety can be a water-soluble polymer that helps increase the half-life of the antibody. Non-limiting examples of water-soluble polymers include, but are not limited to, polyethylene glycol (PEG), ethylene glycol/propylene glycol copolymers, carboxymethyl cellulose, polyvinyl alcohol, polyvinylpyrrolidone, etc. The polymer can be of any molecular weight and can be branched or unbranched. The number of polymers attached to the antibody can vary, and if more than one polymer is attached, they can be the same or different molecules.

In certain embodiments, the antigen-binding molecules provided herein are used as the substrate for the conjugate.

Variants of Antigen-Binding Molecule

In some embodiments, the antigen-binding molecules provided herein also encompass variants of the amino acid sequences of the antigen-binding molecule provided herein.

In some embodiments, the variants comprise one or more CDR sequences and/or one or more amino acid modifications or substitutions in one or more non-CDR sequences and/or constant regions (e.g., Fc domain) within the immunoglobulin single variable domain provided herein. These variants retain the binding specificity of the parent antibody but possess one or more desired properties conferred by the modifications or substitutions. For example, the variants may have improved antigen-binding affinity, improved glycosylation patterns, reduced risk of glycosylation, reduced deamination, reduced or eliminated effector functions, improved FcRn receptor binding, enhanced pharmacokinetic half-life, pH sensitivity, and/or compatibility for conjugation (e.g., one or more introduced cysteine residues).

Suitable modifications can be introduced into the nucleotide sequences encoding the antibodies using methods known in the art, or the amino acid sequence variants of the antibodies can be prepared by peptide synthesis. Such modifications include, for example, deletions of residues within the antibody's amino acid sequence, and/or insertions and/or substitutions. Any combination of deletions, insertions, and substitutions can be made to achieve the final construct, as long as the final construct has the desired characteristics.

Variants with Substitution, Insertion, and Deletion

In some embodiments, antibody variants with one or more amino acid substitutions are provided. Sites of interest for substitutional mutagenesis include CDRs and FRs. Conservative substitutions are as described above. Amino acid substitutions can be introduced into the antibody of interest, and the resulting product can be screened for desired activities, such as retained/improved antigen binding, reduced immunogenicity, or improved ADCC or CDC.

Some substitutional variants involve replacing one or more residues in the complementarity-determining regions of a parent antibody (e.g., a humanized or human antibody). Generally, the resulting variants selected for further study will have changes (e.g., improvements) in certain biological properties (e.g., increased affinity, reduced immunogenicity) relative to the parent antibody, and/or will substantially retain certain biological properties of the parent antibody. Exemplary substitutional variants are affinity-matured antibodies, which can be conveniently generated using phage display-based affinity maturation techniques such as those described herein. Briefly, one or more CDR residues are mutated, and the variant antibodies are displayed on phage and screened for specific biological activity (e.g., binding affinity).

Changes (e.g., substitutions) can be made to the CDRs, for example, to improve antibody affinity. Such changes can be made to CDR "hotspots," which are residues encoded by codons that undergo mutation at a high frequency during somatic maturation (see, for example, Chowdhury, Methods Mol. Biol. 207:179-196 (2008)), and/or to residues that contact the antigen, wherein the resulting variant VH or VL is tested for the binding affinity. Affinity maturation by construction and reselection of secondary libraries has been described, for example, by Hoogenboom et al., in Methods in Molecular Biology 178:1-37 (O'Brien et al., eds., Human Press, Totowa, NJ, (2001)). In some embodiments of affinity maturation, diversity is introduced into the variable gene selected for maturation by various methods (e.g., error-prone PCR, chain shuffling, or oligonucleotide-directed mutagenesis). A secondary library is then created. The library is then screened to identify any antibody variants with the desired affinity. Another method for introducing diversity involves CDR-directed approaches, in which several CDR residues (e.g., 4-6 residues at a time) are randomized. Residues in the CDRs that are involved in antigen binding can be specifically identified, for example, by alanine scanning mutagenesis or modeling. Specifically, CDR-H3 and CDR-L3 are often targeted.

In some embodiments, substitutions, insertions, or deletions can occur within one or more CDRs, as long as such changes do not substantially reduce the antibody's ability to bind to the antigen. For example, conservative changes (e.g., conservative amino acid substitutions, as provided herein) that do not substantially reduce binding affinity can be made to the CDRs. For example, such changes can be made outside of antigen-contacting residues in the CDRs.

In some further embodiments, the antibodies disclosed herein (e.g., anti-TSLP antibodies, anti-IL-33 antibodies, and multispecific antibodies based thereon) can comprise conservative substitutions or modifications in the amino acids of the heavy chain variable domain. It is understood in the art that certain conservative sequence modifications can be made without eliminating antigen binding (see, for example, Brummell et al. (1993) Biochem 32:1180-8; de Wildt et al. (1997) Prot. Eng. 10:835-41; Komissarov et al. (1997) J. Biol. Chem. 272:26864-26870; Hall et al. (1992) J. Immunol. 149:1605-12; Kelley and O'Connell (1993) Biochem. 32:6862-35; Adib-Conquy et al. (1998) Int. Immunol. 10:341-6; and Beers et al. (2000) Clin. Can. Res. 6:2835-43).

In some embodiments, the immunoglobulin single variable domain of the antigen-binding molecules provided herein comprise one or more amino acid residue substitutions, additions, and/or deletions in one or more CDR sequences and/or one or more FR sequences. In some embodiments, the variants have no more than 20, 15, 10, 9, 8, 7, 6, 5, 4, 3, 2, or 1 substitutions, additions, and/or deletions in total in the CDR sequences and/or FR sequences.

Variants with Glycosylation

In some embodiments, the antigen-binding molecules provided herein also encompass variants with glycosylation to increase or decrease the degree of glycosylation of the antigen-binding molecules. The addition or deletion of glycosylation sites on the antibody can be conveniently achieved by altering the amino acid sequence to create or eliminate one or more glycosylation sites.

In cases where the antibody comprises an Fc domain, the attached carbohydrate can be altered. Natural antibodies generated from mammalian cells typically comprise branched, biantennary oligosaccharides that are generally attached to $N_{297}$ in the CH2 domain of the Fc region via N-linkage. See, for example, Wright et al., TIBTECH 15:26-32 (1997). The oligosaccharides can include various carbohydrates, such as mannose, N-acetylglucosamine (GlcNAc), galactose, and sialic acid, as well as fucose attached to GlcNAc in the "backbone" of biantennary oligosaccharide structure. In some embodiments, the oligosaccharides attached to the antibodies of the present disclosure can be modified to create antibody variants with certain improved properties.

Cysteine-Engineered Antibody Variants

In some embodiments, it may be desirable to create cysteine-engineered antigen-binding molecule, such as "thioMAbs," wherein one or more residues of the antibody are replaced with cysteine residues. In a particular embodiment, the substituted residues are located at accessible sites on the antibody. By substituting those residues with cysteine, reactive thiol groups are thereby positioned at accessible sites on the antibody and can be used to conjugate the antibody to other modules, such as drug module or linker-drug module, to create antibody-drug conjugates, as further described herein. Cysteine-engineered antibodies can be generated as described, for example, in U.S. Pat. No. 7,521,541.

Fc Domain Variants

In some embodiments, one or more amino acid modifications can be introduced into the Fc domain and/or hinge region of the antigen-binding molecules provided herein, thereby generating Fc domain variants. Fc domain variants can comprise a human Fc domain sequence (e.g., human IgG1, IgG2, IgG3, or IgG4 Fc domain) comprising acid modifications (e.g., substitutions) at one or more amino acid positions, for example, to extend the half-life of the antigen-binding molecule, reduce the effector functions of the antigen-binding molecule, facilitate multimerization of bispecific antibodies, and/or improve the manufacturability and drug stability of bispecific antibodies.

In some embodiments, the present disclosure encompasses antibody variants that have some but not all effector functions, making them desirable candidates for applications, wherein the in vivo half-life of the antibody is important, but certain effector functions (such as CDC and ADCC) are unnecessary or detrimental.

In some embodiments, in cases where the effector functions are not desired, the antibodies disclosed herein can be further engineered to introduce at least one mutation in the antibody Fc domain that reduces the antibody's binding to activating Fcγ receptors (FcγRs) and/or reduces Fc effector functions (such as C1q binding, complement-dependent cytotoxicity (CDC), antibody-dependent cell-mediated cytotoxicity (ADCC), or phagocytosis (ADCP)).

Fc domain positions that can be mutated to reduce the antibody's binding to activating FcγRs and subsequently reduce effector functions are those described, for example, in (Xu, Alegre et al. 2000)(Vafa, Gilliland et al. 2014)(Bolt, Routledge et al. 1993)(Chu, Vostiar et al. 2008)(Shields, Namenuk et al. 2001). Fc mutations that have minimal ADCC, ADCP, CDC, and Fc-mediated cell activation have also been described as a mutations of IgG1, IgG2, and IgG4 (Tam, McCarthy et al. 2017).

Exemplary mutations that can be made individually or in combination are $K_{214}T$, $E_{233}P$, $L_{234}V$, $L_{234}A$, $G_{236}$del, $V_{234}A$, $F_{234}A$, $L_{235}A$, $G_{237}A$, $P_{238}A$, $P_{238}S$, $D_{265}A$, $S_{267}E$, $H_{268}A$, $H_{268}Q$, $Q_{268}A$, $N_{297}A$, $A_{327}Q$, $P_{329}A$, $D_{270}A$, $Q_{295}A$, $V_{309}L$, $A_{327}S$, $L_{328}F$, $A_{330}S$ and $P_{331}S$ (according to EU numbering) mutations on IgG1, IgG2, IgG3, or IgG4.

Exemplary combinations of mutations that can be made to reduce ADCC are $L_{234}A/L_{235}A$ on IgG1, $V234A/G_{237}A/P_{238}S/H_{268}A/V_{309}L/A_{330}S/P_{331}S$ on IgG2, $F_{234}A/L_{235}A$ on IgG4, $S_{228}P/F_{234}A/L_{235}A$ on IgG4, $N_{297}A$ on IgG1, IgG2, IgG3, or IgG4, $V_{234}A/G_{237}A$ on IgG2, $K_{214}T/E_{233}P/L_{234}V/L_{235}A/G_{236}$del/$A_{327}G/P_{331}A/D_{365}E/L_{358}M$ on IgG1, $H_{268}Q/V_{309}L/A_{330}S/P_{331}S$ on IgG2, $S_{267}E/L_{328}F$ on IgG1, $L_{234}F/L_{235}E/D_{265}A$ on IgG1, $L_{234}A/L_{235}A/G_{237}A/P_{238}S/H_{268}A/A_{330}S/P_{331}S$ on IgG1, $S_{228}P/F_{234}A/L_{235}A/G_{237}A/P_{238}S$ on IgG4, and $S_{228}P/F_{234}A/L_{235}A/G_{236}$del/$G_{237}A/P_{238}S$ on IgG4. Hybrid IgG2/4 Fc domains, such as Fc with residues 117-260 from IgG2 and residues 261-447 from IgG4 (according to EU numbering), can also be used.

In some embodiments, the present disclosure encompasses antibodies in which the naturally occurring Fc region is modified to extend the half-life of the antibody compared to the parent native antibody in a biological environment, for example, as measured by in vitro assays of serum half-life or half-life.

Exemplary mutations that can be made individually or in combination are $T_{250}Q$, $M_{252}Y$, $I_{253}A$, $S_{254}T$, $T_{256}E$, $P_{257}I$, $T_{307}A$, $D_{376}V$, $E_{380}A$, $M_{428}L$, $H_{433}K$, $N_{434}S$, $N_{434}A$, $N_{434}H$, $N_{434}F$, $H_{435}A$ and $H_{435}R$ (according to EU numbering) mutations.

Exemplary combinations of mutations that can achieve half-life extension are $M_{252}Y/S_{254}T/T_{256}E$, $M_{428}L/N_{434}S$, $T_{250}Q/M_{428}L$, $N_{434}A$, $T_{307}A/E_{380}A/N_{434}A$ (according to EU numbering) on IgG1.

In some embodiments, to avoid light chain mispairing, the present disclosure also encompasses one or more amino acid variants in the hinge region. Exemplary mutations include, for example, $C_{220}A$ (according to EU numbering) in the IgG1 hinge region.

In some embodiments, to avoid protease digestion, the present disclosure also encompasses Fc domain variants with a glycine and/or lysine deletion ($G_{446}$del and/or $K_{447}$del, according to EU numbering) at the C-terminus of the Fc domain.

In some embodiments, the present disclosure encompasses Fc domain variants with one or more amino acid substitutions at the Fc domain interface to help and/or promote Fc domain heterodimerization. These modifications include introducing a protuberance into the first Fc polypeptide and a cavity into the second Fc polypeptide, wherein the protuberance can be positioned in the cavity, thereby promoting the interaction between the first and second Fc polypeptides to form a heterodimer or complex. Methods for producing antibodies with these modifications are known in the art, for example, as described in U.S. Pat. No. 5,731,168.

In some embodiments, the antigen-binding molecules provided herein have the IgG1 isotype and comprise one or more mutations selected from $C_{220}A$, $L_{234}A$, $L_{235}A$, $M_{252}Y$, $S_{254}T$, $T_{256}E$ and $K_{447}$del, or any combination thereof, in the Fc domain. In some embodiments, the antigen-binding molecules provided herein have the IgG1 isotype and comprise the amino acid substitution $L_{234}A/L_{235}A$ (LALA). In some embodiments, the antigen-binding molecules provided herein have the IgG1 isotype and comprise the amino acid substitutions $M_{252}Y/S_{254}T/T_{256}E$ (YTE). In some embodiments, the antigen-binding molecules provided herein comprise an Fc domain comprising the amino acid sequence set forth in SEQ ID NO: 160 or 217, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 160 or 217.

Nucleic Acid Molecules, Vectors, Host Cells

In another aspect, the present disclosure also relates to a nucleic acid molecule encoding the TSLP-binding molecule, the IL-33-binding molecule, the multispecific antigen-binding molecule, the bispecific antigen-binding molecule, and/or the fusion protein described by the present disclosure.

The nucleic acid molecules can be, for example, DNA, RNA, or hybrids thereof, and may also comprise (e.g., chemically) modified nucleotides, such as PNA. The nucleic acid molecules can be single-stranded or double-stranded. In some embodiments, the nucleic acid molecules are in the form of double-stranded DNA. For example, the nucleic acid molecules of the present disclosure can be genomic DNA or cDNA. In certain embodiments, the nucleic acid molecules of the present disclosure are isolated nucleic acid molecules.

The nucleic acid molecules of the present disclosure can also be in the form of vectors, be present in and/or be part of a vector, such as a plasmid, cosmid, or YAC. The vector may particularly be an expression vector, i.e., a vector that provides for the expression of the TSLP-binding molecules, IL-33-binding molecules, multispecific antigen-binding molecules, bispecific antigen-binding molecules, and/or fusion proteins in vitro and/or in vivo (i.e., in a suitable host cell, host organism, and/or expression system). The expression vector typically comprises at least one nucleic acid of the present disclosure operably linked to one or more suitable expression regulatory elements (e.g., promoters, enhancers, terminators, etc.). The selection of the elements and their sequences for expression in a particular host is common knowledge for those skilled in the art. Specific examples of regulatory elements and other elements useful or necessary for the expression of the TSLP-binding molecules, IL-33-binding molecules, multispecific antigen-binding molecules, bispecific antigen-binding molecules, and/or fusion proteins of the present disclosure are, for example, promoters, enhancers, terminators, integration factors, selection markers, leader sequences, reporter genes, etc.

The nucleic acids of the present disclosure can be prepared or obtained by known methods based on the information about the amino acid sequences of the peptides of the present disclosure provided herein (e.g., by automated DNA synthesis and/or recombinant DNA techniques), and/or can be isolated from suitable natural origins.

In another aspect, the present disclosure relates to host cells that express or are capable of expressing one or more TSLP-binding molecules, IL-33-binding molecules, multispecific antigen-binding molecules, bispecific antigen-binding molecules, fusion proteins, and/or host cells that comprise the nucleic acids or vectors of the present disclosure. Suitable host cells or host organisms will be clear to those skilled in the art, and preferred host cells of the present disclosure are bacterial cells, fungal cells, or mammalian cells.

Suitable bacterial cells include cells of Gram-negative bacterial strains (e.g., *Escherichia coli* strains, *Proteus* strains, and *Pseudomonas* strains) and Gram-positive bacterial strains (e.g., *Bacillus* strains, *Streptomyces* strains, *Staphylococcus* strains, and *Lactococcus* strains).

Suitable fungal cells include cells of species from the genera *Trichoderma, Neurospora*, and *Aspergillus*; or cells of species from the genera *Saccharomyces* (e.g., *Saccharomyces cerevisiae*), *Schizosaccharomyces* (e.g., *Schizosaccharomyces pombe*), *Pichia* (e.g., *Pichia pastoris* and *Pichia methanolica*), and *Hansenula*.

Suitable mammalian cells include, for example, HEK293 cells, CHO cells, BHK cells, HeLa cells, or COS cells, and the like.

However, the present disclosure may also use amphibian cells, insect cells, and any other cells known in the art for the expression of heterologous proteins.

The preparation of the TSLP-binding molecules, IL-33-binding molecules, multispecific antigen-binding molecules, bispecific antigen-binding molecules, and/or fusion proteins of the present disclosure can be carried out by transforming/transfecting host cells with the nucleic acid molecules encoding the TSLP-binding molecules, IL-33-binding molecules, multispecific antigen-binding molecules, bispecific antigen-binding molecules, and/or fusion proteins or vectors comprising the nucleic acid molecules, culturing the host cells under conditions suitable for expression of the nucleic acid molecules or vectors, and optionally isolating and/or purifying for one or more times from the host cells or the host cell culture.

Methods and reagents for production purposes, such as specific suitable expression vectors, transformation or transfection methods, selective markers, methods for inducing protein expression, culture conditions, etc., are known in the art. Similarly, protein separation and purification techniques suitable for the methods of manufacturing the TSLP-binding molecules, IL-33-binding molecules, multispecific antigen-binding molecules, bispecific antigen-binding molecules, and/or fusion proteins of the present disclosure are well-known to those skilled in the art.

Compositions

In some aspects, the present disclosure relates to a composition, which comprises at least one of the TSLP-binding molecule, the IL-33-binding molecule, the multispecific antigen-binding molecule, the bispecific antigen-binding molecule, the fusion protein, and/or the conjugate disclosed herein.

In some embodiments, the composition is a pharmaceutical composition, which further comprises at least one pharmaceutically acceptable carrier and/or excipient.

In some embodiments, the pharmaceutical composition may optionally comprise one or more additional therapeutically active agents, such as another therapeutic agent or drug that can be used to treat inflammatory diseases.

Pharmaceutically acceptable carriers may include, for example, pharmaceutically acceptable liquid, gel, or solid carriers, aqueous media, non-aqueous media, antimicrobial agents, isotonic agents, buffers, antioxidants, anesthetics, suspending/dispersing agents, chelating agents, diluents, adjuvants, excipients, or non-toxic auxiliary substances, as well as various components or combinations thereof known in the art.

In certain embodiments, the pharmaceutical composition is formulated as an injectable composition. Injectable pharmaceutical compositions can be prepared in any conventional form, such as liquid solutions, suspensions, emulsions, or solid forms suitable for producing liquid solutions, suspensions, or emulsions. Injectable formulations may comprise sterile and/or pyrogen-free solutions that are ready for injection; sterile dry soluble products that are prepared for combination with a solvent just prior to use, such as lyophilized powders, including subcutaneous tablets; sterile suspensions that are ready for injection; sterile dry insoluble products that are prepared for combination with a solvent just prior to use; and sterile and/or pyrogen-free emulsions. The solutions can be aqueous or non-aqueous.

In certain embodiments, unit doses of parenteral formulations are packaged in ampoules, vials, or syringes with needles. All formulations for parenteral administration should be sterile and pyrogen-free, as is known and practiced in the art.

In certain embodiments, formulations suitable for parenteral administration (e.g., by injection) comprise active ingredients dissolved, suspended, or otherwise provided (e.g., in liposomes or other microparticles) in aqueous or non-aqueous, isotonic, pyrogen-free, sterile liquids (e.g., solutions, suspensions). These liquids may additionally contain other pharmaceutically acceptable components, such as antioxidants, buffers, preservatives, stabilizers, antimicrobial agents, suspending agents, thickeners, and solutes that render the formulation isotonic with the blood (or other relevant body fluids) of the intended recipient. Examples of excipients include, for example, water, alcohols, polyols, glycerin, and vegetable oils. Examples of isotonic carriers suitable for such formulations include sodium chloride injection, Ringer's solution, or lactated Ringer's injection.

In certain embodiments, sterile lyophilized powders are prepared by dissolving the antigen-binding molecules disclosed herein in a suitable solvent. The solvent may contain excipients that improve the stability of the powder or the reconstituted solution derived from the powder or other pharmacological components. Suitable excipients include, but are not limited to, water, trehalose, sorbitol, fructose, corn syrup, xylitol, glycerin, glucose, sucrose, or other suitable reagents. The solvent may contain buffers, such as citrate, sodium phosphate, or potassium phosphate, or other such buffers known to those skilled in the art. In one embodiment, the buffer is at approximately neutral pH. The solution is then subjected to sterile filtration under standard conditions known to the person skilled in the art, followed by lyophilization to obtain the desired formulation. In one embodiment, the resulting solution is dispensed into vials for lyophilization. Each vial may contain a single dose or multiple doses of the antigen-binding molecules or their compositions described herein. Overfilling the vial a small amount above that required for a single dose or a set of doses (e.g., about 10%) is acceptable to facilitate accurate sample withdrawal and accurate dosing. The lyophilized powder can be stored under appropriate conditions, such as at approximately 4° C. to room temperature.

Reconstituting the lyophilized powder with water for injection provides a formulation for parenteral administration. In one embodiment, sterile and/or pyrogen-free water or another liquid suitable carrier is added to the lyophilized powder for reconstitution. The precise amount depends on the selected therapy given and can be determined empirically.

Uses

The TSLP-binding molecules, the IL-33-binding molecule, the multispecific antigen-binding molecule, the bispecific antigen-binding molecule, the fusion protein, the conjugate, and/or the composition described herein have numerous in vitro and in vivo uses. For example, a therapeutically effective amount of these molecules can be administered in vitro or ex vivo to cultured cells, or administered in vivo to a human subject, to treat, prevent, or alleviate inflammatory diseases in the subject, or to inhibit or block the specific binding of TSLP to the complex of TSLPR and IL-7Rα, and/or IL-33 to the complex of ST2 and IL-1RAcP, or to inhibit the activation of downstream signaling pathways mediated by TSLP and/or IL-33.

In other aspects, the present disclosure also provides the use of the TSLP-binding molecule, the IL-33-binding molecule, the multispecific antigen-binding molecule, the bispecific antigen-binding molecule, the fusion protein, the conjugate, and/or the composition described herein in the preparation of a medicament for the treatment, prevention, and/or alleviation of inflammatory diseases.

In some embodiments, the use also comprises administration in combination with another therapeutic agent or drug for the treatment of inflammatory diseases, such as β2-adrenergic receptor agonists, antibiotics, anticholinergics, antihistamines, proton pump inhibitors, kinase inhibitors, corticosteroids, etc. When administered in combination with another therapeutic agent or drug, the two can be administered in any order or simultaneously; when administered sequentially, they can be administered at appropriate intervals to maximize the therapeutic effect.

Preferred subjects include human patients suffering from inflammatory diseases. The methods are particularly suitable for treating inflammatory diseases in patients who can benefit from blocking the specific binding of TSLP to the complex of TSLPR and IL-7Rα and/or IL-33 to the complex of ST2 and IL-1RAcP, thereby inhibiting the activation of downstream signaling pathways mediated by TSLP and/or IL-33, and achieving the purpose of treating inflammatory diseases. In a particular embodiment, the method is suitable for in vivo treatment of type 2 inflammatory diseases, such as asthma, chronic rhinosinusitis with or without nasal polyps, allergic rhinitis, chronic obstructive pulmonary disease, atopic dermatitis, prurigo nodularis, chronic spontaneous urticaria, and eosinophilic esophagitis.

The TSLP-binding molecules, the IL-33-binding molecule, the multispecific antigen-binding molecule, the bispecific antigen-binding molecule, the fusion protein, the conjugate, and/or the composition can be administered to subjects via any suitable route of administration. Those skilled in the art will understand that the route and/or method of administration may vary depending on the desired outcome. The preferred routes of administration include intravenous, intramuscular, intradermal, intraperitoneal, subcutaneous, spinal, or other parenteral routes, such as injection or infusion. The term "parenteral administration" used herein refers to a mode of administration other than enteral and topical administration, usually refers to a mode of administration by injection, including but not limited to intravenous, intramuscular, intra-arterial, intrathecal, intracapsular, intraorbital, intracardiac, intradermal, intraperitoneal, trans-tracheal, subcutaneous, subepidermal, intra-articular, subcapsular, subarachnoid, intraspinal, epidural, and intrasternal injection and infusion.

Those skilled in the art will understand that the appropriate dosage may vary from patient to patient. Determining the optimal dosage typically involves balancing the level of therapeutic benefit against any risks or adverse side effects. In some embodiments, the antigen-binding molecules provided herein can be administered at a therapeutically effective dose of about 0.01 mg/kg to about 100 mg/kg. In some embodiments, the dosing regimen can be adjusted to provide the optimal desired response (e.g., therapeutic response). For example, a single dose can be administered, or several divided doses can be administered over time. When more than one dose is administered, the doses can be administered at appropriate intervals to maximize the therapeutic effect. In some embodiments, the administered dosage can vary during the course of treatment depending on the subject's response.

Sequence Listing

The application is accompanied by a Sequence Listing containing numerous amino acid sequences. Table A below provides an overview of the included amino acid sequences.

TABLE A

| Overview of Amino Acid Sequences | | |
|---|---|---|
| SEQ ID NO | Sequence | Description |
| 1 | GSNFSLYAMS | HYB0101's CDR1 |
| 2 | RIRDNGRTN | HYB0101's CDR2 |
| 3 | DNRVTTF | HYB0101's CDR3 |
| 4 | QVQLVESGGGLVQPGGSLTLSCVAAGSNFSLYAMSYYRQVPGKQR ELVARIRDNGRTNYADSVKDRFTISRDSAKNTVYLQMHSLKPEDTA VYYCNADNRVTTFWGRGTQVTVSS | HYB0101's VHH sequence |
| 5 | GSIFSIDAMG | HYB0102's CDR1 |
| 6 | AIGSGTY | HYB0102's CDR2 |
| 7 | GDSYPDEY | HYB0102's CDR3 |
| 8 | QLQLVESGGGLVQPGGSLRLSCAASGSIFSIDAMGWYRQAPGKERE LVAAIGSGTYYADSVKGRFTISRDNAKKNTLYLQMDSLKPEDTAIY YCASGDSYPDEYWGQGTQVTVSA | HYB0102's VHH sequence |
| 9 | ESDFSIYIMG | HYB0103's CDR1 |
| 10 | TITPGGNTN | HYB0103's CDR2 |
| 11 | RNIFRNVDY | HYB0103's CDR3 |
| 12 | QLQLVESGGGLVQPGGSLRLSCAASESDFSIYIMGWYRQAPGKQRE LVVTITPGGNTNYVDSVKGRFTISRDNTMNTAYLQMNSLKPDDTAV YYCNARNIFRNVDYSGKGTLVTVSS | HYB0103's VHH sequence |
| 13 | GIEFSIYIMG | HYB0104's CDR1 |
| 14 | TVTPGGNTN | HYB0104's CDR2 |
| 15 | RNIFRNMDY | HYB0104's CDR3 |
| 16 | QVQLVESGGGLVQPGGSLRLSCVASGIEFSIYIMGWYRQAPGKQRE LVATVTPGGNTNYADSVKGRFTISRDNTKNTAYLQMNSLKPDDTA VYYCNARNIFRNMDYQGKGTLVTVSS | HYB0104's VHH sequence |
| 17 | GSDFNIYIMG | HYB0105's CDR1 |
| 18 | TITPGGNTN | HYB0105's CDR2 |
| 19 | RNIFRYMDY | HYB0105's CDR3 |
| 20 | QVQLVESGGGSVQPGGSLRLSCAASGSDFNIYIMGWYQQAPGKQR ELVATITPGGNTNYVDSVKGRFTISRDNTKNTAYLQMNSLKPDDTA VYYCNARNIFRYMDYWGKGTLVTVSS | HYB0105's VHH sequence |
| 21 | GFIFDDYAIA | HYB0106's CDR1 |
| 22 | FISNSDGTAY | HYB0106's CDR2 |
| 23 | EGRMGTHSRDSVYFWAFSALYDY | HYB0106's CDR3 |
| 24 | QVQLVESGGGLVQAGGSLRLSCAASGFIFDDYAIAWFRQAPGKERE GVSFISNSDGTAYYADSVKGRFTISSDNAKNTVYLQMDSLKPDDTA DYYCAAEGRMGTHSRDSVYFWAFSALYDYWGQGTQVTVSS | HYB0106's VHH sequence |
| 25 | GFTFDDYAIT | HYB0107's CDR1 |

TABLE A-continued

Overview of Amino Acid Sequences

| SEQ ID NO | Sequence | Description |
|---|---|---|
| 26 | YISNSDGMTY | HYB0107's CDR2 |
| 27 | EGIMGTHNRDNVYFWAFSALYDY | HYB0107's CDR3 |
| 28 | QLQLVESGGGLVQAGGSLRLSCAASGFTFDDYAITWFRQAPGKERE GVAYISNSDGMTYYVDSVKGRFTISSDNAKNTVYLQMDSLKPEDT AVYYCAAEGIMGTHNRDNVYFWAFSALYDYWGQGTQVTVSS | HYB0107's VHH sequence |
| 29 | GFTFDDYAIT | HYB0108's CDR1 |
| 30 | YISNFDGMTY | HYB0108's CDR2 |
| 31 | EGRMGTHSRDSVYFWAFSALYDH | HYB0108's CDR3 |
| 32 | QVQLVESGGGLVQAGGSLRLSCAASGFTFDDYAITWFRQAPGKERE GVAYISNFDGMTYYADSVKGRFTISSDNAKNTVYLQMDSLKPEDT AVYYCAAEGRMGTHSRDSVYFWAFSALYDHWGQGTQVTVSS | HYB0108's VHH sequence |
| 33 | GFTFDDYAIT | HYB0109's CDR1 |
| 34 | YISNSDGMTY | HYB0109's CDR2 |
| 35 | EGRMGTHSRDSVYFWAFSALYDY | HYB0109's CDR3 |
| 36 | QVQLVESGGGLVQAGGSLRLSCAASGFTFDDYAITWFRQAPGKERE GVAYISNSDGMTYYADSVKGRFTISSDNAKNTVYLQMDSLKPEDT AVYYCAAEGRMGTHSRDSVYFWAFSALYDYWGQGTQVTVSS | HYB0109's VHH sequence |
| 37 | GFTFDDYAIT | HYB0110's CDR1 |
| 38 | YISNNDGMTY | HYB0110's CDR2 |
| 39 | EGRMGTHSRDSVYFWAFSALYDY | HYB0110's CDR3 |
| 40 | QVQLVESGGGLVQAGGSLRLSCAASGFTFDDYAITWFRQAPGKERE GVAYISNNDGMTYYADSVKGRFTISSDNAKNPVYLQMDSLKPEDT AVYYCAAEGRMGTHSRDSVYFWAFSALYDYWGQGTQVTVSS | HYB0110's VHH sequence |
| 41 | GFTFGDYAIT | HYB0111's CDR1 |
| 42 | YISNFDGMTY | HYB0111's CDR2 |
| 43 | EGRMGTHSRDSVYFWAFSALYDY | HYB0111's CDR3 |
| 44 | QVQLVESGGGLVQAGGSLRLSCAASGFTFGDYAITWFRQAPGKERE GVAYISNFDGMTYYADSVKGRFTISSDNAKNTVYLQMDSLKPEDT AVYYCAAEGRMGTHSRDSVYFWAFSALYDYWGQGTQVTVSS | HYB0111's VHH sequence |
| 45 | GFIFDDYAIA | HYB0112's CDR1 |
| 46 | FISNSDGTAY | HYB0112's CDR2 |
| 47 | EGRMGTHSGDSVYFWSFSALYDY | HYB0112's CDR3 |
| 48 | QVQLVESGGGLVQAGGSLRLSCAASGFIFDDYAIAWFRQAPGKERE GVSFISNSDGTAYYADSVKGRFTISSDNAKNTVYLQMDSLKPDDTA DYYCAAEGRMGTHSGDSVYFWSFSALYDYWGQGTQVTVSS | HYB0112's VHH sequence |
| 49 | GFNFDDYAIA | HYB0113's CDR1 |
| 50 | FISNSDGTAY | HYB0113's CDR2 |
| 51 | EGRMGTHSRDSVYFWSFSALYDY | HYB0113's CDR3 |
| 52 | QLQLVESGGGLVQAGGSLRLSCAASGFNFDDYAIAWFRQAPGKER EGVSFISNSDGTAYYADSVKGRFTISSDNAKNTVYLQMDSLKPDDT ADYYCAAEGRMGTHSRDSVYFWSFSALYDYWGQGTQVTVSS | HYB0113's VHH sequence |
| 53 | GFSFDDYAIA | HYB0114's CDR1 |
| 54 | FISNSDGTAY | HYB0114's CDR2 |

TABLE A-continued

Overview of Amino Acid Sequences

| SEQ ID NO | Sequence | Description |
|---|---|---|
| 55 | EGRMGTHSRDSVYFWSFSALYDY | HYB0114's CDR3 |
| 56 | QVQLVESGGGLVQAGGSLRLSCAASGFSFDDYAIAWFRQAPGKERE<br>GVSFISNSDGTAYYADSVKGRFTISSDNAKNTVYLQMDSLKPDDTA<br>DYYCAAEGRMGTHSRDSVYFWSFSALYDYWGQGTQVTVSS | HYB0114's VHH<br>sequence |
| 57 | GGTFERLAMG | HYB0115's CDR1 |
| 58 | FISNSDGTAY | HYB0115's CDR2 |
| 59 | EGRMGTHSRDSVYFWSFSALYDY | HYB0115's CDR3 |
| 60 | QLQLVESGGGLVQPGGSLRLSCVLSGGTFERLAMGWFRQAPGKER<br>EGVSFISNSDGTAYYADSVKGRFTISSDNAKNTVYLQMDSLKPDDT<br>ADYYCAAEGRMGTHSRDSVYFWSFSALYDYWGQGTQVTVSA | HYB0115's VHH<br>sequence |
| 61 | GFTFDDYAIT | HYB0116's CDR1 |
| 62 | YISNNDHNTY | HYB0116's CDR2 |
| 63 | EGRMGTHSRESSYFWTFPALYDY | HYB0116's CDR3 |
| 64 | QVQLVESGGGLVQAGGSLRLSCAASGFTFDDYAITWFRQAPGKERE<br>GVSYISNNDHNTYYADSVKGRFTISSDNAKNTVYLQMDSLKPEDTA<br>VYYCAAEGRMGTHSRESSYFWTFPALYDYWGQGTQVTVSS | HYB0116's VHH<br>sequence |
| 65 | QVQLLESGGGLVQPGGSLRLSCAASGFTFGDYAITWFRQAPGKGLE<br>GVAYISNFDGMTYYADSVKGRFTISSDNSKNTVYLQMNSLRAEDTA<br>VYYCAAEGRMGTHSRDSVYFWAFSALYDYWGQGTLVTVSS | HYB0111-hz1's<br>VHH sequence |
| 66 | EVQLLESGGGLVQPGGSLRLSCAASGFTFGDYAITWFRQAPGKGLE<br>GVAYISNFDGMTYYADSVKGRFTISSDNSKNTVYLQMNSLRAEDTA<br>VYYCAAEGRMGTHSRDSVYFWAFSALYDYWGQGTLVTVSS | HYB0111-hz2's<br>VHH sequence |
| 67 | QVQLLESGGGLVQPGGSLRLSCAASGFTFGDYAITWFRQAPGKGLE<br>GVAYISNFDGMTYYADSVKGRFTISRDNSKNTVYLQMNSLRAEDT<br>AVYYCAAEGRMGTHSRDSVYFWAFSALYDYWGQGTLVTVSS | HYB0111-hz3's<br>VHH sequence |
| 68 | EVQLLESGGGLVQPGGSLRLSCAASGFTFGDYAITWFRQAPGKGLE<br>GVAYISNFDGMTYYADSVKGRFTISRDNSKNTVYLQMNSLRAEDT<br>AVYYCAAEGRMGTHSRDSVYFWAFSALYDYWGQGTLVTVSS | HYB0111-hz4's<br>VHH sequence |
| 69 | EVQLLESGGGLVQAGGSLRLSCAASGFTFGDYAITWFRQAPGKGLE<br>GVAYISNFDGMTYYADSVKGRFTISSDNSKNTVYLQMNSLRAEDTA<br>VYYCAAEGRMGTHSRDSVYFWAFSALYDYWGQGTLVTVSS | HYB0111-hz5's<br>VHH sequence |
| 70 | EVQLLESGGGLVQPGGSLRLSCAASGFTFGDYAITWFRQAPGKELE<br>GVAYISNFDGMTYYADSVKGRFTISSDNSKNTVYLQMNSLRAEDTA<br>VYYCAAEGRMGTHSRDSVYFWAFSALYDYWGQGTLVTVSS | HYB0111-hz6's<br>VHH sequence |
| 71 | EVQLLESGGGLVQPGGSLRLSCAASGFTFGDYAITWFRQAPGKGRE<br>GVAYISNFDGMTYYADSVKGRFTISSDNSKNTVYLQMNSLRAEDTA<br>VYYCAAEGRMGTHSRDSVYFWAFSALYDYWGQGTLVTVSS | HYB0111-hz7's<br>VHH sequence |
| 72 | EVQLLESGGGLVQPGGSLRLSCAASGFTFGDYAITWFRQAPGKERE<br>GVAYISNFDGMTYYADSVKGRFTISSDNSKNTVYLQMNSLRAEDTA<br>VYYCAAEGRMGTHSRDSVYFWAFSALYDYWGQGTLVTVSS | HYB0111-hz8's<br>VHH sequence |
| 73 | EVQLLESGGGLVQPGGSLRLSCAASGFTFGDYAITWFRQAPGKGLE<br>GVAYISNFDGMTYYADSVKGRFTISSDNAKNTVYLQMNSLRAEDT<br>AVYYCAAEGRMGTHSRDSVYFWAFSALYDYWGQGTLVTVSS | HYB0111-hz9's<br>VHH sequence |
| 74 | EVQLLESGGGLVQPGGSLRLSCAASGFTFGDYAITWFRQAPGKGLE<br>GVAYISNFDGMTYYADSVKGRFTISSDNSKNTVYLQMDSLRAEDTA<br>VYYCAAEGRMGTHSRDSVYFWAFSALYDYWGQGTLVTVSS | HYB0111-hz10's<br>VHH sequence |
| 75 | EVQLLESGGGLVQPGGSLRLSCAASGFTFGDYAITWFRQAPGKGLE<br>GVAYISNFDGMTYYADSVKGRFTISSDNSKNTVYLQMNSLRPEDTA<br>VYYCAAEGRMGTHSRDSVYFWAFSALYDYWGQGTLVTVSS | HYB0111-hz11's<br>VHH sequence |
| 76 | EVQLLESGGGLVQPGGSLRLSCAASGFTFGDYAITWFRQAPGKGLE<br>GVSYISNFDGMTYYADSVKGRFTISSDNSKNTVYLQMNSLRAEDTA<br>VYYCAAEGRMGTHSRDSVYFWAFSALYDYWGQGTLVTVSS | HYB0111-hz12's<br>VHH sequence |

TABLE A-continued

Overview of Amino Acid Sequences

| SEQ ID NO | Sequence | Description |
|---|---|---|
| 77 | EVQLVESGGGLVQPGGSLRLSCAASGFTFGDYAITWFRQAPGKGLE GVAYISNFDGMTYYADSVKGRFTISSDNSKNTVYLQMNSLRAEDTA VYYCAAEGRMGTHSRDSVYFWAFSALYDYWGQGTLVTVSS | HYB0111-hz13's VHH sequence |
| 78 | EVQLLESGGGLVQPGGSLRLSCAASGFTFGDYAITWVRQAPGKGLE GVAYISNFDGMTYYADSVKGRFTISSDNSKNTVYLQMNSLRAEDTA VYYCAAEGRMGTHSRDSVYFWAFSALYDYWGQGTLVTVSS | HYB0111-hz14's VHH sequence |
| 79 | GRTFSNYAMG | HYB0501's CDR1 |
| 80 | TISWNGGSTY | HYB0501's CDR2 |
| 81 | RWLPVNQFLGVMRPSFVSA | HYB0501's CDR3 |
| 82 | QLQLVESGGGLVQAGGSLRLSCAASGRTFSNYAMGWFRQAPGKER EFVATISWNGGSTYYEDSVKGRFTISRDNSENTVDLQMNSLKPEDT AVYYCAARWLPVNQFLGVMRPSFVSAWGQGTQVTVSS | HYB0501's VHH sequence |
| 83 | TRTFSHLAMG | HYB0502's CDR1 |
| 84 | TISWGGDRTY | HYB0502's CDR2 |
| 85 | DKLLFGWGSPPNTDFGS | HYB0502's CDR3 |
| 86 | QVQLVESGGGLVQAGGSLRLSCAASTRTFSHLAMGWFRQAVGKER EPVATISWGGDRTYYADSVKARFAISRDNAKSTVYLQMNSLKPEDT AIYYCAADKLLFGWGSPPNTDFGSWGQGTQVTVSS | HYB0502's VHH sequence |
| 87 | GRRIFPLLTMG | HYB0503's CDR1 |
| 88 | VIPRTGDSTY | HYB0503's CDR2 |
| 89 | RDGSSSPRPADFGF | HYB0503's CDR3 |
| 90 | QVQLVESGGGLVQAGDSLRLSCAVSGRRIFPLLTMGWFRQNPGKD REFVAVIPRTGDSTYYADSVKGRFAISRDNAKNTVHLQMNSLKPED TAVYYCAARDGSSSPRPADFGFWGQGTQVTVSS | HYB0503's VHH sequence |
| 91 | GFTFSNHWMY | HYB0504's CDR1 |
| 92 | DISPGGISTR | HYB0504's CDR2 |
| 93 | GRAYVAGVSRASQYVY | HYB0504's CDR3 |
| 94 | QLQLVESGGDLVQPGGSLRLSCLASGFTFSNHWMYWLRQAPGKGL EWVSDISPGGISTRYADSVKGRFTISRDNAKNTVYLEMSSLKPLDTA VYYCAAGRAYVAGVSRASQYVYWGQGTQVTVSS | HYB0504's VHH sequence |
| 95 | GRTFSHYTVG | HYB0505's CDR1 |
| 96 | GLSWNHRTK | HYB0505's CDR2 |
| 97 | DVSPFITTIQTDMEY | HYB0505's CDR3 |
| 98 | QLQLVESGGGLVQPGGSLRLSCAASGRTFSHYTVGWFRQAPGKERE FVAGLSWNHRTKYADSVKGRFTISVDNAKNTVYLQMNSLKPEDTA VYVCTADVSPFITTIQTDMEYWGKGTLVTVSS | HYB0505's VHH sequence |
| 99 | GIIFSKHGMG | HYB0506's CDR1 |
| 100 | RITSGGSTS | HYB0506's CDR2 |
| 101 | ERFIINVEGAGRGPY | HYB0506's CDR3 |
| 102 | QLQLVESGGGLVQSGGSLRLSCTTSGIIFSKHGMGWYRQAPGAQRE LVARITSGGSTSYADSGKGRFTISRDNTKNTLYLQMNSLEPEDTAVY YCNVERFIINVEGAGRGPYWGQGTLVTVSS | HYB0506's VHH sequence |
| 103 | GRTFSTLNMG | HYB0507's CDR1 |
| 104 | NIGWSGGTTY | HYB0507's CDR2 |

TABLE A-continued

Overview of Amino Acid Sequences

| SEQ ID NO | Sequence | Description |
|---|---|---|
| 105 | DIKGLYFPRDARSFDY | HYB0507's CDR3 |
| 106 | QVQLVESGGGLVQAGGSLRLSCAVSGRTFSTLNMGWFRQAPGKER EFVANIGWSGGTTYSSDSAKGRFTISRDNAENTVYLQMNSLKPEDT AVYYCAADIKGLYFPRDARSFDYWGQGTQVTVSS | HYB0507's VHH sequence |
| 107 | GRIFPIYHMG | HYB0508's CDR1 |
| 108 | AIRRSDSMTN | HYB0508's CDR2 |
| 109 | ALGQYYGANTQYDS | HYB0508's CDR3 |
| 110 | QLQLVESGGGLVQAGGSLRLSCAASGRIFPIYHMGWFRQAPGKERE FVAAIRRSDSMTNYADSVKGRFTISRDNAKNTLFLQMNSLRPEDTG VYNCAAALGQYYGANTQYDSWGQGTQVTVSS | HYB0508's VHH sequence |
| 111 | GSIFRFNLMG | HYB0509's CDR1 |
| 112 | VMSEGGTTN | HYB0509's CDR2 |
| 113 | WGSNSGPVLQY | HYB0509's CDR3 |
| 114 | QLQLVESGGGLVQPGGSLRLSCAASGSIFRFNLMGWYRQAPGKQRE LVAVMSEGGTTNYGDSVKGRFTMSRDNAKNTVYLQMNSLKSEDT AVYYCNFWGSNSGPVLQYWGQGTQVTVSS | HYB0509's VHH sequence |
| 115 | GRIFVISNAG | HYB0510's CDR1 |
| 116 | SISRHGEITN | HYB0510's CDR2 |
| 117 | TLGHSPRTDPGDFDS | HYB0510's CDR3 |
| 118 | QVQLVESGGGSVQPGGSLRLACAASGRIFVISNAGWFRQTPGKERE FVASISRHGEITNYADAVKGRFTISRDNSKNMMYLQMNSLNFEDTA VYYCATTLGHSPRTDPGDFDSWGQGTQVTVSS | HYB0510's VHH sequence |
| 119 | GSIFRINTMG | HYB0511's CDR1 |
| 120 | SFTSGGSPN | HYB0511's CDR2 |
| 121 | YIMAWSHGVLKGYDS | HYB0511's CDR3 |
| 122 | QVQLVESGGGLVQPGGSLRLSCAASGSIFRINTMGWYRQAPGKQRE LVASFTSGGSPNYADSVKGRFTISRDNAKNTVYLQMNSLRPEETAV YYCNAYIMAWSHGVLKGYDSWGQGTQVTVSS | HYB0511's VHH sequence |
| 123 | GSIRTVNYMG | HYB0512's CDR1 |
| 124 | VVTSGGGTN | HYB0512's CDR2 |
| 125 | AASTYSSTVVRSF | HYB0512's CDR3 |
| 126 | QVQLVESGGGLVQPGESLRLSCAASGSIRTVNYMGWHRQAPGKQR ELVAVVTSGGGTNYADSVKGRFTISRDDTKNTVYLAMNSLKPEDT AVYYCNAAASTYSSTVVRSFWGQGTQVTVSS | HYB0512's VHH sequence |
| 127 | GSIFRINSMG | HYB0513's CDR1 |
| 128 | TFTTSGGVTN | HYB0513's CDR2 |
| 129 | YVMAWSRGVLKGYDS | HYB0513's CDR3 |
| 130 | QVQLVESGGGLVQPGGSLRLSCAASGSIFRINSMGWYRQAPGKQRE LVATFTTSGGVTNYADSVKGRFTISRDNAKNTVYLQMNNLTPEETA VYYCNAYVMAWSRGVLKGYDSWGQGTQVTVSS | HYB0513's VHH sequence |
| 131 | GRTFSGYRMG | HYB0514's CDR1 |
| 132 | SIRWIGPATA | HYB0514's CDR2 |
| 133 | DPTPSIDYKRGYDY | HYB0514's CDR3 |
| 134 | QVQLVESGGGLVQAGGSLRLSCAASGRTFSGYRMGWFRQAPGKER EFVASIRWIGPATAYADSVKGRFTISRDNAKNTVYLQMNSLKSEDT AVYYCAADPTPSIDYKRGYDYWGQGTQVTVSS | HYB0514's VHH sequence |

TABLE A-continued

Overview of Amino Acid Sequences

| SEQ ID NO | Sequence | Description |
|---|---|---|
| 135 | GRTFNTFRTG | HYB0515's CDR1 |
| 136 | SLNWSSTWTS | HYB0515's CDR2 |
| 137 | GIAGTPVMRATSYIY | HYB0515's CDR3 |
| 138 | QVQLVESGGGLVQPGGSLRVSCAASGRTFNTFRTGWFRQAPGKER EFVASLNWSSTWTSYADSVKGRFSISRDSAKNTVYLQMNSLKPEDT ADYYCAVGIAGTPVMRATSYIYWGQGTQVTVSS | HYB0515's VHH sequence |
| 139 | RFIFPIYAMG | HYB0516's CDR1 |
| 140 | GIERTTDTTL | HYB0516's CDR2 |
| 141 | RNSRRIGDVNDVDY | HYB0516's CDR3 |
| 142 | QVQLVESGGGLVQPGGSLRLSCAASRFIFPIYAMGWFRQAPGKERE FVAGIERTTDTTLYADSVKGRFTISRDNAKNTVYLQMYSLKPEDAA VYYCAARNSRRIGDVNDVDYWGQGTQVTVSS | HYB0516's VHH sequence |
| 143 | RTIFPLYAMG | HYB0517's CDR1 |
| 144 | GISRTTSTTL | HYB0517's CDR2 |
| 145 | RNSRTIGDVNDVDY | HYB0517's CDR3 |
| 146 | QLQLVESGGGLVQAGGSLRLSCAASRTIFPLYAMGWFRQAPGKERE FVAGISRTTSTTLYADSVKGRFTISRDNAANTVYLQMNTLKPEDAA VYYCAARNSRTIGDVNDVDYWGQGTQLTVSS | HYB0517's VHH sequence |
| 147 | GRTISIYMMG | HYB0518's CDR1 |
| 148 | AIMPSGSRTY | HYB0518's CDR2 |
| 149 | KLFRGSGDYINDYDH | HYB0518's CDR3 |
| 150 | QVQLVESGGGLVQAGGSLRLSCAASGRTISIYMMGWFRQAPGKGR EFVSAIMPSGSRTYSADWVKGRFTISRDNSKSTVYLQMNSLKPEDT AVYYCAAKLFRGSGDYINDYDHWGQGTQVTVSS | HYB0518's VHH sequence |
| 151 | QVQLVESGGGLVQPGGSLRLSCAASGSIRTVNYMGWHRQAPGKQR ELVAVVTSGGGTNYADSVKGRFTISRDDTKNTVYLQMNSLRAEDT AVYYCNAAASTYSSTVVRSFWGQGTLVTVSS | HYB0512-hz1's VHH sequence |
| 152 | QVQLVESGGGLVQPGGSLRLSCAASGSIRTVNYMGWHRQAPGKQR ELVAVVTSGGGTNYADSVKGRFTISRDNTKNTVYLQMNSLRAEDT AVYYCNAAASTYSSTVVRSFWGQGTLVTVSS | HYB0512-hz2's VHH sequence |
| 153 | QVQLVESGGGLVQPGGSLRLSCAASGSIRTVNYMGWHRQAPGKQR ELVAVVTSGGGTNYADSVKGRFTISRDDSKNTVYLQMNSLRAEDT AVYYCNAAASTYSSTVVRSFWGQGTLVTVSS | HYB0512-hz3's VHH sequence |
| 154 | QVQLVESGGGLVQPGGSLRLSCAASGSIRTVNYMGWHRQAPGKQR ELVAVVTSGGGTNYADSVKGRFTISRDNSKNTVYLQMNSLRAEDT AVYYCNAAASTYSSTVVRSFWGQGTLVTVSS | HYB0512-hz4's VHH sequence |
| 155 | QVQLVESGGGLVQPGGSLRLSCAASGSIRTVNYMGWHRQAPGKGR ELVAVVTSGGGTNYADSVKGRFTISRDDTKNTVYLQMNSLRAEDT AVYYCNAAASTYSSTVVRSFWGQGTLVTVSS | HYB0512-hz5's VHH sequence |
| 156 | QVQLVESGGGLVQPGGSLRLSCAASGSIRTVNYMGWHRQAPGKQL ELVAVVTSGGGTNYADSVKGRFTISRDDTKNTVYLQMNSLRAEDT AVYYCNAAASTYSSTVVRSFWGQGTLVTVSS | HYB0512-hz6's VHH sequence |
| 157 | EVQLVESGGGLVQPGGSLRLSCAASGSIRTVNYMGWHRQAPGKQR ELVAVVTSGGGTNYADSVKGRFTISRDDTKNTVYLQMNSLRAEDT AVYYCNAAASTYSSTVVRSFWGQGTLVTVSS | HYB0512-hz7's VHH sequence |
| 158 | QVQLVESGGGLVQPGGSLRLSCAASGSIRTVNYMGWHRQAPGKQR ELVSVVTSGGGTNYADSVKGRFTISRDDTKNTVYLQMNSLRAEDT AVYYCNAAASTYSSTVVRSFWGQGTLVTVSS | HYB0512-hz8's VHH sequence |
| 159 | EPKSCDKTHTCPPCPAPELLGGPSVFLFPPKPKDTLMISRTPEVTCVV VDVSHEDPEVKFNWYVDGVEVHNAKTKPREEQYNSTYRVVSVLT | Human IgG1 Fc domain sequence |

TABLE A-continued

Overview of Amino Acid Sequences

| SEQ ID NO | Sequence | Description |
|---|---|---|
| | VLHQDWLNGKEYKCKVSNKALPAPIEKTISKAKGQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP GK | |
| 160 | EPKSADKTHTCPPCPAPEAAGGPSVFLFPPKPKDTLMISRTPEVTCV VVDVSHEDPEVKFNWYVDGVEVHNAKTKPREEQYNSTYRVVSVL TVLHQDWLNGKEYKCKVSNKALPAPIEKTISKAKGQPREPQVYTLP PSREEMTKNQVSLTCLVKGFYPSDIAVEWESNGQPENNYKTTPPVL DSDGSFFLYSKLTVDKSRWQQGNVFSCSVMHEALHNHYTQKSLSL SPGK | Human IgG1 Fc domain sequence comprising $C_{220}A/$ $L_{234}A/L_{235}A$ mutations |
| 161 | QVQLVESGGGLVQPGGSLTLSCVAAGSNFSLYAMSYYRQVPGKQR ELVARIRDNGRTNYADSVKDRFTISRDSAKNTVYLQMHSLKPEDTA VYYCNADNRVTTFWGRGTQVTVSSEPKSADKTHTCPPCPAPEAAG GPSVFLFPPKPKDTLMISRTPEVTCVVVDVSHEDPEVKFNWYVDGV EVHNAKTKPREEQYNSTYRVVSVLTVLHQDWLNGKEYKCKVSNK ALPAPIEKTISKAKGQPREPQVYTLPPSREEMTKNQVSLTCLVKGFY PSDIAVEWESNGQPENNYKTTPPVLDSDGSFFLYSKLTVDKSRWQQ GNVFSCSVMHEALHNHYTQKSLSLSPGK | HYB0101's full length sequence |
| 162 | QLQLVESGGGLVQPGGSLRLSCAASGSIFSIDAMGWYRQAPGKERE LVAAIGSGTYYADSVKGRFTISRDNAKKNTLYLQMDSLKPEDTAIY YCASGDSYPDEYWGQGTQVTVSSEPKSADKTHTCPPCPAPEAAGG PSVFLFPPKPKDTLMISRTPEVTCVVVDVSHEDPEVKFNWYVDGVE VHNAKTKPREEQYNSTYRVVSVLTVLHQDWLNGKEYKCKVSNKA LPAPIEKTISKAKGQPREPQVYTLPPSREEMTKNQVSLTCLVKGFYPS DIAVEWESNGQPENNYKTTPPVLDSDGSFFLYSKLTVDKSRWQQGN VFSCSVMHEALHNHYTQKSLSLSPGK | HYB0102's full length sequence |
| 163 | QLQLVESGGGLVQPGGSLRLSCAASESDFSIYIMGWYRQAPGKQRE LVVTITPGGNTNYVDSVKGRFTISRDNTMNTAYLQMNSLKPDDTAV YYCNARNIFRNVDYSGKGTLVTVSSEPKSADKTHTCPPCPAPEAAG GPSVFLFPPKPKDTLMISRTPEVTCVVVDVSHEDPEVKFNWYVDGV EVHNAKTKPREEQYNSTYRVVSVLTVLHQDWLNGKEYKCKVSNK ALPAPIEKTISKAKGQPREPQVYTLPPSREEMTKNQVSLTCLVKGFY PSDIAVEWESNGQPENNYKTTPPVLDSDGSFFLYSKLTVDKSRWQQ GNVFSCSVMHEALHNHYTQKSLSLSPGK | HYB0103's full length sequence |
| 164 | QVQLVESGGGLVQPGGSLRLSCVASGIEFSIYIMGWYRQAPGKQRE LVATVTPGGNTNYADSVKGRFTISRDNTKNTAYLQMNSLKPDDTA VYYCNARNIFRNMDYQGKGTLVTVSSEPKSADKTHTCPPCPAPEAA GGPSVFLFPPKPKDTLMISRTPEVTCVVVDVSHEDPEVKFNWYVDG VEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPGK | HYB0104's full length sequence |
| 165 | QVQLVESGGGVQPGGSLRLSCAASGSDFNIYIMGWYQQAPGKQR ELVATITPGGNTNYVDSVKGRFTISRDNTKNTAYLQMNSLKPDDTA VYYCNARNIFRYMDYWGKGTLVTVSSEPKSADKTHTCPPCPAPEA AGGPSVFLFPPKPKDTLMISRTPEVTCVVVDVSHEDPEVKFNWYVD GVEVHNAKTKPREEQYNSTYRVVSVLTVLHQDWLNGKEYKCKVS NKALPAPIEKTISKAKGQPREPQVYTLPPSREEMTKNQVSLTCLVKG FYPSDIAVEWESNGQPENNYKTTPPVLDSDGSFFLYSKLTVDKSRW QQGNVFSCSVMHEALHNHYTQKSLSLSPGK | HYB0105's full length sequence |
| 166 | QVQLVESGGGLVQAGGSLRLSCAASGFIFDDYAIAWFRQAPGKERE GVSFISNSDGTAYYADSVKGRFTISSDNAKNTVYLQMDSLKPDDTA DYYCAAEGRMGTHSRDSVYFWAFSALYDYWGQGTQVTVSSEPKS ADKTHTCPPCPAPEAAGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDGS FFLYSKLTVDKSRWQQGNVFSCSVMHEALHNHYTQKSLSLSPGK | HYB0106's full length sequence |
| 167 | QLQLVESGGGLVQAGGSLRLSCAASGFTFDDYAITWFRQAPGKERE GVAYISNSDGMTYYVDSVKGRFTISSDNAKNTVYLQMDSLKPEDT AVYYCAAEGIMGTHNRDNVYFWAFSALYDYWGQGTQVTVSSEPK SADKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | HYB0107's full length sequence |

TABLE A-continued

Overview of Amino Acid Sequences

| SEQ ID NO | Sequence | Description |
|---|---|---|
| 168 | QVQLVESGGGLVQAGGSLRLSCAASGFTFDDYAITWFRQAPGKERE GVAYISNFDGMTYYADSVKGRFTISSDNAKNTVYLQMDSLKPEDT AVYYCAAEGRMGTHSRDSVYFWAFSALYDHWGQGTQVTVSSEPK SADKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | HYB0108's full length sequence |
| 169 | QVQLVESGGGLVQAGGSLRLSCAASGFTFDDYAITWFRQAPGKERE GVAYISNSDGMTYYADSVKGRFTISSDNAKNTVYLQMDSLKPEDT AVYYCAAEGRMGTHSRDSVYFWAFSALYDYWGQGTQVTVSSEPK SADKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | HYB0109's full length sequence |
| 170 | QVQLVESGGGLVQAGGSLRLSCAASGFTFDDYAITWFRQAPGKERE GVAYISNNDGMTYYADSVKGRFTISSDNAKNPVYLQMDSLKPEDT AVYYCAAEGRMGTHSRDSVYFWAFSALYDYWGQGTQVTVSSEPK SADKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | HYB0110's full length sequence |
| 171 | QVQLVESGGGLVQAGGSLRLSCAASGFTFGDYAITWFRQAPGKERE GVAYISNFDGMTYYADSVKGRFTISSDNAKNTVYLQMDSLKPEDT AVYYCAAEGRMGTHSRDSVYFWAFSALYDYWGQGTQVTVSSEPK SADKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | HYB0111's full length sequence |
| 172 | QVQLVESGGGLVQAGGSLRLSCAASGFIFDDYAIAWFRQAPGKERE GVSFISNSDGTAYYADSVKGRFTISSDNAKNTVYLQMDSLKPDDTA DYYCAAEGRMGTHSGDSVYFWSFSALYDYWGQGTQVTVSSEPKS ADKTHTCPPCPAPEAAGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDGS FFLYSKLTVDKSRWQQGNVFSCSVMHEALHNHYTQKSLSLSPGK | HYB0112's full length sequence |
| 173 | QLQLVESGGGLVQAGGSLRLSCAASGFNFDDYAIAWFRQAPGKER EGVSFISNSDGTAYYADSVKGRFTISSDNAKNTVYLQMDSLKPDDT ADYYCAAEGRMGTHSRDSVYFWSFSALYDYWGQGTQVTVSSEPK SADKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | HYB0113's full length sequence |
| 174 | QVQLVESGGGLVQAGGSLRLSCAASGFSFDDYAIAWFRQAPGKERE GVSFISNSDGTAYYADSVKGRFTISSDNAKNTVYLQMDSLKPDDTA DYYCAAEGRMGTHSRDSVYFWSFSALYDYWGQGTQVTVSSEPKS ADKTHTCPPCPAPEAAGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDGS FFLYSKLTVDKSRWQQGNVFSCSVMHEALHNHYTQKSLSLSPGK | HYB0114's full length sequence |
| 175 | QLQLVESGGGLVQPGGSLRLSCVLSGGTFERLAMGWFRQAPGKER EGVSFISNSDGTAYYADSVKGRFTISSDNAKNTVYLQMDSLKPDDT ADYYCAAEGRMGTHSRDSVYFWSFSALYDYWGQGTQVTVSAEPK SADKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | HYB0115's full length sequence |
| 176 | QVQLVESGGGLVQAGGSLRLSCAASGFTFDDYAITWFRQAPGKERE GVSYISNNDHNTYYADSVKGRFTISSDNAKNTVYLQMDSLKPEDTA VYYCAAEGRMGTHSRESSYFWTFPALYDYWGQGTQVTVSSEPKSA | HYB0116's full length sequence |

TABLE A-continued

Overview of Amino Acid Sequences

| SEQ ID NO | Sequence | Description |
|---|---|---|
| | DKTHTCPPCPAPEAAGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPAPIEKTISKAKGQPREPQVYTLPPSREE<br>MTKNQVSLTCLVKGFYPSDIAVEWESNGQPENNYKTTPPVLDSDGS<br>FFLYSKLTVDKSRWQQGNVFSCSVMHEALHNHYTQKSLSLSPGK | |
| 177 | QVQLLESGGGLVQPGGSLRLSCAASGFTFGDYAITWFRQAPGKGLE<br>GVAYISNFDGMTYYADSVKGRFTISSDNSKNTVYLQMNSLRAEDTA<br>VYYCAAEGRMGTHSRDSVYFWAFSALYDYWGQGTLVTVSSEPKS<br>ADKTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSREE<br>MTKNQVSLTCLVKGFYPSDIAVEWESNGQPENNYKTTPPVLDSDGS<br>FFLYSKLTVDKSRWQQGNVFSCSVMHEALHNHYTQKSLSLSPGK | HYB0111-hz1's full<br>length sequence |
| 178 | EVQLLESGGGLVQPGGSLRLSCAASGFTFGDYAITWFRQAPGKGLE<br>GVAYISNFDGMTYYADSVKGRFTISSDNSKNTVYLQMNSLRAEDTA<br>VYYCAAEGRMGTHSRDSVYFWAFSALYDYWGQGTLVTVSSEPKS<br>ADKTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSREE<br>MTKNQVSLTCLVKGFYPSDIAVEWESNGQPENNYKTTPPVLDSDGS<br>FFLYSKLTVDKSRWQQGNVFSCSVMHEALHNHYTQKSLSLSPGK | HYB0111-hz2's full<br>length sequence |
| 179 | QVQLLESGGGLVQPGGSLRLSCAASGFTFGDYAITWFRQAPGKGLE<br>GVAYISNFDGMTYYADSVKGRFTISRDNSKNTVYLQMNSLRAEDT<br>AVYYCAAEGRMGTHSRDSVYFWAFSALYDYWGQGTLVTVSSEPK<br>SADKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRE<br>EMTKNQVSLTCLVKGFYPSDIAVEWESNGQPENNYKTTPPVLDSDG<br>SFFLYSKLTVDKSRWQQGNVFSCSVMHEALHNHYTQKSLSLSPGK | HYB0111-hz3's full<br>length sequence |
| 180 | EVQLLESGGGLVQPGGSLRLSCAASGFTFGDYAITWFRQAPGKGLE<br>GVAYISNFDGMTYYADSVKGRFTISRDNSKNTVYLQMNSLRAEDT<br>AVYYCAAEGRMGTHSRDSVYFWAFSALYDYWGQGTLVTVSSEPK<br>SADKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRE<br>EMTKNQVSLTCLVKGFYPSDIAVEWESNGQPENNYKTTPPVLDSDG<br>SFFLYSKLTVDKSRWQQGNVFSCSVMHEALHNHYTQKSLSLSPGK | HYB0111-hz4's full<br>length sequence |
| 181 | EVQLLESGGGLVQAGGSLRLSCAASGFTFGDYAITWFRQAPGKGLE<br>GVAYISNFDGMTYYADSVKGRFTISSDNSKNTVYLQMNSLRAEDTA<br>VYYCAAEGRMGTHSRDSVYFWAFSALYDYWGQGTLVTVSSEPKS<br>ADKTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSREE<br>MTKNQVSLTCLVKGFYPSDIAVEWESNGQPENNYKTTPPVLDSDGS<br>FFLYSKLTVDKSRWQQGNVFSCSVMHEALHNHYTQKSLSLSPGK | HYB0111-hz5's full<br>length sequence |
| 182 | EVQLLESGGGLVQPGGSLRLSCAASGFTFGDYAITWFRQAPGKELE<br>GVAYISNFDGMTYYADSVKGRFTISSDNSKNTVYLQMNSLRAEDTA<br>VYYCAAEGRMGTHSRDSVYFWAFSALYDYWGQGTLVTVSSEPKS<br>ADKTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSREE<br>MTKNQVSLTCLVKGFYPSDIAVEWESNGQPENNYKTTPPVLDSDGS<br>FFLYSKLTVDKSRWQQGNVFSCSVMHEALHNHYTQKSLSLSPGK | HYB0111-hz6's full<br>length sequence |
| 183 | EVQLLESGGGLVQPGGSLRLSCAASGFTFGDYAITWFRQAPGKRE<br>GVAYISNFDGMTYYADSVKGRFTISSDNSKNTVYLQMNSLRAEDTA<br>VYYCAAEGRMGTHSRDSVYFWAFSALYDYWGQGTLVTVSSEPKS<br>ADKTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSREE<br>MTKNQVSLTCLVKGFYPSDIAVEWESNGQPENNYKTTPPVLDSDGS<br>FFLYSKLTVDKSRWQQGNVFSCSVMHEALHNHYTQKSLSLSPGK | HYB0111-hz7's full<br>length sequence |
| 184 | EVQLLESGGGLVQPGGSLRLSCAASGFTFGDYAITWFRQAPGKERE<br>GVAYISNFDGMTYYADSVKGRFTISSDNSKNTVYLQMNSLRAEDTA<br>VYYCAAEGRMGTHSRDSVYFWAFSALYDYWGQGTLVTVSSEPKS<br>ADKTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSREE | HYB0111-hz8's full<br>length sequence |

TABLE A-continued

Overview of Amino Acid Sequences

| SEQ ID NO | Sequence | Description |
|---|---|---|
| | MTKNQVSLTCLVKGFYPSDIAVEWESNGQPENNYKTTPPVLDSDGS FFLYSKLTVDKSRWQQGNVFSCSVMHEALHNHYTQKSLSLSPGK | |
| 185 | EVQLLESGGGLVQPGGSLRLSCAASGFTFGDYAITWFRQAPGKGLE GVAYISNFDGMTYYADSVKGRFTISSDNAKNTVYLQMNSLRAEDT AVYYCAAEGRMGTHSRDSVYFWAFSALYDYWGQGTLVTVSSEPK SADKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | HYB0111-hz9's full length sequence |
| 186 | EVQLLESGGGLVQPGGSLRLSCAASGFTFGDYAITWFRQAPGKGLE GVAYISNFDGMTYYADSVKGRFTISSDNSKNTVYLQMDSLRAEDTA VYYCAAEGRMGTHSRDSVYFWAFSALYDYWGQGTLVTVSSEPKS ADKTHTCPPCPAPEAAGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDGS FFLYSKLTVDKSRWQQGNVFSCSVMHEALHNHYTQKSLSLSPGK | HYB0111-hz10's full length sequence |
| 187 | EVQLLESGGGLVQPGGSLRLSCAASGFTFGDYAITWFRQAPGKGLE GVAYISNFDGMTYYADSVKGRFTISSDNSKNTVYLQMNSLRPEDTA VYYCAAEGRMGTHSRDSVYFWAFSALYDYWGQGTLVTVSSEPKS ADKTHTCPPCPAPEAAGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDGS FFLYSKLTVDKSRWQQGNVFSCSVMHEALHNHYTQKSLSLSPGK | HYB0111-hz11's full length sequence |
| 188 | EVQLLESGGGLVQPGGSLRLSCAASGFTFGDYAITWFRQAPGKGLE GVSYISNFDGMTYYADSVKGRFTISSDNSKNTVYLQMNSLRAEDTA VYYCAAEGRMGTHSRDSVYFWAFSALYDYWGQGTLVTVSSEPKS ADKTHTCPPCPAPEAAGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDGS FFLYSKLTVDKSRWQQGNVFSCSVMHEALHNHYTQKSLSLSPGK | HYB0111-hz12's full length sequence |
| 189 | EVQLVESGGGLVQPGGSLRLSCAASGFTFGDYAITWFRQAPGKGLE GVAYISNFDGMTYYADSVKGRFTISSDNSKNTVYLQMNSLRAEDTA VYYCAAEGRMGTHSRDSVYFWAFSALYDYWGQGTLVTVSSEPKS ADKTHTCPPCPAPEAAGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDGS FFLYSKLTVDKSRWQQGNVFSCSVMHEALHNHYTQKSLSLSPGK | HYB0111-hz13's full length sequence |
| 190 | EVQLLESGGGLVQPGGSLRLSCAASGFTFGDYAITWVRQAPGKGLE GVAYISNFDGMTYYADSVKGRFTISSDNSKNTVYLQMNSLRAEDTA VYYCAAEGRMGTHSRDSVYFWAFSALYDYWGQGTLVTVSSEPKS ADKTHTCPPCPAPEAAGGPSVFLFPPKPKDTLMISRTPEVTCVVVDV SHEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDGS FFLYSKLTVDKSRWQQGNVFSCSVMHEALHNHYTQKSLSLSPGK | HYB0111-hz14's full length sequence |
| 191 | QLQLVESGGGLVQAGGSLRLSCAASGRTFSNYAMGWFRQAPGKER EFVATISWNGGSTYYEDSVKGRFTISRDNSENTVDLQMNSLKPEDT AVYYCAARWLPVNQFLGVMRPSFVSAWGQGTQVTVSSEPKSADK THTCPPCPAPEAAGGPSVFLFPPKPKDTLMISRTPEVTCVVVDVSHE DPEVKFNWYVDGVEVHNAKTKPREEQYNSTYRVVSVLTVLHQDW LNGKEYKCKVSNKALPAPIEKTISKAKGQPREPQVYTLPPSREEMTK NQVSLTCLVKGFYPSDIAVEWESNGQPENNYKTTPPVLDSDGSFFL YSKLTVDKSRWQQGNVFSCSVMHEALHNHYTQKSLSLSPGK | HYB0501's full length sequence |
| 192 | QVQLVESGGGLVQAGGSLRLSCAASTRTFSHLAMGWFRQAVGKER EPVATISWGGDRTYYADSVKARFAISRDNAKSTVYLQMNSLKPEDT AIYYCAADKLLFGWGSPPNTDFGSWGQGTQVTVSSEPKSADKTHT CPPCPAPEAAGGPSVFLFPPKPKDTLMISRTPEVTCVVVDVSHEDPE VKFNWYVDGVEVHNAKTKPREEQYNSTYRVVSVLTVLHQDWLNG KEYKCKVSNKALPAPIEKTISKAKGQPREPQVYTLPPSREEMTKNQV SLTCLVKGFYPSDIAVEWESNGQPENNYKTTPPVLDSDGSFFLYSKL TVDKSRWQQGNVFSCSVMHEALHNHYTQKSLSLSPGK | HYB0502's full length sequence |

TABLE A-continued

Overview of Amino Acid Sequences

| SEQ ID NO | Sequence | Description |
|---|---|---|
| 193 | QVQLVESGGGLVQAGDSLRLSCAVSGRRIFPLLTMGWFRQNPGKD REFVAVIPRTGDSTYYADSVKGRFAISRDNAKNTVHLQMNSLKPED TAVYYCAARDGSSSPRPADFGFWGQGTQVTVSSEPKSADKTHTCPP CPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPGK | HYB0503's full length sequence |
| 194 | QLQLVESGGDLVQPGGSLRLSCLASGFTFSNHWMYWLRQAPGKGL EWVSDISPGGISTRYADSVKGRFTISRDNAKNTVYLEMSSLKPLDTA VYYCAAGRAYVAGVSRASQYVYWGQGTQVTVSSEPKSADKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSREEMTKNQVS LTCLVKGFYPSDIAVEWESNGQPENNYKTTPPVLDSDGSFFLYSKLT VDKSRWQQGNVFSCSVMHEALHNHYTQKSLSLSPGK | HYB0504's full length sequence |
| 195 | QLQLVESGGGLVQPGGSLRLSCAASGRTFSHYTVGWFRQAPGKERE FVAGLSWNHRTKYADSVKGRFTISVDNAKNTVYLQMNSLKPEDTA VYVCTADVSPFITTIQTDMEYWGKGTLVTVSSEPKSADKTHTCPPCP APEAAGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPGK | HYB0505's full length sequence |
| 196 | QLQLVESGGGLVQSGGSLRLSCTTSGIIFSKHGMGWYRQAPGAQRE LVARITSGGSTSYADSGKGRFTISRDNTKNTLYLQMNSLEPEDTAVY YCNVERFIINVEGAGRGPYWGQGTLVTVSSEPKSADKTHTCPPCPAP EAAGGPSVFLFPPKPKDTLMISRTPEVTCVVVDVSHEDPEVKFNWY VDGVEVHNAKTKPREEQYNSTYRVVSVLTVLHQDWLNGKEYKCK VSNKALPAPIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPGK | HYB0506's full length sequence |
| 197 | QVQLVESGGGLVQAGGSLRLSCAVSGRTFSTLNMGWFRQAPGKER EFVANIGWSGGTTYSSDSAKGRFTISRDNAENTVYLQMNSLKPEDT AVYYCAADIKGLYFPRDARSFDYWGQGTQVTVSSEPKSADKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSREEMTKNQVS LTCLVKGFYPSDIAVEWESNGQPENNYKTTPPVLDSDGSFFLYSKLT VDKSRWQQGNVFSCSVMHEALHNHYTQKSLSLSPGK | HYB0507's full length sequence |
| 198 | QLQLVESGGGLVQAGGSLRLSCAASGRIFPIYHMGWFRQAPGKERE FVAAIRRSDSMTNYADSVKGRFTISRDNAKNTLFLQMNSLRPEDTG VYNCAAALGQYYGANTQYDSWGQGTQVTVSSEPKSADKTHTCPP CPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPGK | HYB0508's full length sequence |
| 199 | QLQLVESGGGLVQPGGSLRLSCAASGSIFRFNLMGWYRQAPGKQRE LVAVMSEGGTTNYGDSVKGRFTMSRDNAKNTVYLQMNSLKSEDT AVYYCNFWGSNSGPVLQYWGQGTQVTVSSEPKSADKTHTCPPCPA PEAAGGPSVFLFPPKPKDTLMISRTPEVTCVVVDVSHEDPEVKFNW YVDGVEVHNAKTKPREEQYNSTYRVVSVLTVLHQDWLNGKEYKC KVSNKALPAPIEKTISKAKGQPREPQVYTLPPSREEMTKNQVSLTCL VKGFYPSDIAVEWESNGQPENNYKTTPPVLDSDGSFFLYSKLTVDK SRWQQGNVFSCSVMHEALHNHYTQKSLSLSPGK | HYB0509's full length sequence |
| 200 | QVQLVESGGGSVQPGGSLRLACAASGRIFVISNAGWFRQTPGKERE FVASISRHGEITNYADAVKGRFTISRDNSKNMMYLQMNSLNFEDTA VYYCATTLGHSPRTDPGDFDSWGQGTQVTVSSEPKSADKTHTCPPC PAPEAAGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPGK | HYB0510's full length sequence |
| 201 | QVQLVESGGGLVQPGGSLRLSCAASGSIFRINTMGWYRQAPGKQRE LVASFTSGGSPNYADSVKGRFTISRDNAKNTVYLQMNSLRPEETAV YYCNAYIMAWSHGVLKGYDSWGQGTQVTVSSEPKSADKTHTCPPC | HYB0511's full length sequence |

TABLE A-continued

Overview of Amino Acid Sequences

| SEQ ID NO | Sequence | Description |
|---|---|---|
| | PAPEAAGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPGK | |
| 202 | QVQLVESGGGLVQPGESLRLSCAASGSIRTVNYMGWHRQAPGKQR ELVAVVTSGGGTNYADSVKGRFTISRDDTKNTVYLAMNSLKPEDT AVYYCNAAASTYSSTVVRSFWGQGTQVTVSSEPKSADKTHTCPPCP APEAAGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPGK | HYB0512's full length sequence |
| 203 | QVQLVESGGGLVQPGGSLRLSCAASGSIFRINSMGWYRQAPGKQRE LVATFTTSGGVTNYADSVKGRFTISRDNAKNTVYLQMNNLTPEETA VYYCNAYVMAWSRGVLKGYDSWGQGTQVTVSSEPKSADKTHTCP PCPAPEAAGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSREEMTKNQVSL TCLVKGFYPSDIAVEWESNGQPENNYKTTPPVLDSDGSFFLYSKLTV DKSRWQQGNVFSCSVMHEALHNHYTQKSLSLSPGK | HYB0513's full length sequence |
| 204 | QVQLVESGGGLVQAGGSLRLSCAASGRTFSGYRMGWFRQAPGKER EFVASIRWIGPATAYADSVKGRFTISRDNAKNTVYLQMNSLKSEDT AVYYCAADPTPSIDYKRGYDYWGQGTQVTVSSEPKSADKTHTCPP CPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPGK | HYB0514's full length sequence |
| 205 | QVQLVESGGGLVQPGGSLRVSCAASGRTFNTFRTGWFRQAPGKER EFVASLNWSSTWTSYADSVKGRFSISRDSAKNTVYLQMNSLKPEDT ADYYCAVGIAGTPVMRATSYIYWGQGTQVTVSSEPKSADKTHTCPP CPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPGK | HYB0515's full length sequence |
| 206 | QVQLVESGGGLVQPGGSLRLSCAASRFIFPIYAMGWFRQAPGKERE FVAGIERTTDTTLYADSVKGRFTISRDNAKNTVYLQMYSLKPEDAA VYYCAARNSRRIGDVNDVDYWGQGTQVTVSSEPKSADKTHTCPPC PAPEAAGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPGK | HYB0516's full length sequence |
| 207 | QLQLVESGGGLVQAGGSLRLSCAASRTIFPLYAMGWFRQAPGKERE FVAGISRTTSTTLYADSVKGRFTISRDNAANTVYLQMNTLKPEDAA VYYCAARNSRTIGDVNDVDYWGQGTQLTVSSEPKSADKTHTCPPC PAPEAAGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPGK | HYB0517's full length sequence |
| 208 | QVQLVESGGGLVQAGGSLRLSCAASGRTISIYMMGWFRQAPGKGR EFVSAIMPSGSRTYSADWVKGRFTISRDNSKSTVYLQMNSLKPEDT AVYYCAAKLFRGSGDYINDYDHWGQGTQVTVSSEPKSADKTHTCP PCPAPEAAGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSREEMTKNQVSL TCLVKGFYPSDIAVEWESNGQPENNYKTTPPVLDSDGSFFLYSKLTV DKSRWQQGNVFSCSVMHEALHNHYTQKSLSLSPGK | HYB0518's full length sequence |
| 209 | QVQLVESGGGLVQPGGSLRLSCAASGSIRTVNYMGWHRQAPGKQR ELVAVVTSGGGTNYADSVKGRFTISRDDTKNTVYLQMNSLRAEDT AVYYCNAAASTYSSTVVRSFWGQGTLVTVSSEPKSADKTHTCPPCP APEAAGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTC | HYB0512-hz1's full length sequence |

TABLE A-continued

Overview of Amino Acid Sequences

| SEQ ID NO | Sequence | Description |
|---|---|---|
| | LVKGFYPSDIAVEWESNGQPENNYKTTPPVLDSDGSFFLYSKLTVD<br>KSRWQQGNVFSCSVMHEALHNHYTQKSLSLSPGK | |
| 210 | QVQLVESGGGLVQPGGSLRLSCAASGSIRTVNYMGWHRQAPGKQR<br>ELVAVVTSGGGTNYADSVKGRFTISRDNTKNTVYLQMNSLRAEDT<br>AVYYCNAAASTYSSTVVRSFWGQGTLVTVSSEPKSADKTHTCPPCP<br>APEAAGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTC<br>LVKGFYPSDIAVEWESNGQPENNYKTTPPVLDSDGSFFLYSKLTVD<br>KSRWQQGNVFSCSVMHEALHNHYTQKSLSLSPGK | HYB0512-hz2's full<br>length sequence |
| 211 | QVQLVESGGGLVQPGGSLRLSCAASGSIRTVNYMGWHRQAPGKQR<br>ELVAVVTSGGGTNYADSVKGRFTISRDDSKNTVYLQMNSLRAEDT<br>AVYYCNAAASTYSSTVVRSFWGQGTLVTVSSEPKSADKTHTCPPCP<br>APEAAGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTC<br>LVKGFYPSDIAVEWESNGQPENNYKTTPPVLDSDGSFFLYSKLTVD<br>KSRWQQGNVFSCSVMHEALHNHYTQKSLSLSPGK | HYB0512-hz3's full<br>length sequence |
| 212 | QVQLVESGGGLVQPGGSLRLSCAASGSIRTVNYMGWHRQAPGKQR<br>ELVAVVTSGGGTNYADSVKGRFTISRDNSKNTVYLQMNSLRAEDT<br>AVYYCNAAASTYSSTVVRSFWGQGTLVTVSSEPKSADKTHTCPPCP<br>APEAAGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTC<br>LVKGFYPSDIAVEWESNGQPENNYKTTPPVLDSDGSFFLYSKLTVD<br>KSRWQQGNVFSCSVMHEALHNHYTQKSLSLSPGK | HYB0512-hz4's full<br>length sequence |
| 213 | QVQLVESGGGLVQPGGSLRLSCAASGSIRTVNYMGWHRQAPGKGR<br>ELVAVVTSGGGTNYADSVKGRFTISRDDTKNTVYLQMNSLRAEDT<br>AVYYCNAAASTYSSTVVRSFWGQGTLVTVSSEPKSADKTHTCPPCP<br>APEAAGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTC<br>LVKGFYPSDIAVEWESNGQPENNYKTTPPVLDSDGSFFLYSKLTVD<br>KSRWQQGNVFSCSVMHEALHNHYTQKSLSLSPGK | HYB0512-hz5's full<br>length sequence |
| 214 | QVQLVESGGGLVQPGGSLRLSCAASGSIRTVNYMGWHRQAPGKQL<br>ELVAVVTSGGGTNYADSVKGRFTISRDDTKNTVYLQMNSLRAEDT<br>AVYYCNAAASTYSSTVVRSFWGQGTLVTVSSEPKSADKTHTCPPCP<br>APEAAGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTC<br>LVKGFYPSDIAVEWESNGQPENNYKTTPPVLDSDGSFFLYSKLTVD<br>KSRWQQGNVFSCSVMHEALHNHYTQKSLSLSPGK | HYB0512-hz6's full<br>length sequence |
| 215 | EVQLVESGGGLVQPGGSLRLSCAASGSIRTVNYMGWHRQAPGKQR<br>ELVAVVTSGGGTNYADSVKGRFTISRDDTKNTVYLQMNSLRAEDT<br>AVYYCNAAASTYSSTVVRSFWGQGTLVTVSSEPKSADKTHTCPPCP<br>APEAAGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTC<br>LVKGFYPSDIAVEWESNGQPENNYKTTPPVLDSDGSFFLYSKLTVD<br>KSRWQQGNVFSCSVMHEALHNHYTQKSLSLSPGK | HYB0512-hz7's full<br>length sequence |
| 216 | QVQLVESGGGLVQPGGSLRLSCAASGSIRTVNYMGWHRQAPGKQR<br>ELVSVVTSGGGTNYADSVKGRFTISRDDTKNTVYLQMNSLRAEDT<br>AVYYCNAAASTYSSTVVRSFWGQGTLVTVSSEPKSADKTHTCPPCP<br>APEAAGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSREEMTKNQVSLTC<br>LVKGFYPSDIAVEWESNGQPENNYKTTPPVLDSDGSFFLYSKLTVD<br>KSRWQQGNVFSCSVMHEALHNHYTQKSLSLSPGK | HYB0512-hz8's full<br>length sequence |
| 217 | EPKSADKTHTCPPCPAPEAAGGPSVFLFPPKPKDTLYITREPEVTCVV<br>VDVSHEDPEVKFNWYVDGVEVHNAKTKPREEQYNSTYRVVSVLT<br>VLHQDWLNGKEYKCKVSNKALPAPIEKTISKAKGQPREPQVYTLPP<br>SREEMTKNQVSLTCLVKGFYPSDIAVEWESNGQPENNYKTTPPVLD<br>SDGSFFLYSKLTVDKSRWQQGNVFSCSVMHEALHNHYTQKSLSLSP<br>G | Human IgG1 Fc<br>domain sequence<br>comprising $C_{220}A/$<br>$L_{234}A/L_{235}A/M_{252}Y/$<br>$S_{254}T/T_{256}E/K_{447}del$<br>mutations |
| 218 | EVQLLESGGGLVQPGGSLRLSCAASGFTFGDYAITWFRQAPGKGLE<br>GVAYISNFDGMTYYADSVKGRFTISSDNAKNTVYLQMNSLRAEDT | HYB017's full<br>length sequence |

TABLE A-continued

Overview of Amino Acid Sequences

| SEQ ID NO | Sequence | Description |
|---|---|---|
| | AVYYCAAEGRMGTHSRDSVYFWAFSALYDYWGQGTLVTVSSEPK<br>SADKTHTCPPCPAPEAAGGPSVFLFPPPKPKDTLYITREPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRE<br>EMTKNQVSLTCLVKGFYPSDIAVEWESNGQPENNYKTTPPVLDSDG<br>SFFLYSKLTVDKSRWQQGNVFSCSVMHEALHNHYTQKSLSLSPGG<br>GGGSGGGGSGGGGSQVQLVESGGGLVQPGGSLRLSCAASGSIRTVN<br>YMGWHRQAPGKQRELVAVVTSGGGTNYADSVKGRFTISRDNSKN<br>TVYLQMNSLRAEDTAVYYCNAAASTYSSTVVRSFWGQGTLVTVSS<br>A | |

EXAMPLES

The present disclosure generally described herein can be more easily understood by referring to the following examples. Those skilled in the art can draw on the content herein and appropriately improve the process parameters for implementation. It should be particularly pointed out that all similar replacements and modifications are obvious to those skilled in the art, and are all considered within the scope of protection of this disclosure.

The following examples are provided for illustrative purposes only and are not intended to limit this disclosure. These examples are not intended to indicate that the experiments described below are the only ones conducted or all the experiments performed.

Unless otherwise specified, the experimental methods used in the following examples are conventional methods. Unless otherwise specified, all the materials, reagents, and the like used in the following examples are commercially available.

Example 1: Preparation and Screening of Single-Domain Antibodies Targeting TSLP Immunization of Alpacas Two alpacas were injected subcutaneously with human TSLP-His protein (purchased from Sino Biological, TSP-H5243) at an immunization dose of 0.5 mg per animal per injection. Complete adjuvant was used for the first immunization, and incomplete adjuvant was used for subsequent immunizations, with a 2-week interval between each immunization, for a total of eight immunizations.
Determination of Serum Immune Titer Starting from the second immunization, 5 mL of blood was collected 1 week after each immunization for determination of serum immune titer. Specifically, the TSLP antigen protein used in the previous step was coated on an ELISA plate at 200 ng per well. After blocking and washing, serum samples diluted from a 1:2000 ratio were added. After incubation, binding, and washing, the plate was detected by using a secondary antibody of an anti-camelid single-domain antibody (GenScript, A01861).

Construction of Phage Display Library

After eight immunizations, 10 mL of blood was collected from each camel and combined to construct a single-domain antibody phage display library. Lymphocytes were first isolated using lymphocyte separation medium (Solarbio, P8610). The lymphocytes were treated and lysed with RNA extraction reagent (TaKaRa, 9109), and impurities were removed with chloroform. RNAs were precipitated with isopropanol and washed with 75% ethanol. After drying at room temperature, the RNAs were dissolved in water for injection. Next, the RNAs were reverse transcribed into cDNAs using a reverse transcription kit (Thermo Scientific, K1622). The DNAs encoding VHH were then amplified by nested PCR, digested with Sfi I, and ligated to the display vector that was also digested with Sfi I using T4 DNA ligase. The ligation product was purified and electroporated into TG1 competent cells, which were then infected with M13KO7 helper phage to construct the phage display library. The eventually-constructed libraries (HYC9 and HYBC10) had effective library capacities of $1 \times 10^9$ and $3.4 \times 10^9$ cfu, respectively.

Panning of the Phage Display Library

The TSLP antigen (TSLP-His-Avi, ACROBiosystems, TSP-H82E0) was loaded onto magnetic beads coupled with streptavidin (Thermo Scientific, 88817) to pan the HYC9 and HYBC10 phage libraries. The panning process and results are shown in Table 1. After two rounds of panning, the eluted phages in the antigen group were significantly enriched compared to the control group, with enrichment factors of 15.9 times.

TABLE 1

Phage Library Panning Data
TSLP-His-avi panning data-library HYC9&HYC10

| Rounds | Experimental Group | Beads and Loaded Protein | Input Phage Volume (cfu) | Washing Conditions | Eluted Phage Volume (cfu) | Enrichment Factor Compared to Control Group |
|---|---|---|---|---|---|---|
| 1st | Antigen Group | 100 µL beads loaded with 3 µg TSLP-His-Avi | $1.2 \times 10^{12}$ 1 mL | 0.1% PBST 16 rpm 1 min × 6 | $6.5 \times 10^7$ | 1.3 |

TABLE 1-continued

| | | | | | | |
|---|---|---|---|---|---|---|
| Rounds | Experimental Group | Beads and Loaded Protein | Input Phage Volume (cfu) | Washing Conditions | Eluted Phage Volume (cfu) | Enrichment Factor Compared to Control Group |
| | Control Group | 100 µL beads loaded with 3 µg Avi-tag antigen of unrelated target | $1.2 \times 10^{12}$ 1 mL | | $5.2 \times 10^{7}$ | — |
| 2nd | Antigen Group | 100 µL beads loaded with 3 µg TSLP-His-Avi | $2.6 \times 10^{10}$ 1 mL | 0.1% PBST 16 rpm 2 min × 6 | $3.5 \times 10^{8}$ | 15.9 |
| | Control Group | 100 µL beads loaded with 3 µg Avi-tag antigen of unrelated target | $2.6 \times 10^{10}$ 1 mL | | $2.2 \times 10^{7}$ | — |

Phage Library Panning Data
TSLP-His-avi panning data-library HYC9&HYC10

Monoclonal Phage-Based Screening

TG1 bacteria in the logarithmic growth phase were infected using the enriched phage library eluted from the previous step. After dilution, the TG1 bacteria were plated and incubated. Monoclonal colonies were picked and inoculated into 2×YT medium containing Carb and M13KO7 helper phage for overnight incubation. On the second day, the culture plate was centrifuged at 4200 rpm, and the supernatant was collected for phage ELISA assay. The wells coated with TSLP-His protein were used as the test wells, and the wells coated with unrelated target protein were used as the control wells. Anti-M13 antibody conjugated with HRP (horseradish peroxidase) (Sino Biological, 11973-MM05T-H) was used as the secondary antibody. Bacterial solutions of clones with $OD_{450 \, nm}$ readings above 1.0 in the test wells and below 0.1 in the control wells were selected for plasmid extraction and gene sequencing. After translating the obtained DNA sequences into amino acid sequences, sequence alignment was performed. Repeated sequences and similar sequences with less than 2 amino acid differences in a CDR regions (a CDR region was partitioned using the AbM method) were removed. A total of 28 unique sequences were finally obtained.

Example 2: Blocking Function Assay Based on Anti-TSLP Periplasmic Single-Domain Antibodies Crude Extracts The plasmids containing the unique sequences were transformed into BL21 Rosetta (DE3) competent cells, which were then inoculated into 2 mL of 2×YT medium containing Carb antibiotic. When the $OD_{600}$ reached 0.4, 3 mL of 2×YT medium containing IPTG and Carb was added to achieve a final IPTG concentration of 0.1 mM, and the culture was continued overnight at 28° C. On the second day, the bacterial solution was centrifuged at 4200 rpm and 4° C. for 20 minutes. Subsequently, the bacterial pellet was resuspended in 0.5 mL of PBS and subjected to three freeze-thaw cycles between −80° C. and 37° C. to release the single-domain antibodies from the periplasmic space. After centrifugation at 10000 rpm and 4° C. for 15 minutes, the supernatant was collected to obtain the crude extracts of the periplasmic single-domain antibodies (10×).

Said crude extracts of the single-domain antibodies were then used for blocking ELISA assays of human TSLPR&IL-7Rα-Fc (ACROBiosystems, TSR-H525a) and TSLP-His-Avi (ACROBiosystems, TSP-H82E0). First, human TSLPR&IL-7Rα-Fc was coated on the plate at 4° C. overnight at a concentration of 500 ng per well. On the second day, the plate was blocked with 1% BSA at room temperature for 2 hours. The crude extracts diluted from the stock solution in a 1:2 gradient were mixed with TSLP-His-Avi at a final concentration of 0.012 µg/mL in equal volume. Two concentration points (final concentrations of 5× and 2.5×) were set for the crude extracts. The crude extract and TSLP-His-Avi were incubated at room temperature for 30 minutes, then transferred to the plate that had been coated with TSLPR&IL-7Rα-Fc and blocked, and incubated at room temperature for 1 hour. The plate was washed, then detected by the addition of streptavidin-HRP (Sangon Biotech, D111054) at a ratio of 1:3000. Tezepelumab biosimilar was used as the positive reference, and the crude extract of single-domain antibodies targeting an unrelated target was used as the negative control. The absorbance at 450 nm was read using a microplate reader (BioTek, Synergy H1MF).

The results showed that among the 28 clones, 16 clones exhibited a significant blocking efficacy against the binding of TSLP to TSLPR&IL-7Rα. In addition, the binding ability of the crude extracts of the 28 clones to TSLP coated on the plate was also tested, and it was found that most of them had a significant binding to TSLP, while they did not bind to the control wells coated with unrelated target proteins (data not shown).

Example 3: Expression and In Vitro Activity Assay of Anti-TSLP Antibody

The $V_HH$ sequences of the 16 clones obtained above were connected to the N-terminus of the human IgG1 Fc domain (containing the $C_{220}A/L_{234}A/L_{235}A$ mutations, the sequence is as shown in SEQ ID NO: 160), and transiently transfected into HEK293 cells for expression and purification. The resulting molecules were named as HYB0101 to HYB0116 (their full-length sequences are as shown in SEQ ID NOs: 161-176, respectively, and their variable region sequences are as shown in SEQ ID NOs: 4, 8, 12, 16, 20, 24, 28, 32, 36, 40, 44, 48, 52, 56, 60, and 64, respectively). Subsequently, the inhibition efficacy of these molecules against human TSLP-induced CCL-17 release from human PBMCs was determined.

Gradient-diluted TSLP heavy chain antibody samples and the mix dilution of human TSLP (ACROBiosystems, TSP-H5243) and IL-33 (ACROBiosystems, IL3-H52H7) were added into a 96-well cell culture plate at a 1:1 volume ratio (50 μL each), with a final concentration of 0.5 ng/mL for human TSLP and 2 ng/mL for human IL-33. Then, PBMCs (Oribiotech, Z0641) were added to the 96-well cell culture plate at a density of 100,000 cells/100 μL/well and cultured in a 37° C./5% $CO_2$ incubator for 48 hours. After the culture was completed, the secretion level of CCL-17 in the culture supernatant was detected using the Human TARC ELISA Kit (BioSharp, BSEH-220-96T).

Figure 1:
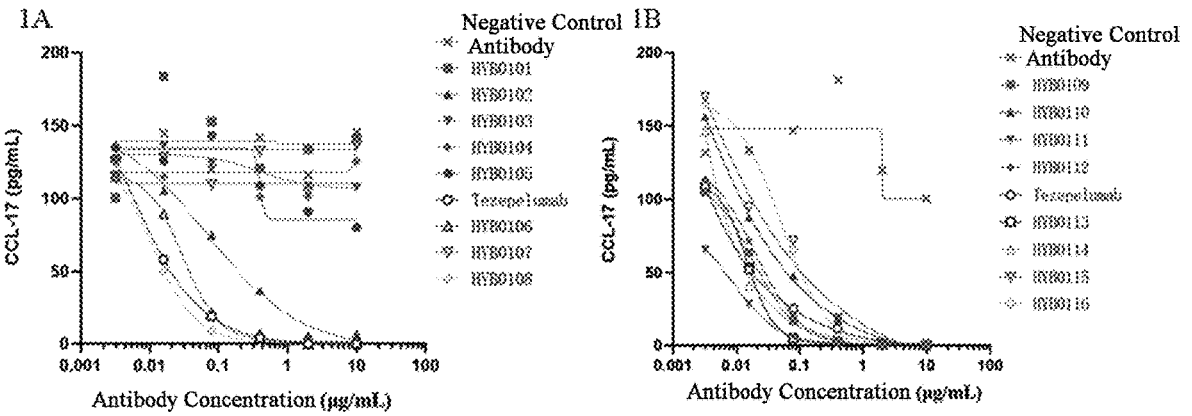
FIG. 1: Inhibition efficacy results of the initial TSLP heavy-chain antibody on TSLP-induced CCL-17 release from human PBMCs. The experiment was performed in single replicate wells and divided into two plates (see FIG. 1A and FIG. 1B).

As shown in FIG. 1, most of the molecules exhibited an effective blocking efficacy against human TSLP-induced CCL-17 release from human PBMCs, among which HYB0111 had a relatively better blocking effect.

Example 4: Humanization and Activity Determination of TSLP Antibody

The structure of antibody HYB0111 was modeled using SWISS-MODEL. Based on the obtained structure, humanization mutations of the camelid amino acid sites in the framework regions were evaluated. The human germline genes $V_{3-23}$*01 and $J_1$*01 were used as the target sequences for humanization mutations. Amino acid sites located on the surface of the antibody structure and not adjacent to the CDRs were mutated first, while those located internally within the antibody structure (buried) and adjacent to the CDRs were mutated later.

According to the above principles, several humanized antibody sequences were designed: HYB0111-hz1 to HYB0111-hz4 (their full-length sequences are as shown in SEQ ID NO: 177-180, respectively, and their variable region sequences are as shown in SEQ ID NOs: 65-68, respectively). These sequences were then transiently transfected into HEK293 cells for expression. The blocking efficacy of HYB0111-hz2 to HYB0111-hz4 at the cellular level was detected using the method as described in Example 3 (HYB0111-hz1 had a relatively lower degree of humanization).

The results are shown in FIG. 2, which indicates that HYB0111-hz2 to HYB0111-hz4 all exhibited a good blocking efficacy against human TSLP, with HYB0111-hz2 showing the best efficacy.

Example 5: Modification and Activity Validation Based on HYB0111-Hz2

When HYB0111-hz2 was transiently transfected and expressed in HEK293 cells in Example 4, and purified using a Protein A column, the yield of HYB0111-hz2 was only 282 mg/L. Compared with other projects in our laboratory, this yield of the single-domain antibody was relatively low. Therefore, a series of revertants of HYB0111-hz2 were designed: HYB0111-hz5 to HYB0111-hz14 (their variable region sequences are as shown in SEQ ID NO: 69 to SEQ ID NO: 78, respectively). These variants were then transiently transfected in HEK293 cells in the same batch for expression and purification. It was found that variant HYB0111-hz9 had a higher expression level (372 mg/L).

To verify the activity of HYB0111-hz9, its inhibition efficacy against TSLP-mediated CCL-17 release from PBMCs was detected according to the method described in Example 3. The results are shown in FIG. 3, which indicates that HYB0111-hz9 maintained the higher blocking efficacy of HYB0111-hz2 and was significantly better than the reference drug Tezepelumab.

Example 6: Preparation and Screening of Single-Domain Antibodies Targeting IL-33

Immunization of Alpacas

Human IL-33-His protein (purchased from Sino Biological, IL3-H52H7) were used for subcutaneous injection to immunize three alpacas (animals were numbered as B1, B2, and C3) at an immunization dose of 0.5 mg per animal per injection. Complete adjuvant was used for the first immunization, and incomplete adjuvant was used for subsequent immunizations, with a 2-week interval between each immunization, for a total of eight or six immunizations (depending on the serum immune titer detected).

Serum Immune Titer Determination

Starting from the second immunization, 5 mL of blood was collected 1 week after each immunization for serum immune titer determination. Specifically, the IL-33 antigen protein used in the previous step was coated on an ELISA plate at 200 ng per well. After blocking and washing, serum samples diluted from a 1:2000 ratio were added. After incubation, binding and washing, the plate was detected using a secondary antibody of an anti-camelid single-domain antibody (GenScript, A01861).

Construction of Phage Display Library

After eight or six immunizations, 10 mL of blood was collected from each camel and combined to construct a single-domain antibody phage display library. Lymphocytes were first isolated using lymphocyte separation medium (Solarbio, P8610). The lymphocytes were treated and lysed with RNA extraction reagent (TaKaRa, 9109), and impurities were removed with chloroform. RNAs were precipitated with isopropanol and washed with 75% ethanol. After drying at room temperature, the RNAs were dissolved in water for injection. Next, the RNAs were reverse transcribed into cDNA using a reverse transcription kit (Thermo Scientific, K1622). The DNAs encoding VHH were then amplified by nested PCR, digested with Sfi I, and ligated to the display vector that was also digested with Sfi I using T4 DNA ligase. The ligation product was purified and electroporated into TGT competent cells, which were then infected with M13KO7 helper phage to construct the phage display library. The eventually-constructed libraries (HYB1-8, HYB2-8 and H4YBC3-6) had effective library capacities of $1.3 \times 10^9$, $2.3 \times 10^9$ and $1.4 \times 10^{10}$ cfu, respectively.

Panning of the Phage Display Library

The IL-33 antigen (IL-33-His-Avi, Beijing ACROBiosystems, TSP-H82E0) was loaded onto magnetic beads coupled with streptavidin (Thermo Scientific, 88817) to pan the three phage libraries. The panning process and results are shown in Table 2. After one or two rounds of panning, the eluted phages in the antigen group were significantly enriched compared to the control group.

TABLE 2

| Rounds | Experimental Group | Beads and Loaded Protein | Input Phage Volume (cfu) | Washing Conditions | Eluted Phage Volume (cfu) | Enrichment Factor Compared to Control Group |
|---|---|---|---|---|---|---|
| | | Phage Library Panning Data | | | | |
| | | IL-33-His-avi panning data-library HYB1-8 | | | | |
| 1st | Antigen Group | 100 μL beads loaded with 2.4 μg IL-33-His-Avi | $3 \times 10^{12}$ 1 mL | 0.1% PBST 16 rpm 1 min × 6 | $1.3 \times 10^8$ | 37.1 |
| | Control Group | 100 μL beads loaded with 2.4 μg Avi antigen of unrelated target | $3 \times 10^{12}$ 1 mL | | $3.5 \times 10^6$ | — |
| | | IL-33-His-avi panning data-library HYB2-8 | | | | |
| 1st | Antigen Group | 100 μL beads loaded with 2.4 μg IL-33-His-Avi | $3 \times 10^{12}$ 1 mL | 0.1% PBST 16 rpm 1 min × 6 | $2.5 \times 10^7$ | 3.3 |
| | Control Group | 100 μL beads loaded with 2.4 μg Avi antigen of unrelated target | $3 \times 10^{12}$ 1 mL | | $7.5 \times 10^6$ | — |
| 2nd | Antigen Group | 100 μL beads loaded with 2.4 μg IL-33-His-Avi | $1 \times 10^{10}$ 1 mL | 0.1% PBST 16 rpm 1 min × 6 | $1.5 \times 10^8$ | 1578.9 |
| | Control Group | 100 μL beads loaded with 2.4 μg Avi antigen of unrelated target | $1 \times 10^{10}$ 1 mL | | $9.5 \times 10^4$ | — |
| | | IL-33-His-avi panning data-libraryHYC3-6 | | | | |
| 1st | Antigen Group | 100 μL beads loaded with 2.4 μg IL-33-His-Avi | $3 \times 10^{12}$ 1 mL | 0.1% PBST 16 rpm 1 min × 6 | $1.2 \times 10^8$ | 9.2 |
| | Control Group | 100 μL beads loaded with 2.4 μg Avi antigen of unrelated target | $3 \times 10^{12}$ 1 mL | | $1.3 \times 10^7$ | — |

Monoclonal Phage-Based Screening

TG1 bacteria in the logarithmic growth phase were infected using the enriched phage library eluted from the previous step. After dilution, the TG1 bacteria were plated and incubated. Monoclonal colonies were picked and inoculated into 2×YT medium containing Carb and M13KO7 helper phage for overnight incubation. On the second day, the culture plate was centrifuged at 4200 rpm, and the supernatant was collected for phage ELISA assay. The wells coated with IL-33-His protein were used as the test wells, and the wells coated with unrelated target protein were used as the control wells. Anti-M13 antibody conjugated with HRP (horseradish peroxidase) (Sino Biological, 11973-MM05T-H) was used as the secondary antibody. Bacterial of clones with $OD_{450\ nm}$ readings above 1.0 in the test wells and below 0.1 in the control wells were selected for plasmid extraction and gene sequencing. After translating the obtained DNA sequences into amino acid sequences, sequence alignment was performed. Repeated sequences and similar sequences with less than 2 amino acid differences in a CDR regions (a CDR region was partitioned using the AbM method) were removed. A total of 128 unique sequences were finally obtained.

Example 7: Blocking Function Assay Based on IL-33 Periplasmic Single-Domain Antibodies Crude Extract The plasmids containing the unique sequences were transformed into BL21 Rosetta (DE3) competent cells, which were then inoculated into 2 mL of 2×YT medium containing Carb antibiotic. When the $OD_{600}$ reached 0.4, 3 mL of 2×YT medium containing IPTG and Carb was added to achieve a final IPTG concentration of 0.1 mM, and the culture was continued overnight at 28° C. On the second day, the bacterial solution was centrifuged at 4200 rpm and 4° C. for 20 minutes. Subsequently, the bacterial pellet was resuspended in 0.5 mL of PBS and subjected to three freeze-thaw cycles between −80° C. and 37° C. to release the single-domain antibodies from the periplasmic space. After centrifugation at 10000 rpm and 4° C. for 15 minutes, the supernatant was collected to obtain the crude extracts of the periplasmic single-domain antibodies (10×).

Said crude extracts of the single-domain antibodies were then used for blocking ELISA assays of human IL-1RL1-Fc (ACROBiosystems, IL1-H5250) and IL33-His-Avi (ACRO-Biosystems, IL3-H82H5). First, human IL-1RL1-Fc was coated in the plate at 4° C. overnight at a concentration of 300 ng per well. On the second day, the plate was blocked with 1% BSA at room temperature for 2 hours. The crude extracts diluted from the stock solution in a 1:2 gradient were mixed with IL33-His-Avi at a final concentration of 0.025 μg/mL in equal volume. Two concentration points (final concentrations of 5× and 2.5×) were set for the crude extracts. After incubating crude extract and IL33-His-Avi at room temperature for 30 minutes, they were transferred to the plate that had been coated with IL-1RL1-Fc and blocked, and incubated at room temperature for 1 hour. The plate was washed and detected by the addition of streptavidin-HRP (Sangon Biotech, DI11054) at a ratio of 1:6000. Itepekimab biosimilar was used as the positive reference, and the crude extract of single-domain antibodies targeting an unrelated target was used as the negative control. The absorbance at 450 nm was read using a microplate reader (BioTek, Synergy H1MF).

The results showed that among the 128 clones, 18 clones exhibited a significant blocking efficacy against the binding of IL-33 to IL-1RL1. In addition, the binding ability of the crude extracts of the 128 clones to IL-33 coated on the plate was also tested, and it was found that most of them had obvious binding, while they did not bind to the control wells coated with unrelated target proteins (data not shown).

Example 8: Expression and In Vitro Activity Determination of IL-33 Heavy Chain Antibody The $V_HH$ sequences of the 18 clones obtained above were connected to the N-terminus of the human IgG1 Fc domain (containing the $C_{220}A/L_{234}A/L_{235}A$ mutations, the sequence is as shown in SEQ ID NO: 160), and transiently transfected into HEK293 cells for expression and purification. The resulting molecules were named as HYB0501 to HYB0518 (their full-length sequences are as shown in SEQ ID NOs: 191-208, respectively, and their variable region sequences are as shown in SEQ ID NO: 82, 86, 90, 94, 98, 102, 106, 110, 114, 118, 122, 126, 130, 134, 138, 142, 146, and 150, respectively). Subsequently, the inhibition efficacy of these molecules against human IL-33-induced IL-5 release from human KU812 cells was determined.

KU812 cells were seeded into a 96-well cell culture plate at a density of 500,000 cells/100 μL/well. Gradient-diluted IL-33 heavy chain antibody samples were added to the cell culture plate at 50 μL/well, followed by incubation at 37° C. for 0.5 hours. Subsequently, the dilution of human IL-33-His (Beijing ACROBiosystems, IL3-H52H7) was added to the cell plate at 50 μL/well, with a final concentration of 10 ng/mL of human IL-33-His. The cells were then cultured in a 37° C./5% $CO_2$ incubator for 72 hours. After the culture period, the secretion level of IL-5 in the culture supernatant was detected using the Human IL-5 ELISA Kit (BioSharp, BSEH-006-96T).

As shown in FIG. 4, at the cellular level, both HYB0509 and HYB0512 molecules effectively blocked the IL-33-induced IL-5 release from human KU812 cells, with HYB0512 demonstrating a relatively better blocking effect.

Example 9: Humanization and Activity Determination of IL-33 Antibody

The structure of antibody HYB0512 was modeled using SWISS-MODEL. Based on the obtained structure, humanization mutations of the camelid amino acid sites in the framework regions were evaluated. The human germline genes $V_{3-66}*01$ and $J_1*01$ were used as the target sequences for humanization mutations. Amino acid sites located on the surface of the antibody structure and not adjacent to the CDRs were mutated first, while those located internally within the antibody structure (buried) and adjacent to the CDRs were mutated later.

According to the above principles, several humanized antibody sequences were designed: HYB0512-hz1 to HYB0512-hz8 (their full-length sequences are as shown in SEQ ID NOs: 209-216, respectively, and their variable region sequences are as shown in SEQ ID NOs: 151-158, respectively). These sequences were then transiently transfected into HEK293 cells for expression. The blocking efficacy of HYB0512-hz1 to HYB0512-hz8 at the cellular level was detected using the method as described in Example 8.

As shown in FIG. 5, except for the variants HYB0512-hz6 and HYB0512-hz7, all other humanized variant molecules maintained the in vitro blocking activity of the parental molecule HYB0512 against IL-33. Taking into account the factors, such as the degree of humanization, transient transfection expression yield, and preliminary drugability assessment results, etc., the variant HYB0512-hz4 was selected for further validation.

Example 10: Assay of Inhibition Efficacy of IL-33 Antibody on Human IL-33-Induced IFN-γ Release from PBMCs An experimental system using IL-33 to stimulate PBMCs to release IFN-γ was employed to further validate the in vitro inhibitory activity of HYB0512-hz4 against IL-33. The experiment was conducted in triple replicate wells, with Itepekimab and Etokimab used as control molecules. The specific steps are as follows:

PBMCs (Oribiotech, Z0654) were resuspended in fresh medium and incubated and recovered in a 37° C./5% $CO_2$ incubator for 3-5 hours. During this period, gradient-diluted IL-33 heavy chain antibody samples were added to a 96-well cell culture plate at 50 μL per well. Subsequently, a dilution of human IL-33-His (Beijing ACROBiosystems, IL3-H52H7) and human IL-12 (Beijing ACROBiosystems, IL2-H5210) were added to the cell culture plate at 50 μL per well, and incubated at 37° C. for 1 hour. The final concentration of human IL-33-His was 1 ng/mL, and the final concentration of human IL-12 was 20 ng/mL. After incubation, PBMCs were added to the 96-well cell culture plate at 40,000 cells/50 μL/well and cultured overnight in a 37° C./5% $CO_2$ incubator. On the second day, the secretion level of IFN-γ in the culture supernatant was detected using the Human IFN-γ ELISA Kit (Biosharp, BSEH-017-96T).

As shown in FIG. 6, HYB0512-hz4 exhibited a good in vitro inhibitory activity against IL-33.

Example 11: Construction of Bispecific Antibody Simultaneously Targeting TSLP and IL-33

The single-domain antibodies (sdAb) HYB0111-hz9 and HYB0512-hz4 prepared after camelid immunization and humanization were used for the portion targeting TSLP and IL-33 respectively. In the construction of the bispecific antibody molecule, a human IgG1 Fc domain comprising $C_{220}A/L_{234}A/L_{235}A/M_{252}Y/S_{254}T/T_{256}E/K447del$ mutations (the sequence is as shown in SEQ ID NO: 217) was used. The heavy chain single-domain antibody HYB0111-hz9 targeting TSLP was connected to the N-terminus of the Fc domain, and the heavy chain single-domain antibody HYB0512-hz4 targeting IL-33 was connected to the C-terminus of the Fc domain via a $(GGGGS)_3$ linker, with a single alanine extension introduced to the C-terminus of HYB0512-hz4. The constructed bispecific antibody molecule was named as HYB017 (the full-length sequence is as shown in SEQ ID NO: 218). HYB017 was transiently transfected into HEK293 cells for expression and purification, and it was found to have a good yield and SEC monopeak purity.

Example 12: Inhibition Assay of Bispecific Antibody on TSLP-Induced Proliferation of huTSLPR&huIL-7Rα/BaF3 Cells huTSLPR&huIL-7Ru/BaF3 cells in logarithmic growth phase were resuspended in fresh RPMI-1640 medium containing 10% FBS and added to a 96-well white-wall transparent-bottom cell culture plate at 2,500 cells/40 μL per well. Then, the gradient-diluted HYB017 solution at 40 μL/well and the TSLP (R&D, 1398-TS) solution at 20 μL/well (both were prepared in RPMI-1640 medium containing 10% FBS) were added successively. The final concentration of TSLP was 0.5 ng/mL. The plate was then incubated in a 37° C./5% $CO_2$ incubator for 72 hours. After incubation, the plate was taked out from the incubator, and 100 μL/well of CellTiter-Glo® (Promega, G7573) detection reagent was added. After incubating at room temperature for 30 minutes, the luminescence values were read on a microplate reader.

As shown in FIG. 7, compared with the control drug Tezepelumab, HYB017 exhibited a significantly superior inhibition efficacy against TSLP-mediated proliferation of TSLPR&IL-7Rα/BaF3 cells, with $EC_{50}$ values of 1.393 and 0.034 μg/mL, respectively.

Example 13: Assay of Inhibition of Bispecific Antibody on TSLP-Induced CCL-17 Release from PBMCs A gradient-diluted HYB017 sample and a mixed dilution of human TSLP (Beijing ACROBiosystems, TSP-H5243) and IL-33 (Beijing ACROBiosystems, IL3-H52H7) were added to a 96-well cell culture plate in a 1:1 volume ratio (50 μL each). The final concentration of human TSLP was 0.5 ng/mL, and the final concentration of human IL-33 was 2 ng/mL. Then, PBMCs (Oribiotech, Z0641) were added to the 96-well cell culture plate at 100,000 cells/100 μL/well and cultured in a 37° C./5% $CO_2$ incubator for 48 hours. After culturing, the secretion level of CCL-17 in the culture supernatant was detected using the Human TARC ELISA Kit (Biosharp, BSEH-220-96T).

As shown in FIG. 8, compared with the control drug Tezepelumab, HYB017 exhibited a significantly superior inhibition efficacy against TSLP-induced CCL-17 release from PBMCs, with $EC_{50}$ values of 0.072 and 0.004 μg/mL, respectively.

Example 14: Assay of Inhibition Efficacy of Bispecific Antibody on IL-33-Mediated Intracellular Signaling Pathway in huIL-1RL1&IL-1RAP Reporter Gene Cells A gradient-diluted HYB017 sample and a dilution of human IL-33 (Beijing ACROBiosystems, IL3-H52H7) were mixed in a 1:1 volume ratio (30+30 μL) and added to a 96-well sample plate, and incubated at room temperature for 30 minutes. huIL-1RL1&IL-1RAP reporter gene cells (Cobioer, CBP74176) in the logarithmic phase were centrifuged to remove the supernatant, resuspended in fresh RPMI-1640 medium containing 10% FBS, and adjusted to a cell density of $6.25×10^5$/mL. The cells were then added to a 96-well white-wall transparent-bottom cell culture plate at 80 μL/well, followed by the addition of 20 μL/well of the HYB017-IL33 incubation solution, with a final concentration of IL-33 of 10 μg/mL. The plate was incubated in the incubator for 6 hours. After incubation, 100 μL/well of the fluorescent detection reagent (Cobioer, CBPH0001) was added, gently mixed, and incubated at room temperature for 3 minutes. The luminescence values were read using a multimode microplate reader (Biotek, Synergy H1).

As shown in FIG. 9, the bispecific antibody HYB017 exhibited a clear blockade efficacy against the fluorescent signal of the reporter gene cells mediated by IL-33. Although the blockade efficacy was weakened than the monoclonal single-domain antibody HYB0512-hz4 targeting IL-33, such weakening was speculated to be caused by the increased molecular weight of the bispecific antibody and the steric hindrance of the Fc end.

Example 15: Determination of Affinity (KD) of Bispecific Antibody Against Antigens The affinity of the HYB017 molecule against human TSLP protein (Beijing ACROBiosystems, TSP-H5243) and human IL-33 protein (Beijing ACROBiosystems, IL3-H52H7) was measured using Biacore 8K. HYB017 was captured on a Protein A chip (Cytiva, 29127556) at a flow rate of 10 μL/min, and then different concentrations of antigen protein were flowed in at a flow rate of 30 μL/min. The running buffer was HBS-EP$^+$, with a binding time of the antigen and the antibody of 120 seconds and a dissociation time of 1600 seconds (for TSLP) or 1800 seconds (for IL-33). After the detection, the built-in software of the instrument was used to fit the data according to the 1:1 binding model to calculate the association rate constant $K_{on}$, dissociation rate constant $K_{off}$, and equilibrium dissociation constant $K_D$ values of the antibody-antigen binding.

As shown in Table 3, HYB017 exhibited a good affinity against both antigens, superior to the control drug.

TABLE 3

Affinity Detection Data

| Captured Antibody | Antigen Flowed in | $K_{on}$ (1/MS) | $K_{off}$ (1/S) | $K_D$ (M) |
|---|---|---|---|---|
| HYB017 | TSLP | $1.38 \times 10^6$ | $1.07 \times 10^{-5}$ | $7.76 \times 10^{-12}$ |
| Tezepelumab | | $2.94 \times 10^7$ | $3.76 \times 10^{-4}$ | $1.28 \times 10^{-11}$ |

TABLE 3-continued

Affinity Detection Data

| Captured Antibody | Antigen Flowed in | $K_{on}$ (1/MS) | $K_{off}$ (1/S) | $K_D$ (M) |
|---|---|---|---|---|
| HYB017 | IL-33 | $5.85 \times 10^4$ | $3.56 \times 10^{-8}$ | $6.08 \times 10^{-13}$ |
| Etokimab | | $5.61 \times 10^5$ | $1.96 \times 10^{-4}$ | $3.49 \times 10^{-10}$ |

It should be understood that although the disclosure has been illustratively described based on its preferred embodiments, it should not be limited to the above examples. For those skilled in the art, the disclosure may have various modifications and variations. The selection and application of specific technical solutions can be adjusted and changed according to specific needs. Therefore, for those skilled in the art, several simple replacements can still be made without departing from the concepts and principles of the present disclosure, and these should all be included within the scope of protection of the disclosure.

What is claimed is:

1. A bispecific antigen-binding molecule comprising a first antigen-binding functional region and a second antigen-binding functional region, wherein the first antigen-binding functional region comprises at least one immunoglobulin single variable domain specifically binding to TSLP, and the immunoglobulin single variable domain specifically binding to TSLP comprises:

1) A CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3;

2) A CDR1 comprising the amino acid sequence set forth in SEQ ID NO: 5, a CDR2 comprising the amino acid sequence set forth in SEQ ID NO: 6, and a CDR3 comprising the amino acid sequence set forth in SEQ ID NO: 7;

3) A CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11;

4) A CDR1 comprising the amino acid sequence set forth in SEQ ID NO: 13, a CDR2 comprising the amino acid sequence set forth in SEQ ID NO: 14, and a CDR3 comprising the amino acid sequence set forth in SEQ ID NO: 15;

5) A CDR1 comprising the amino acid sequence set forth in SEQ ID NO: 17, a CDR2 comprising the amino acid sequence set forth in SEQ ID NO: 18, and a CDR3 comprising the amino acid sequence set forth in SEQ ID NO: 19;

6) A CDR1 comprising the amino acid sequence set forth in SEQ ID NO: 21, a CDR2 comprising the amino acid sequence set forth in SEQ ID NO: 22, and a CDR3 comprising the amino acid sequence set forth in SEQ ID NO: 23;

7) A CDR1 comprising the amino acid sequence set forth in SEQ ID NO: 25, a CDR2 comprising the amino acid sequence set forth in SEQ ID NO: 26, and a CDR3 comprising the amino acid sequence set forth in SEQ ID NO: 27;

8) A CDR1 comprising the amino acid sequence set forth in SEQ ID NO: 29, a CDR2 comprising the amino acid sequence set forth in SEQ ID NO: 30, and a CDR3 comprising the amino acid sequence set forth in SEQ ID NO: 31;

9) A CDR1 comprising the amino acid sequence set forth in SEQ ID NO: 33, a CDR2 comprising the amino acid sequence set forth in SEQ ID NO: 34, and a CDR3 comprising the amino acid sequence set forth in SEQ ID NO: 35;

10) A CDR1 comprising the amino acid sequence set forth in SEQ ID NO: 37, a CDR2 comprising the amino acid sequence set forth in SEQ ID NO: 38, and a CDR3 comprising the amino acid sequence set forth in SEQ ID NO: 39;

11) A CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43;

12) A CDR1 comprising the amino acid sequence set forth in SEQ ID NO: 45, a CDR2 comprising the amino acid sequence set forth in SEQ ID NO: 46, and a CDR3 comprising the amino acid sequence set forth in SEQ ID NO: 47;

13) A CDR1 comprising the amino acid sequence set forth in SEQ ID NO: 49, a CDR2 comprising the amino acid sequence set forth in SEQ ID NO: 50, and a CDR3 comprising the amino acid sequence set forth in SEQ ID NO: 51;

14) A CDR1 comprising the amino acid sequence set forth in SEQ ID NO: 53, a CDR2 comprising the amino acid sequence set forth in SEQ ID NO: 54, and a CDR3 comprising the amino acid sequence set forth in SEQ ID NO: 55;

15) A CDR1 comprising the amino acid sequence set forth in SEQ ID NO: 57, a CDR2 comprising the amino acid sequence set forth in SEQ ID NO: 58, and a CDR3 comprising the amino acid sequence set forth in SEQ ID NO: 59; or 16) A CDR1 comprising the amino acid sequence set forth in SEQ ID NO: 61, a CDR2 comprising the amino acid sequence set forth in SEQ ID NO: 62, and a CDR3 comprising the amino acid sequence set forth in SEQ ID NO: 63; and the second antigen-binding functional region comprises at least one immunoglobulin single variable domain specifically binding to IL-33, and the immunoglobulin single variable domain specifically binding to IL-33 comprises:

1) A CDR1 comprising the amino acid sequence set forth in SEQ ID NO: 79, a CDR2 comprising the amino acid sequence set forth in SEQ ID NO: 80, and a CDR3 comprising the amino acid sequence set forth in SEQ ID NO: 81;

2) A CDR1 comprising the amino acid sequence set forth in SEQ ID NO: 83, a CDR2 comprising the amino acid sequence set forth in SEQ ID NO: 84, and a CDR3 comprising the amino acid sequence set forth in SEQ ID NO: 85;

3) A CDR1 comprising the amino acid sequence set forth in SEQ ID NO: 87, a CDR2 comprising the amino acid sequence set forth in SEQ ID NO: 88, and a CDR3 comprising the amino acid sequence set forth in SEQ ID NO: 89;

4) A CDR1 comprising the amino acid sequence set forth in SEQ ID NO: 91, a CDR2 comprising the amino acid sequence set forth in SEQ ID NO: 92, and a CDR3 comprising the amino acid sequence set forth in SEQ ID NO: 93;

5) A CDR1 comprising the amino acid sequence set forth in SEQ ID NO: 95, a CDR2 comprising the amino acid sequence set forth in SEQ ID NO: 96, and a CDR3 comprising the amino acid sequence set forth in SEQ ID NO: 97;

6) A CDR1 comprising the amino acid sequence set forth in SEQ ID NO: 99, a CDR2 comprising the amino acid sequence set forth in SEQ ID NO: 100, and a CDR3 comprising the amino acid sequence set forth in SEQ ID NO: 101;

7) A CDR1 comprising the amino acid sequence set forth in SEQ ID NO: 103, a CDR2 comprising the amino acid sequence set forth in SEQ ID NO: 104, and a CDR3 comprising the amino acid sequence set forth in SEQ ID NO: 105;

8) A CDR1 comprising the amino acid sequence set forth in SEQ ID NO: 107, a CDR2 comprising the amino acid sequence set forth in SEQ ID NO: 108, and a CDR3 comprising the amino acid sequence set forth in SEQ ID NO: 109;

9) A CDR1 comprising the amino acid sequence set forth in SEQ ID NO: 111, a CDR2 comprising the amino acid sequence set forth in SEQ ID NO: 112, and a CDR3 comprising the amino acid sequence set forth in SEQ ID NO: 113;

10) A CDR1 comprising the amino acid sequence set forth in SEQ ID NO: 115, a CDR2 comprising the amino acid sequence set forth in SEQ ID NO: 116, and a CDR3 comprising the amino acid sequence set forth in SEQ ID NO: 117;

11) A CDR1 comprising the amino acid sequence set forth in SEQ ID NO: 119, a CDR2 comprising the amino acid sequence set forth in SEQ ID NO: 120, and a CDR3 comprising the amino acid sequence set forth in SEQ ID NO: 121;

12) A CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125;

13) A CDR1 comprising the amino acid sequence set forth in SEQ ID NO: 127, a CDR2 comprising the amino acid sequence set forth in SEQ ID NO: 128, and a CDR3 comprising the amino acid sequence set forth in SEQ ID NO: 129;

14) A CDR1 comprising the amino acid sequence set forth in SEQ ID NO: 131, a CDR2 comprising the amino acid sequence set forth in SEQ ID NO: 132, and a CDR3 comprising the amino acid sequence set forth in SEQ ID NO: 133;

15) A CDR1 comprising the amino acid sequence set forth in SEQ ID NO: 135, a CDR2 comprising the amino acid sequence set forth in SEQ ID NO: 136, and a CDR3 comprising the amino acid sequence set forth in SEQ ID NO: 137;

16) A CDR1 comprising the amino acid sequence set forth in SEQ ID NO: 139, a CDR2 comprising the amino acid sequence set forth in SEQ ID NO: 140, and a CDR3 comprising the amino acid sequence set forth in SEQ ID NO: 141;

17) A CDR1 comprising the amino acid sequence set forth in SEQ ID NO: 143, a CDR2 comprising the amino acid sequence set forth in SEQ ID NO: 144, and a CDR3 comprising the amino acid sequence set forth in SEQ ID NO: 145; or 18) A CDR1 comprising the amino acid sequence set forth in SEQ ID NO: 147, a CDR2 comprising the amino acid sequence set forth in SEQ ID NO: 148, and a CDR3 comprising the amino acid sequence set forth in SEQ ID NO: 149.

2. The bispecific antigen-binding molecule according to claim 1, wherein the immunoglobulin single variable domain specifically binding to TSLP comprises the amino acid sequence set forth in SEQ ID NO: 4, 8, 12, 16, 20, 24, 28, 32, 36, 40, 44, 48, 52, 56, 60, 64, 65, 66, 67, 68, 69, 70, 71, 72, 73, 74, 75, 76, 77 or 78, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 4, 8, 12, 16, 20, 24, 28, 32, 36, 40, 44, 48, 52, 56, 60, 64, 65, 66, 67, 68, 69, 70, 71, 72, 73, 74, 75, 76, 77 or 78 and maintaining the specific binding to TSLP; and the immunoglobulin single variable domain specifically binding to IL-33 comprises the amino acid sequence set forth in SEQ ID NO: 82, 86, 90, 94, 98, 102, 106, 110, 114, 118, 122, 126, 130, 134, 138, 142, 146, 150, 151, 152, 153, 154, 155, 156, 157 or 158, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 82, 86, 90, 94, 98, 102, 106, 110, 114, 118, 122, 126, 130, 134, 138, 142, 146, 150, 151, 152, 153, 154, 155, 156, 157 or 158 and maintaining the specific binding to IL-33.

3. The bispecific antigen-binding molecule according to claim 1, wherein the immunoglobulin single variable domain specifically binding to TSLP comprises a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43.

4. The bispecific antigen-binding molecule according to claim 1, wherein the immunoglobulin single variable domain specifically binding to TSLP comprises the amino acid sequence set forth in SEQ ID NO: 73, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 73, and maintaining the specific binding to TSLP.

5. The bispecific antigen-binding molecule according to claim 1, wherein the immunoglobulin single variable domain specifically binding to IL-33 comprises a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125.

6. The bispecific antigen-binding molecule according to claim 1, wherein the immunoglobulin single variable domain specifically binding to IL-33 comprises the amino acid sequence set forth in SEQ ID NO: 154, or the amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence set forth in SEQ ID NO: 154, and maintaining the specific binding to IL-33.

7. The bispecific antigen-binding molecule according to claim 1, wherein the immunoglobulin single variable domain specifically binding to TSLP comprises a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43; and the immunoglobulin single variable domain specifically binding to IL-33 comprises a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125.

8. The bispecific antigen-binding molecule according to claim 1, wherein the immunoglobulin single variable domain specifically binding to TSLP comprises the amino acid sequence set forth in SEQ ID NO: 73, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 73 and maintaining the specific binding to TSLP; and the immunoglobulin single variable domain specifically binding to IL-33 comprises the amino acid sequence set forth in SEQ ID NO: 154, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence set forth in SEQ ID NO: 154 and maintaining the specific binding to IL-33.

9. The bispecific antigen-binding molecule according to claim 1, wherein the immunoglobulin single variable domain is a VHH.

10. The bispecific antigen-binding molecule according to claim 1, wherein the immunoglobulin single variable domain is a VHH derived from a camelid.

11. The bispecific antigen-binding molecule according to claim 1, wherein the immunoglobulin single variable domain is a humanized VHH.

12. The bispecific antigen-binding molecule according to claim 1, wherein the first antigen-binding functional region comprises a plurality of immunoglobulin single variable domains specifically binding to TSLP, and/or the second antigen-binding functional region comprises a plurality of immunoglobulin single variable domains that specifically binding to IL-33.

13. The bispecific antigen-binding molecule according to claim 12, wherein the plurality of immunoglobulin single variable domains and/or the plurality of antigen-binding functional regions are optionally connected via a linker.

14. The bispecific antigen-binding molecule according to claim 13, wherein the linker is (GS)n, (GGS)n, (GGGS)n, or (GGGGS)n, where n is 1, 2, 3, 4, or 5.

15. The bispecific antigen-binding molecule according to claim 1, wherein the numbers of the first antigen-binding functional region and the second antigen-binding functional region are each independently 1, 2, or more than 2.

16. The bispecific antigen-binding molecule according to claim 1, wherein the first antigen-binding functional region is an anti-TSLP antibody or an antigen-binding fragment thereof, and/or the second antigen-binding functional region is an anti-IL-33 antibody or an antigen-binding fragment thereof.

17. The bispecific antigen-binding molecule according to claim 1, wherein the first antigen-binding functional region and the second antigen-binding functional region are each independently a heavy chain antibody, a heavy chain single domain antibody, a chimeric antibody or a humanized antibody.

18. The bispecific antigen-binding molecule according to claim 1, further comprising an immunoglobulin Fc domain.

19. The bispecific antigen-binding molecule according to claim 18, wherein the immunoglobulin Fc domain is a human immunoglobulin Fc domain.

20. The bispecific antigen-binding molecule according to claim 18, wherein the immunoglobulin Fc domain further comprises one or more amino acid mutations selected from $C_{220}A$, $L_{234}A$, $L_{235}A$, $M_{252}Y$, $S_{254}T$, $T_{256}E$ and $K_{447}$del.

21. The bispecific antigen-binding molecule according to claim 17, wherein the immunoglobulin Fc domain comprises the amino acid sequence set forth in SEQ ID NO: 159, 160 or 217, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 159, 160 or 217.

22. The bispecific antigen-binding molecule according to claim 18, wherein the immunoglobulin Fc domain is independently connected to the first antigen-binding functional region or the second antigen-binding functional region via an immunoglobulin hinge region or a linker.

23. The bispecific antigen-binding molecule according to claim 22, wherein the linker is (GS)n, (GGS)n, (GGGS)n, or (GGGGS)n, where n is 1, 2, 3, 4, or 5.

24. The bispecific antigen-binding molecule according to claim 18, wherein the bispecific antigen-binding molecule comprises one or more polypeptide chains each independently having the structure as shown in V1-Fc-L1-V2 from the N-terminus to the C-terminus, wherein V1 and V2 are different from each other and are each independently selected from the first antigen-binding functional region or the second antigen-binding functional region, L1 is a linker, and Fc is an immunoglobulin Fc domain; wherein, V1 and V2 are the first antigen-binding functional region or the second antigen-binding functional region respectively.

25. The bispecific antigen-binding molecule according to claim 1, comprising the amino acid sequence set forth in SEQ ID NO: 218, or the amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the sequence set forth in SEQ ID NO: 218 and maintaining the specific binding to TSLP and IL-33.

26. A composition comprising the bispecific antigen-binding molecule according to claim 1.

27. The composition according to claim 26, wherein the composition is a pharmaceutical composition, the pharmaceutical composition further comprises at least one pharmaceutically acceptable carrier and/or excipient, and optionally comprises one or more other pharmaceutically active therapeutic agents.

28. A method for treating, preventing or alleviating inflammatory diseases comprising administering a therapeutically effective amount of the bispecific antigen-binding molecule according to claim 1 to a subject in need thereof.

29. The method according to claim 28, wherein the inflammatory disease is a type 2 inflammatory disease.

30. The method according to claim 29, wherein the type 2 inflammatory disease is selected from asthma, chronic rhinosinusitis with or without nasal polyps, allergic rhinitis, chronic obstructive pulmonary disease, atopic dermatitis, prurigo nodularis, chronic spontaneous urticaria, and eosinophilic esophagitis.

31. The method according to claim 28 further comprising using in combination with one or more other therapeutic agents for treating inflammatory diseases.

\* \* \* \* \*